United States Patent
Jia et al.

(10) Patent No.: US 12,120,950 B2
(45) Date of Patent: Oct. 15, 2024

(54) ORGANIC COMPOUND, ELECTRONIC ELEMENT AND ELECTRONIC APPARATUS

(71) Applicant: Shaanxi Lighte Optoelectronics Material Co., Ltd., Xi'an (CN)

(72) Inventors: Zhiyan Jia, Xi'an (CN); Heming Zhang, Xi'an (CN); Yingwen Li, Xi'an (CN); Youngkook Kim, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 35 days.

(21) Appl. No.: 18/288,425

(22) PCT Filed: Jun. 21, 2022

(86) PCT No.: PCT/CN2022/100251
§ 371 (c)(1),
(2) Date: Oct. 26, 2023

(87) PCT Pub. No.: WO2023/011028
PCT Pub. Date: Feb. 9, 2023

(65) Prior Publication Data
US 2024/0244961 A1 Jul. 18, 2024

(30) Foreign Application Priority Data
Aug. 6, 2021 (CN) .......................... 202110901145.9

(51) Int. Cl.
| | | |
|---|---|---|
| *H10K 85/60* | (2023.01) | |
| *C07C 211/54* | (2006.01) | |
| *C07C 211/61* | (2006.01) | |
| *C07D 209/86* | (2006.01) | |
| *C07D 209/88* | (2006.01) | |
| *C07D 307/91* | (2006.01) | |
| *C07D 333/76* | (2006.01) | |
| *C07D 409/12* | (2006.01) | |
| *C07F 7/08* | (2006.01) | |
| *C09K 11/06* | (2006.01) | |
| *H10K 50/15* | (2023.01) | |
| *H10K 85/40* | (2023.01) | |

(52) U.S. Cl.
CPC .......... *H10K 85/633* (2023.02); *C07C 211/54* (2013.01); *C07C 211/61* (2013.01); *C07D 209/86* (2013.01); *C07D 209/88* (2013.01); *C07D 307/91* (2013.01); *C07D 333/76* (2013.01); *C07D 409/12* (2013.01); *C07F 7/081* (2013.01); *C09K 11/06* (2013.01); *H10K 85/40* (2023.02); *H10K 85/636* (2023.02); *C07C 2603/18* (2017.05); *C07C 2603/97* (2017.05); *C09K 2211/1011* (2013.01); *C09K 2211/1014* (2013.01); *C09K 2211/1018* (2013.01); *H10K 50/156* (2023.02); *H10K 85/615* (2023.02); *H10K 85/624* (2023.02); *H10K 85/626* (2023.02); *H10K 85/6572* (2023.02); *H10K 85/6574* (2023.02); *H10K 85/6576* (2023.02)

(58) Field of Classification Search
CPC ... C07C 211/52; C07C 211/54; C07C 211/57; C07C 211/59; C07C 211/61; H10K 85/633; H10K 85/636
See application file for complete search history.

(56) References Cited

U.S. PATENT DOCUMENTS

2021/0193925 A1 6/2021 Oh

FOREIGN PATENT DOCUMENTS

| | | | |
|---|---|---|---|
| CN | 105601613 | A | 5/2016 |
| CN | 108863813 | A | 11/2018 |
| CN | 111217716 | A | 6/2020 |
| CN | 111433319 | A | 7/2020 |
| CN | 111909043 | A | 11/2020 |
| CN | 113735719 | A | 12/2021 |
| CN | 114133332 | A | 3/2022 |
| JP | 2013177379 | A | 9/2013 |
| JP | 2019135228 | A | 8/2019 |

(Continued)

OTHER PUBLICATIONS

International Search Report from corresponding International Application No. PCT/CN2022/100251, mailed on Sep. 27, 2022, 6 pages with translation.

*Primary Examiner* — Vu A Nguyen
(74) *Attorney, Agent, or Firm* — Tucker Ellis LLP

(57) ABSTRACT

The present application relates to an organic compound, an electronic element and an electronic apparatus. A structural formula of the organic compound of the present application is represented by Formula I, and when used in an organic electroluminescent device, the organic compound may significantly improve the performance of the device.

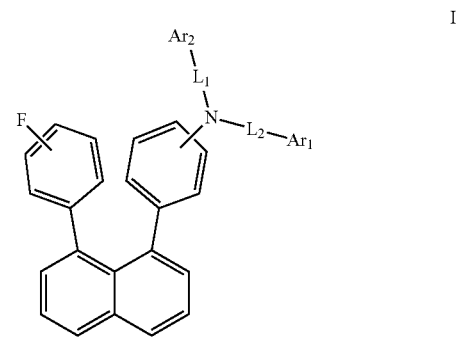

11 Claims, 1 Drawing Sheet

(56) References Cited

FOREIGN PATENT DOCUMENTS

| KR | 1020180124728 A | 11/2018 | | |
|---|---|---|---|---|
| KR | 20190077158 A | * | 7/2019 | ............. H10K 50/15 |
| KR | 1020190077158 A | | 7/2019 | |

* cited by examiner

ORGANIC COMPOUND, ELECTRONIC ELEMENT AND ELECTRONIC APPARATUS

CROSS REFERENCE TO RELATED APPLICATIONS

The present application claims the priority of Chinese patent application CN202110901145.9 filed on Aug. 6, 2021, and the full content of the above Chinese patent application is incorporated herein by reference.

TECHNICAL FIELD

The present application belongs to the technical field of organic materials, and specifically provides an organic compound, an electronic element and an electronic device.

BACKGROUND

With the development of electronic technology and the progress of material science, the application range of electronic element for realizing electroluminescence or photoelectric conversion is wider and wider. Such electronic element generally includes a cathode and an anode which are disposed oppositely, and a functional layer disposed between the cathode and the anode. The functional layer is composed of a plurality of organic or inorganic film layers and generally includes an energy conversion layer, a hole transporting layer located between the energy conversion layer and the anode, and an electron transporting layer located between the energy conversion layer and the cathode.

Taking an organic electroluminescent device as an example, it generally includes an anode, a hole transporting layer, an organic light-emitting layer, an electron transporting layer and a cathode which are sequentially stacked. When voltage is applied to the cathode and the anode, an electric field is generated between the two electrodes, electrons on the cathode side move towards an organic light-emitting layer and holes on the anode side also move towards an organic light-emitting layer under the action of the electric field, the electrons and the holes are combined in the organic light-emitting layer to form excitons, the excitons are in an excited state and release energy outwards, and then the organic light-emitting layer emits light outwards.

In general, when an organic electroluminescent element is driven or kept in a high-temperature environment, the organic electroluminescent element will have adverse effects such as a change in light color, a decrease in luminous efficiency, an increase in driving voltage, and shortening of luminescence service life. To prevent this effect, the glass transition temperature (Tg) of a material of the hole transporting layer must be raised. At present, the reported hole transporting layer materials have low glass transition temperature due to their low molecular weight, the materials are easy to crystallize due to repeated charge and discharge during use of the materials, and the film uniformity is damaged, thus affecting the service life of the materials.

Thus, it is of a very important practical application value to develop stable and efficient organic hole transporting layer materials to improve the charge mobility, reduce the driving voltage, improve the luminous efficiency of the device, and prolong the service life of the device.

SUMMARY

The object of the present application is to provide an organic compound, an electronic element and an electronic device. When the organic compound is used in an organic electroluminescent device, the performance of the device can be improved.

A first aspect of the present application provides an organic compound having a structure represented by Formula I:

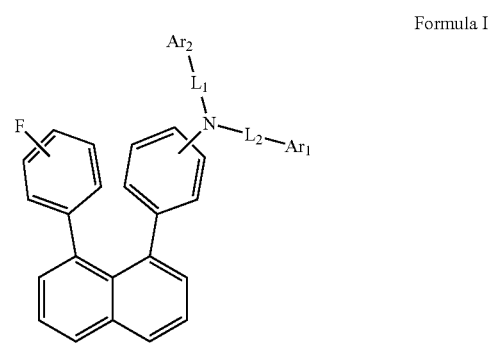

Formula I where $Ar_1$ and $Ar_2$ are the same or different, and are each independently selected from a substituted or unsubstituted aryl with 6 to 40 carbon atoms, or a substituted or unsubstituted heteroaryl with 3 to 30 carbon atoms;

$L_1$ and $L_2$ are the same or different, and are each independently selected from a single bond, a substituted or unsubstituted arylene with 6 to 30 carbon atoms, or a substituted or unsubstituted heteroarylene with 3 to 30 carbon atoms; and substituents of $Ar_1$, $Ar_2$, $L_1$, and $L_2$ are the same or different, and are each independently selected from deuterium, a halogen group, a cyano, a trialkylsilyl with 3 to 12 carbon atoms, an alkyl with 1 to 10 carbon atoms, a haloalkyl with 1 to 10 carbon atoms, an aryl with 6 to 20 carbon atoms, or a heteroaryl with 3 to 20 carbon atoms; and optionally, in $Ar_1$ and $Ar_2$, any two adjacent substituents form a substituted or unsubstituted 3-membered to 15-membered ring, and substituents of the 3-membered to 15-membered ring are independently selected from deuterium, a halogen group, a cyano, a trialkylsilyl with 3 to 6 carbon atoms, an alkyl with 1 to 5 carbon atoms or a haloalkyl with 1 to 5 carbon atoms.

A second aspect of the present application provides an electronic element, including an anode and a cathode which are oppositely disposed, and a functional layer disposed between the anode and the cathode; where the functional layer includes the above organic compound.

A third aspect of the present application provides an electronic device, including the electronic element in the second aspect.

The organic compound of the present application has 1,8-diphenyl substituted naphthyl as a core structure, benzene at position 1 of the naphthyl is connected to a fluorine atom (F), and benzene at position 8 of the naphthyl is connected to a triarylamine structure. The 1,8-diphenyl substituted naphthyl has larger steric hindrance, the steric configuration of a molecule is adjusted, stacking between molecules can be effectively avoided, and the film-forming properties are improved, and the electron distribution effect of this group can also improve the hole mobility. Further, F atom connected to the benzene at the position 1 has high electronegativity, so that the HOMO energy level and the LUMO energy level of the compound can be better separated, ensuring that the material has a higher $T_1$ value. In addition, the F atom has a smaller van der Waals radius and smaller steric hindrance, which can enhance non-covalent interaction with an H atom, and intermolecular aggregation is further improved, thus ensuring that a device has higher hole mobility, and electrons and excitons can be effectively prevented from entering a hole transporting layer. When the organic compound of the present application is applied to an organic electroluminescent device, the luminous efficiency and service life of the device can be simultaneously improved.

Other features and advantages of the present application will be described in detail in the subsequent specific embodiments.

BRIEF DESCRIPTION OF THE DRAWINGS

The accompanying drawings are used to provide a further understanding of the present application and constitute a part of the description, and are used to explain the present application together with the following specific embodiments, but do not constitute limitations on the present application.

Figure 1:
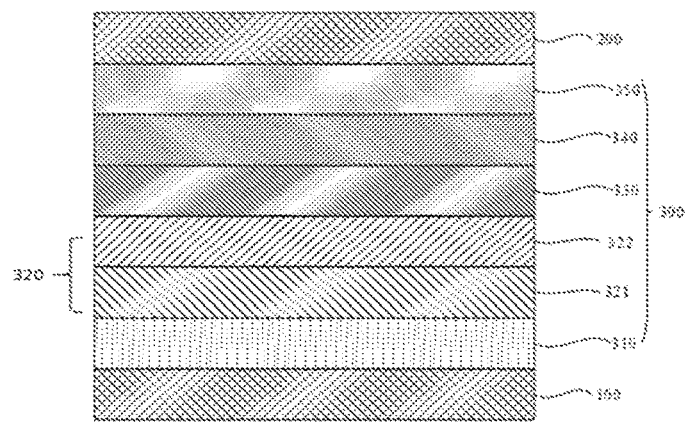
FIG. 1 is a structural schematic diagram of an organic electroluminescent device according to one embodiment of the present application.

DESCRIPTION OF REFERENCE SIGNS 100, anode; 200, cathode; 300, functional layer; 310, hole injection layer; 320, hole transporting layer; 321, first hole transporting layer; 322, second hole transporting layer; 330, organic light-emitting layer; 340, electron transporting layer; 350, electron injection layer; 360, photoelectric conversion layer; 400, first electronic device; and 500, second electronic device

DETAILED DESCRIPTION

Example embodiments will now be described more fully with reference to the accompanying drawings. However, the example embodiments can be implemented in a variety of forms, and should not be understood as a limitation to the instances set forth here; and on the contrary, these example embodiments are provided such that the present application will be more comprehensive and complete, and the concepts of the example embodiments are comprehensively conveyed to those skilled in the art. The described features, structures, or characteristics may be incorporated in one or more embodiments in any suitable manner. In the following description, many specific details are provided to give a sufficient understanding of the embodiments of the present application.

In a first aspect, the present application provides an organic compound having a structure represented by Formula I:

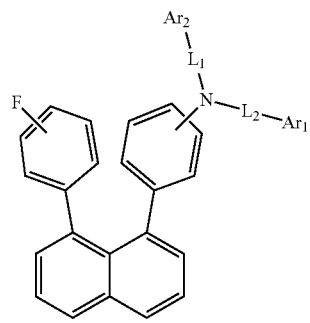

Formula I where $Ar_1$ and $Ar_2$ are the same or different, and are each independently selected from a substituted or unsubstituted aryl with 6 to 40 carbon atoms, or a substituted or unsubstituted heteroaryl with 3 to 30 carbon atoms;

$L_1$ and $L_2$ are the same or different, and are each independently selected from a single bond, a substituted or unsubstituted arylene with 6 to 30 carbon atoms, or a substituted or unsubstituted heteroarylene with 3 to 30 carbon atoms; and substituents of $Ar_1$, $Ar_2$, $L_1$, and $L_2$ are the same or different, and are each independently selected from deuterium, a halogen group, a cyano, a trialkylsilyl with 3 to 12 carbon atoms, an alkyl with 1 to 10 carbon atoms, a haloalkyl with 1 to 10 carbon atoms, an aryl with 6 to 20 carbon atoms, or a heteroaryl with 3 to 20 carbon atoms; and optionally, in $Ar_1$ and $Ar_2$, any two adjacent substituents form a substituted or unsubstituted 3-membered to 15-membered ring, and substituents of the 3-membered to 15-membered ring are independently selected from deuterium, a halogen group, a cyano, a trialkylsilyl with 3 to 6 carbon atoms, an alkyl with 1 to 5 carbon atoms or a haloalkyl with 1 to 5 carbon atoms.

In the present application, the terms "optional" and "optionally" mean that the subsequently described event or circumstance may but need not occur, and that the description includes instances where the event or circumstance occurs or does not occur. For example, "optionally, any two adjacent substituents form a ring", which means that the two substituents can, but need not, form a ring, including scenarios in which two adjacent substituents form a ring and scenarios in which two adjacent substituents do not form a ring. For another example, "optionally, in $Ar_1$ and $Ar_2$, any two adjacent substituents form a substituted or unsubstituted 3-membered to 15-membered ring", which includes: in $Ar_1$ and $Ar_2$, any two adjacent substituents may be connected to each other to form a 3-membered to 15-membered ring, or in $Ar_1$ and $Ar_2$, any two adjacent substituents may also be present independently of each other without forming a ring. "Any two adjacent" can include the condition that a same atom has two substituents, and can also include the condition that two adjacent atoms each have one substituent; when the same atom has two substituents, the two substituents may form a saturated or unsaturated ring with the atom to which they are connected; and when two adjacent atoms each have one substituent, the two substituents may be fused to form a ring.

In the present application, the adopted description modes "each independently selected from" and "respectively and independently selected from" as well as "is independently" and "independently selected from" can be interchanged, and should be understood in a broad sense, which means that in different groups, specific options expressed between the same symbols do not influence each other, or in a same group, specific options expressed between the same symbols do not influence each other. For example, the meaning of "

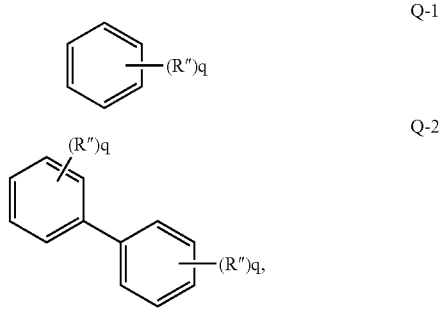

where each q is independently 0, 1, 2 or 3, and each R" is independently selected from hydrogen, deuterium, fluorine and chlorine" is as follows: formula Q-1 represents that q substituent R"(s) exist on a benzene ring, each R" can be the same or different, and options of each R" do not influence each other; and formula Q-2 represents that each benzene ring of biphenyl has q substituent R"(s), the number q of the substituent R"(s) on the two benzene rings can be the same or different, each R" can be the same or different, and options of each R" do not influence each other.

In the present application, the term such as "substituted or unsubstituted" means that a functional group described behind the term may have or do not have a substituent (in the following, the substituent is collectively referred to as Rc in order to facilitate description). For example, the "substituted or unsubstituted aryl" refers to aryl with the substituent Rc or aryl without a substituent. The above substituent, i.e., Rc, may be, for example, deuterium, a halogen, acyano, a heteroaryl, an aryl, an alkyl, a trialkylsilyl, a haloalkyl, or the like.

In the present application, the number of carbon atoms in a substituted or unsubstituted functional group refers to the number of all carbon atoms. For example, if $L_1$ is substituted arylene with 12 carbon atoms, the number of all carbon atoms of the arylene and substituents on the arylene is 12.

In the present application, aryl refers to an optional functional group or substituent derived from an aromatic carbocyclic ring. The aryl may be monocyclic aryl (e.g., phenyl) or polycyclic aryl, in other words, the aryl can be monocyclic aryl, fused aryl, two or more monocyclic aryl conjugatedly connected through carbon-carbon bonds, monocyclic aryl and fused aryl which are conjugatedly connected through a carbon-carbon bond, or two or more fused aryl conjugatedly connected through carbon-carbon bonds. That is, unless otherwise noted, two or more aromatic groups conjugatedly connected through carbon-carbon bonds can also be regarded as the aryl of the present application. The fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se and Si. For example, in the present application, biphenyl, terphenyl, and the like are aryl. Examples of the aryl may include, but are not limited to, phenyl, naphthyl, fluorenyl, anthryl, phenanthryl, biphenyl, terphenyl, benzo[9,10]phenanthryl, pyrenyl, benzofluoranthenyl, chrysenyl, and the like.

In the present application, the arylene involved refers to a divalent group formed by further loss of one hydrogen atom from aryl.

In the present application, the substituted aryl may be that one or two or more hydrogen atoms in the aryl are substituted by groups such as deuterium atom, halogen group, —CN, aryl, heteroaryl, trialkylsilyl, alkyl, cycloalkyl, haloalkyl, and the like. Specific examples of heteroaryl-substituted aryl include, but are not limited to, dibenzofuranyl-substituted phenyl, dibenzothiophene-substituted phenyl, pyridine-substituted phenyl, and the like. It should be understood that the number of carbon atoms of the substituted aryl refers to the total number of carbon atoms of the aryl and substituents on the aryl, for example, substituted aryl with 18 carbon atoms means that the total number of carbon atoms of the aryl and substituents on the aryl is 18.

In the present application, the heteroaryl refers to a monovalent aromatic ring containing at least one heteroatom in the ring or its derivative, and the heteroatom may be at least one of B, O, N, P, Si, Se and S. The heteroaryl may be a monocyclic heteroaryl or a polycyclic heteroaryl, in other words, the heteroaryl may be a single aromatic ring system or a plurality of aromatic ring systems conjugatedly connected through carbon-carbon bonds, and any aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, phenothiazinyl, silafluorenyl, dibenzofuranyl, N-phenylcarbazolyl, N-pyridylcarbazolyl, N-methylcarbazolyl and the like, but is not limited to this. The thienyl, furyl, phenanthrolinyl and the like are heteroaryl of the single aromatic ring system, and N-phenylcarbazolyl and N-pyridylcarbazolyl are heteroaryl of the multiple aromatic rings systems conjugatedly connected through carbon-carbon bonds.

In the present application, the heteroarylene involved refers to a divalent group formed by further loss of one hydrogen atom from heteroaryl.

In the present application, the substituted heteroaryl may be that one or two or more hydrogen atoms in the heteroaryl are substituted by groups such as deuterium atom, halogen group, —CN, aryl, heteroaryl, trialkylsilyl, alkyl, cycloalkyl, haloalkyl, and the like. Specific examples of aryl-substituted heteroaryl include, but are not limited to, phenyl-substituted dibenzofuranyl, phenyl-substituted dibenzothienyl, phenyl-substituted pyridyl and the like. It should be understood that the number of carbon atoms of the substituted heteroaryl refers to the total number of carbon atoms of heteroaryl and substituents on the heteroaryl.

In the present application, the alkyl with 1 to 10 carbon atoms may include linear alkyl with 1 to 10 carbon atoms and branched alkyl with 3 to 10 carbon atoms. The number of carbon atoms of the alkyl is, for example, 1, 2, 3, 4, 5, 6, 7, 8, 9, or 10, and specific examples of the alkyl include, but are not limited to, methyl, ethyl, n-propyl, isopropyl, n-butyl, isobutyl, tert-butyl, n-pentyl, isopentyl, neopentyl, n-hexyl, n-heptyl, n-octyl, 2-ethylhexyl, nonyl, decyl, 3,7-dimethyloctyl, and the like.

In the present application, the halogen group may be, for example, fluorine, chlorine, bromine or iodine.

In the present application, specific examples of trialkylsilyl include, but are not limited to, trimethylsilyl, triethylsilyl, and the like.

In the present application, specific examples of haloalkyl include, but are not limited to, trifluoromethyl.

In the present application, the number of carbon atoms of cycloalkyl with 3 to 10 carbon atoms may be, for example, 3, 4, 5, 6, 7, 8, 9, or 10. Specific examples of cycloalkyl include, but are not limited to, cyclopentyl, cyclohexyl, and adamantyl.

In the present application, the number of carbon atoms of aryl as a substituent may be 6 to 20, for example, the number of carbon atoms is 6, 7, 8, 9, 10, 11, 12, 13, 14, 15, 16, 17, 18, 19, or 20, and specific examples include, but are not limited to, phenyl, biphenyl, naphthyl, anthryl, phenanthryl, chrysenyl, and fluorenyl.

In the present application, the number of carbon atoms of heteroaryl as a substituent may be 3 to 20, for example, the number of carbon atoms is 3, 4, 5, 6, 7, 8, 9, 10, 11, 12, 13, 14, 15, 16, 17, 18, 19, or 20, and specific examples include, but are not limited to, pyridyl, pyrimidinyl, carbazolyl, dibenzofuranyl, dibenzothienyl, quinolinyl, quinazolinyl, quinoxalinyl, and isoquinolinyl.

In the present application, an unpositioned connecting bond refers to a single bond " -ξ- " extending from a ring system, which means that one end of the connecting bond can be connected with any position in the ring system through which the bond penetrates, and the other end of the connecting bond is connected with the remaining part of a compound molecule. For example, as shown in the following formula (f), naphthyl represented by the formula (f) is connected to other positions of a molecule through two unpositioned connecting bonds penetrating a dicyclic ring, and its meaning includes any one possible connecting mode represented by formulae (f-1) to (f-10):

(f)

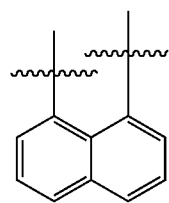

(f-1)

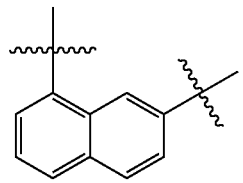

(f-2)

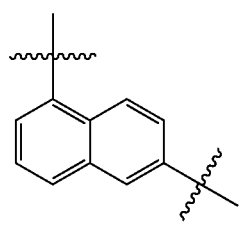

(f-3)

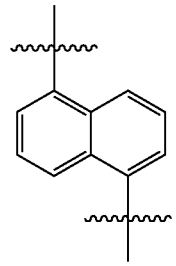

(f-4)

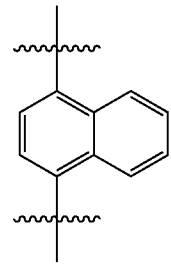

(f-5)

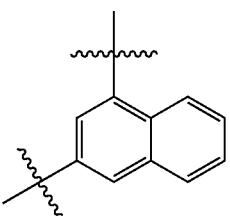

(f-6)

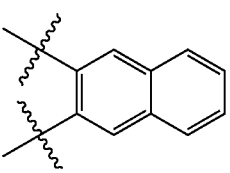

(f-7)

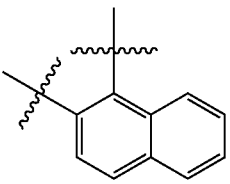

(f-8)

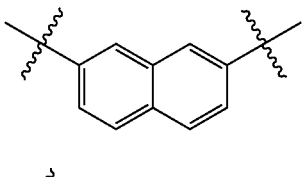

(f-9)

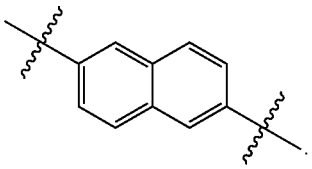

(f-10)

For another example, as shown in the following formula (X'), dibenzofuranyl represented by the formula (X') is connected with other positions of a molecule through one unpositioned connecting bond extending from the middle of a benzene ring on one side, and its meaning includes any one possible connecting mode represented by formulae (X'-1) to (X'-4):

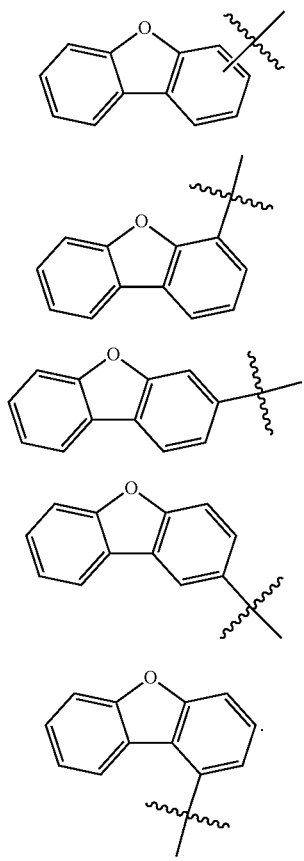

In some embodiments, $Ar_1$ and $Ar_2$ are each independently selected from a substituted or unsubstituted aryl with 6 to 33 carbon atoms, or a substituted or unsubstituted heteroaryl with 5 to 20 carbon atoms. For example, $Ar_1$ and $Ar_2$ are each independently selected from a substituted or unsubstituted aryl with 6, 7, 8, 9, 10, 11, 12, 13, 14, 15, 16, 17, 18, 19, 20, 21, 22, 23, 24, 25, 26, 27, 28, 29, 30, 31, 32, or 33 carbon atoms; or a substituted or unsubstituted heteroaryl with 5, 6, 7, 8, 9, 10, 11, 12, 13, 14, 15, 16, 17, 18, 19, or 20 carbon atoms.

Optionally, substituents of $Ar_1$ and $Ar_2$ are each independently selected from deuterium, a fluorine, a cyano, a trialkylsilyl with 3 to 6 carbon atoms, a haloalkyl with 1 to 5 carbon atoms, an alkyl with 1 to 5 carbon atoms, an aryl with 6 to 12 carbon atoms or a heteroaryl with 5 to 12 carbon atoms; optionally, any two adjacent substituents of $Ar_1$ and $Ar_2$ form a substituted or unsubstituted 5-membered to 13-membered ring; and substituents of the 5-membered to 13-membered ring are independently selected from deuterium, a fluorine, a cyano, a trimethylsilyl, a trifluoromethyl, a methyl, an ethyl, an isopropyl or a tert-butyl.

Optionally, $Ar_1$ and $Ar_2$ are each independently selected from a substituted or unsubstituted phenyl, a substituted or unsubstituted naphthyl, a substituted or unsubstituted biphenyl, a substituted or unsubstituted fluorenyl, a substituted or unsubstituted dibenzofuranyl, a substituted or unsubstituted pyridyl, a substituted or unsubstituted dibenzothienyl, a substituted or unsubstituted carbazolyl, a substituted or unsubstituted phenanthryl, or a substituted or unsubstituted triphenylene.

Preferably, the substituents of $Ar_1$ and $Ar_2$ are selected from deuterium, a fluorine, a cyano, a trimethylsilyl, a trifluoromethyl, a methyl, an ethyl, an isopropyl, a tert-butyl, a phenyl, a naphthyl or a biphenyl; and optionally, in $Ar_1$ and $Ar_2$, any two adjacent substituents form a cyclopentane

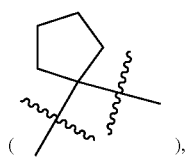 [SMILES: *C1(*)CCCC1]

a cyclohexane

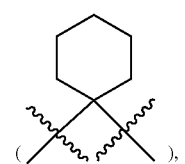

a fluorene ring

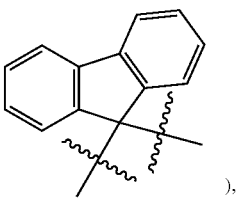

or a tert-butyl substituted fluorene ring

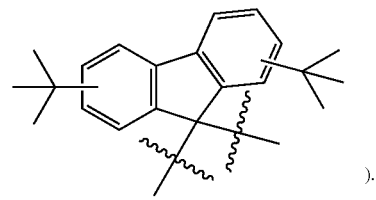

Optionally, $Ar_1$ and $Ar_2$ are each independently selected from a substituted or unsubstituted group W, where the unsubstituted group W is selected from the following groups:

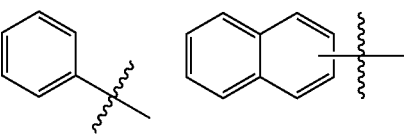

-continued

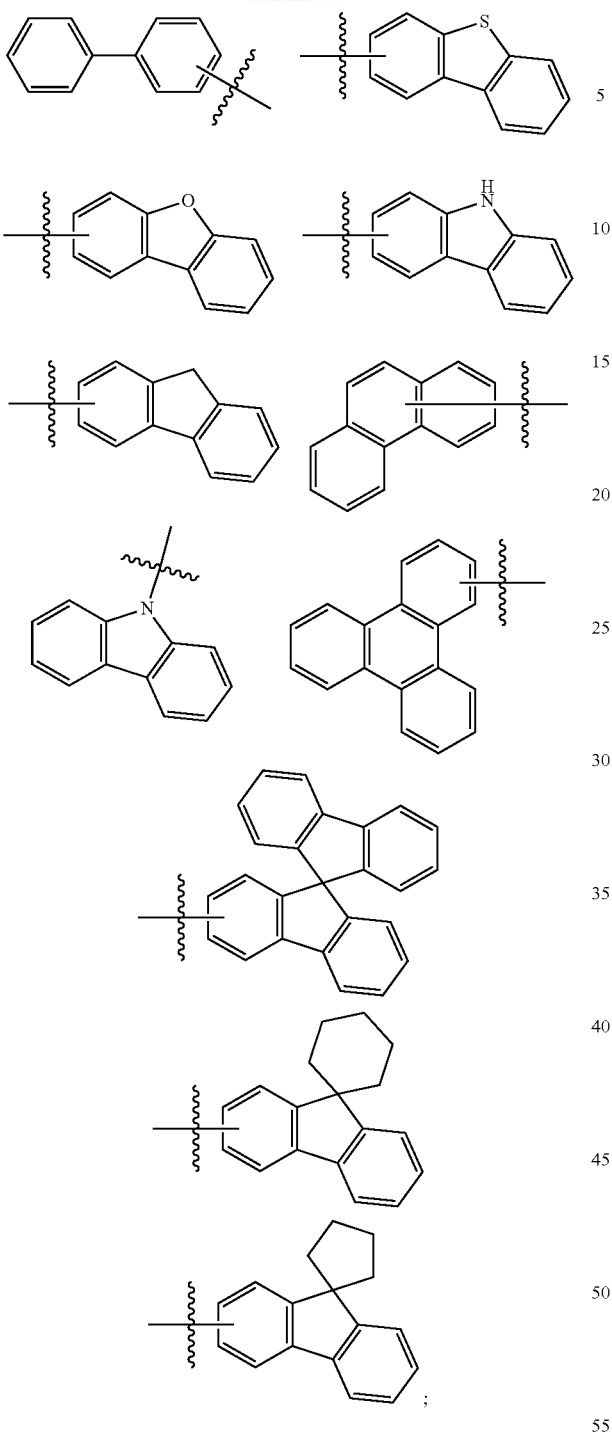

and where the substituted group W has one or two or more substituents, the substituents are independently selected from deuterium, a fluorine, a cyano, a trimethylsilyl, a trifluoromethyl, a methyl, an ethyl, an isopropyl, a tert-butyl, a phenyl, a naphthyl or a biphenyl, and when the number of the substituents is greater than 1, the substituents are the same or different.

In one embodiment, $Ar_1$ and $Ar_2$ are each independently selected from

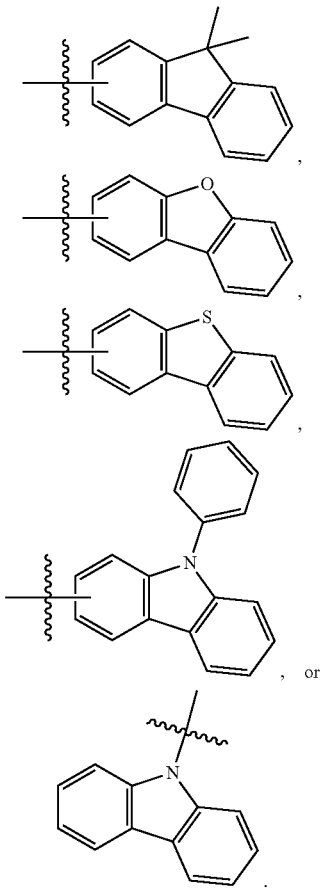

Preferably, $Ar_1$ is

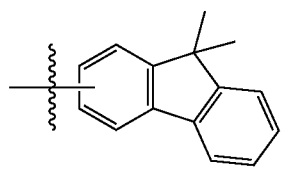

and $Ar_2$ is

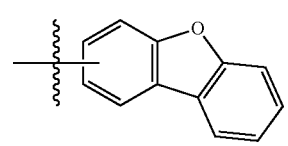

or

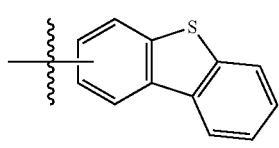

and in this case, when the organic compound is applied to an organic light-emitting device, the service life of the device can be further improved.
Optionally, Ar$_1$ and Ar$_2$ are each independently selected from the following groups:
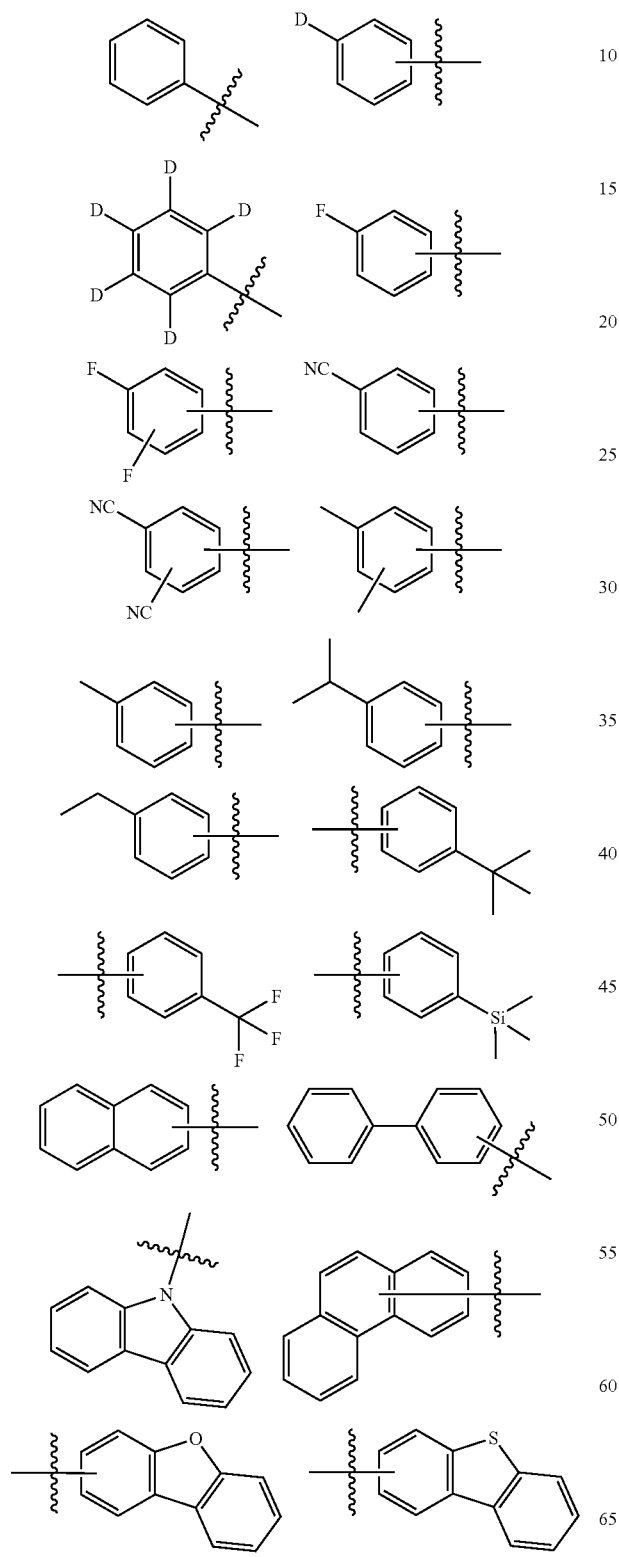
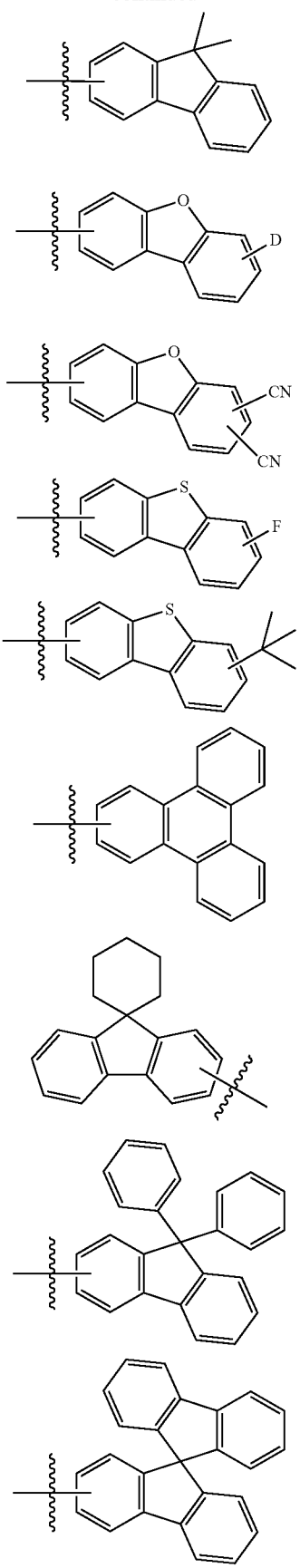

-continued
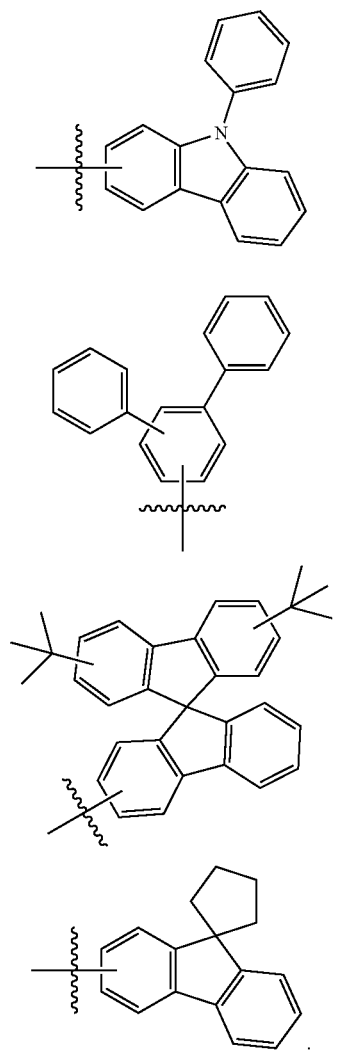
Further optionally, $Ar_1$ and $Ar_2$ are each independently selected from the following groups:
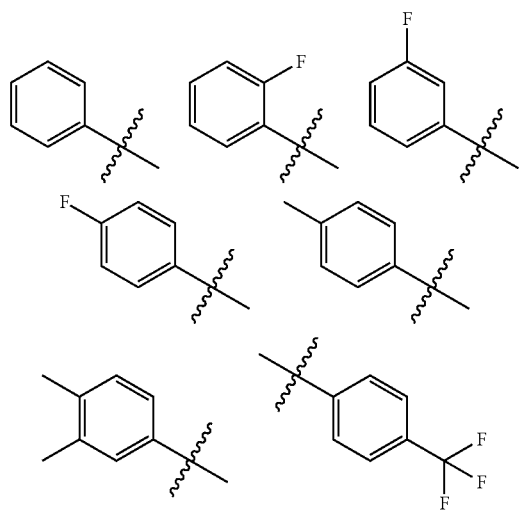
-continued
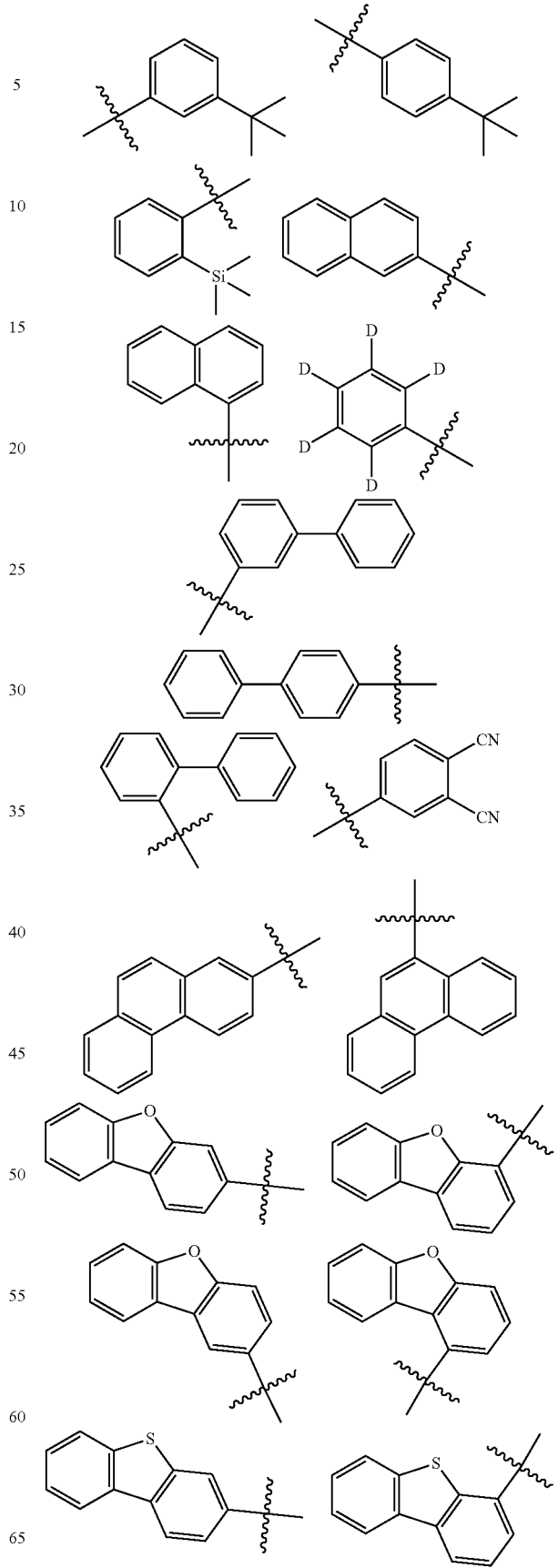

-continued
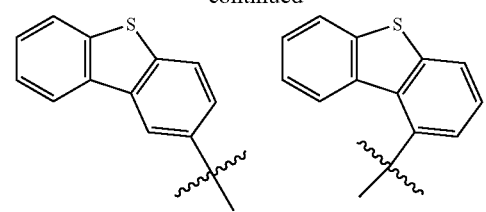
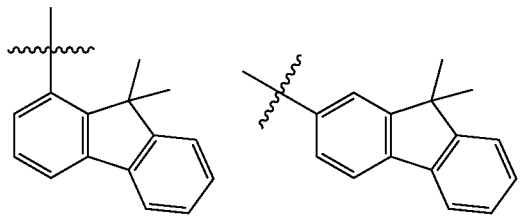
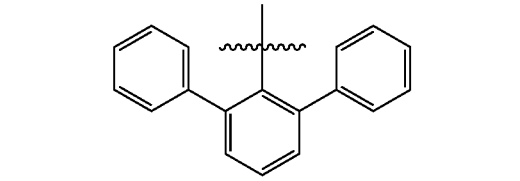
-continued
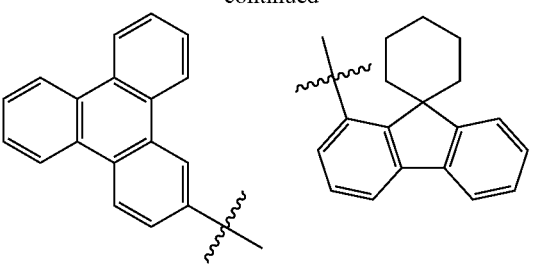
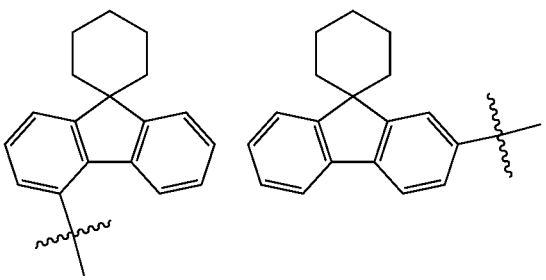
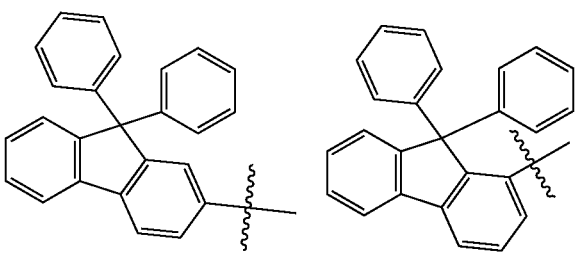
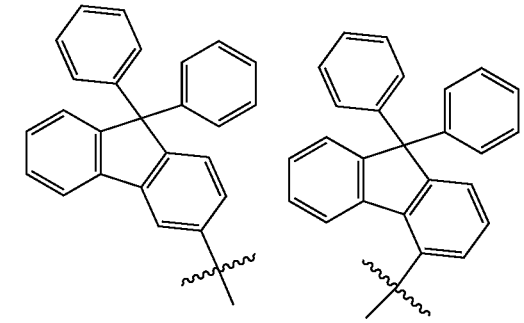
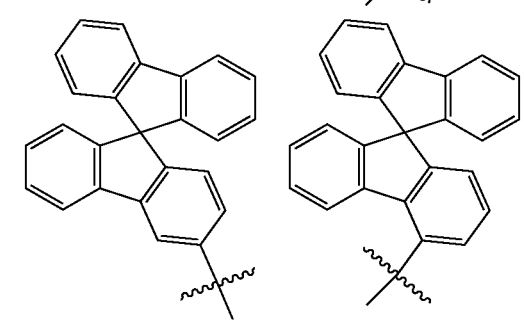

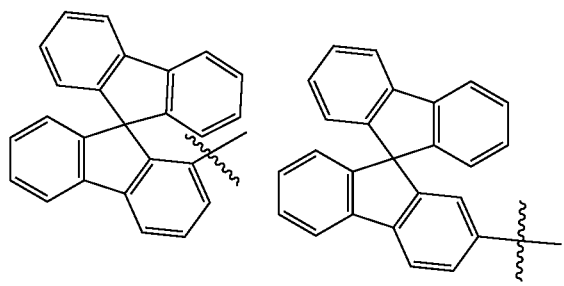
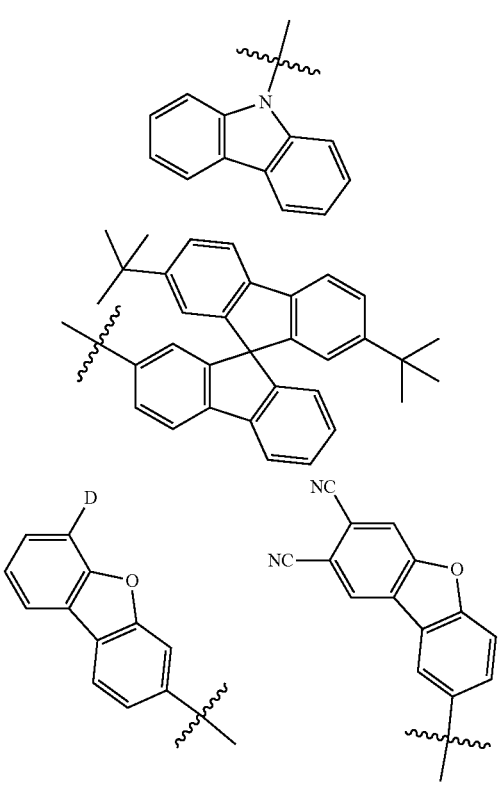
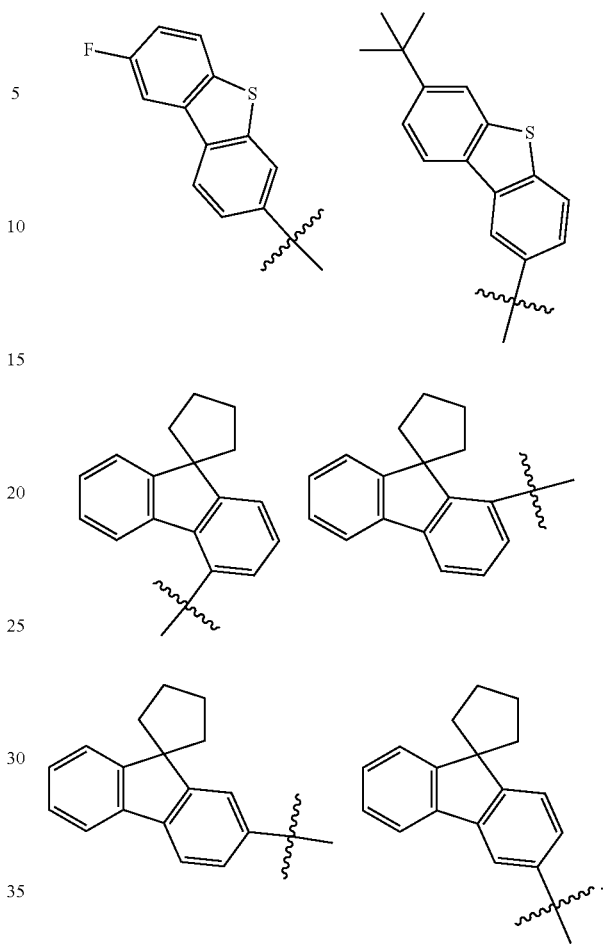

In some embodiments, $L_1$ and $L_2$ are each independently selected from a single bond, a substituted or unsubstituted arylene with 6 to 12 carbon atoms, or a substituted or unsubstituted heteroarylene with 5 to 12 carbon atoms. For example, $L_1$ and $L_2$ are each independently selected from a single bond; a substituted or unsubstituted arylene with 6, 7, 8, 9, 10, 11, or 12 carbon atoms; or a substituted or unsubstituted heteroarylene with 5, 6, 7, 8, 9, 10, 11, or 12 carbon atoms.

Preferably, substituents of $L_1$ and $L_2$ are each independently selected from deuterium, a fluorine, a cyano, a trialkylsilyl with 3 to 6 carbon atoms, an alkyl with 1 to 5 carbon atoms, a haloalkyl with 1 to 5 carbon atoms or phenyl.

Optionally, $L_1$ and $L_2$ are each independently selected from a single bond, a substituted or unsubstituted phenylene, a substituted or unsubstituted naphthylene, or a substituted or unsubstituted biphenylene.

Preferably, substituents of $L_1$ and $L_2$ are each independently selected from deuterium, a fluorine, a cyano, a trimethylsilyl, a methyl, an ethyl, an isopropyl, a tert-butyl, a trifluoromethyl, a phenyl or a naphthyl.

Optionally, $L_1$ and $L_2$ are each independently selected from a single bond, or a substituted or unsubstituted group V, where the unsubstituted group V is selected from the following groups:

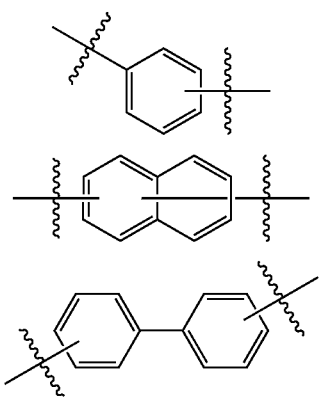

where the substituted group V has one or two or more substituents, the substituents are independently selected from a methyl, an ethyl, an isopropyl, a tert-butyl or a phenyl, and when the number of the substituents is greater than 1, the substituents are the same or different.

Optionally, $L_1$ and $L_2$ are each independently selected from a single bond or the group consisting of:

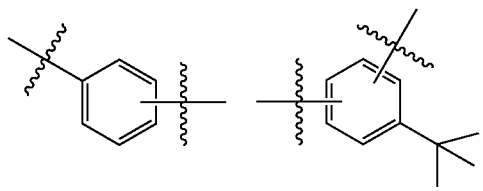

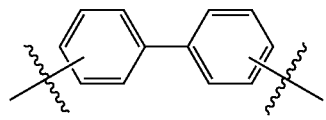

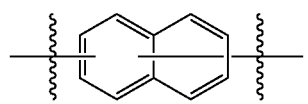

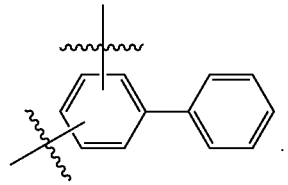

Further optionally, $L_1$ and $L_2$ are each independently selected from a single bond or the group consisting of:

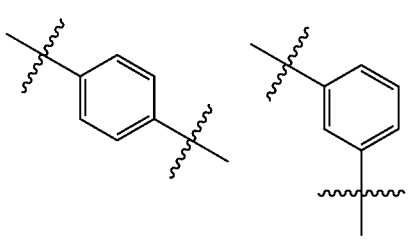

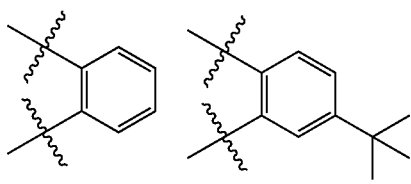

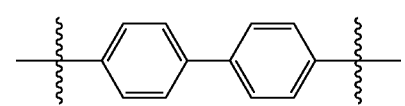

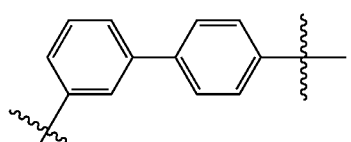

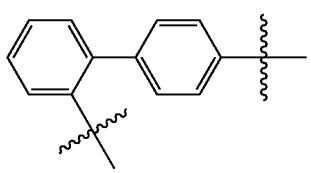

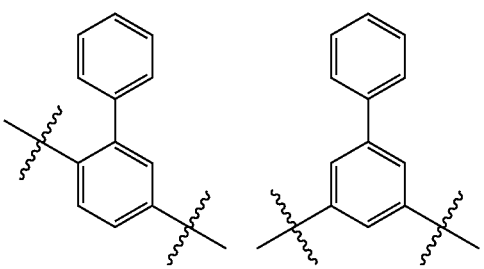

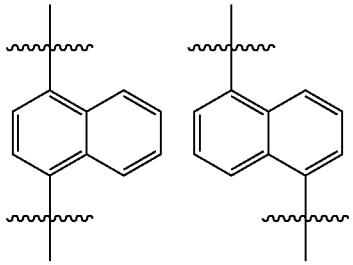

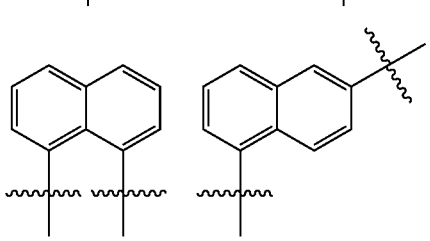

Optionally, the organic compound is selected from the group consisting of the following compounds:
1
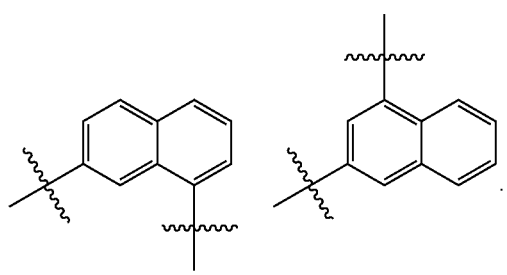
2
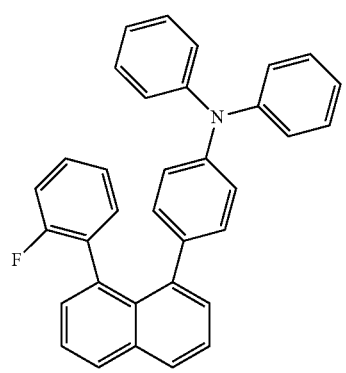
3
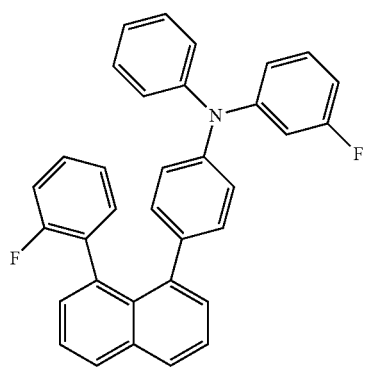
4
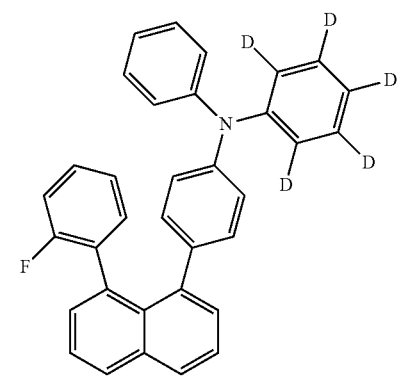
5
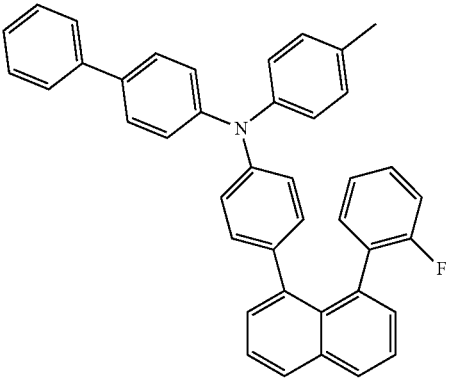
6
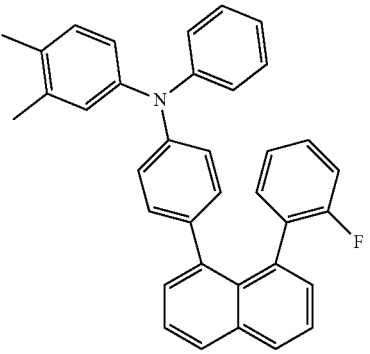
7
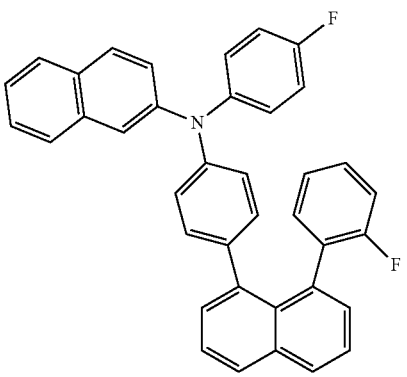

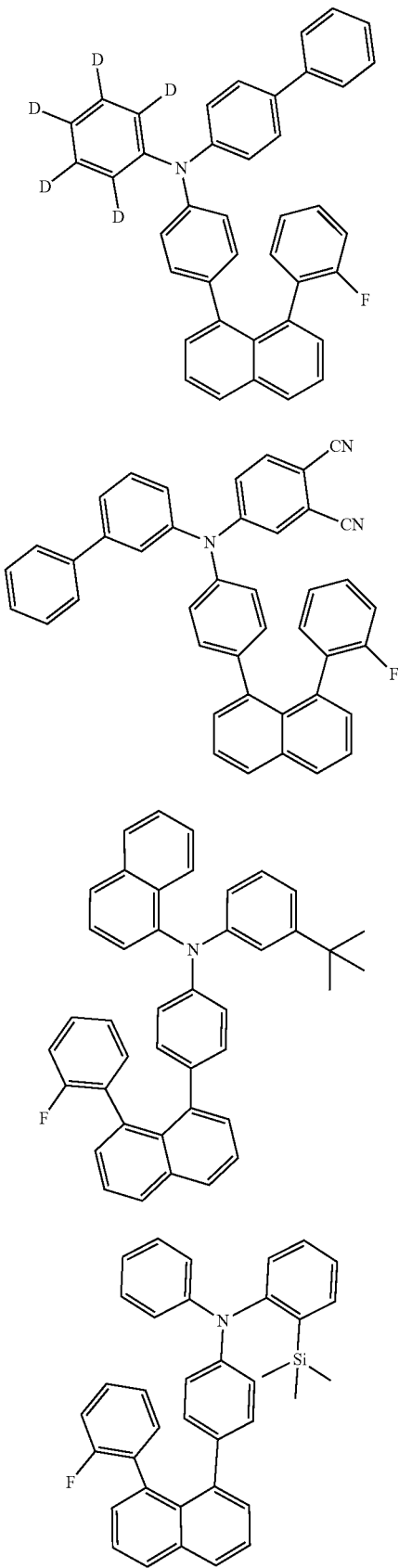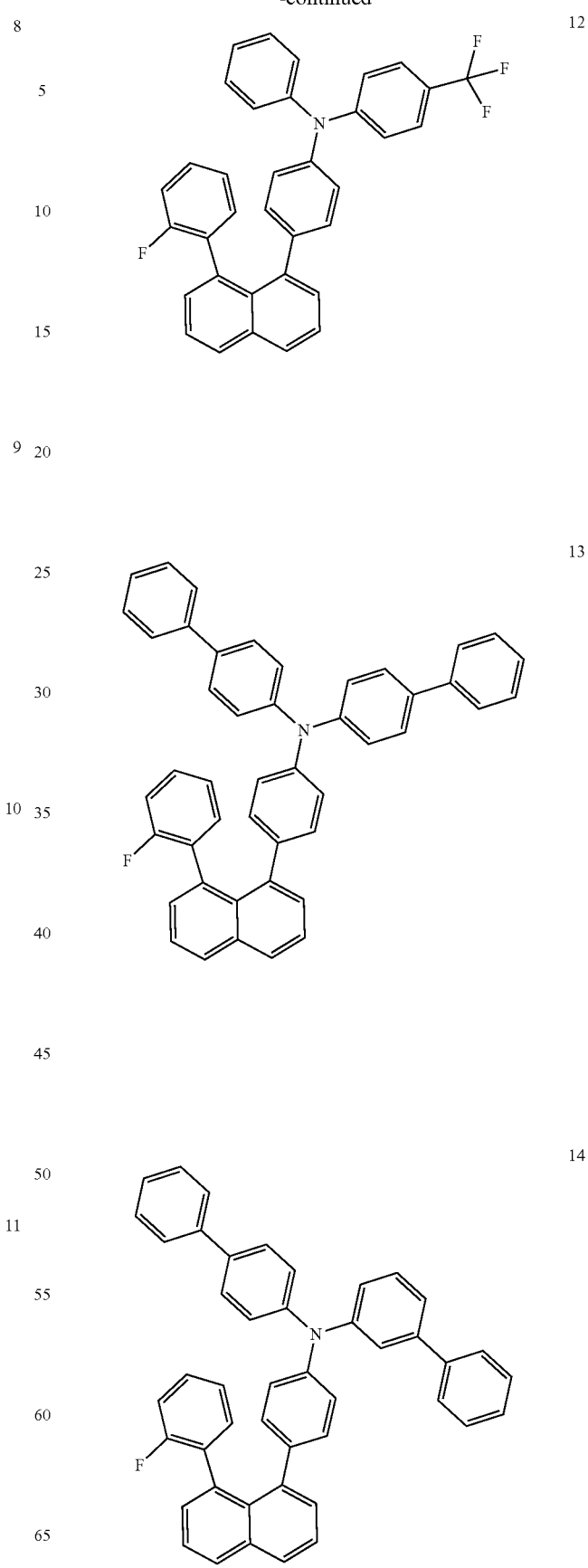

15
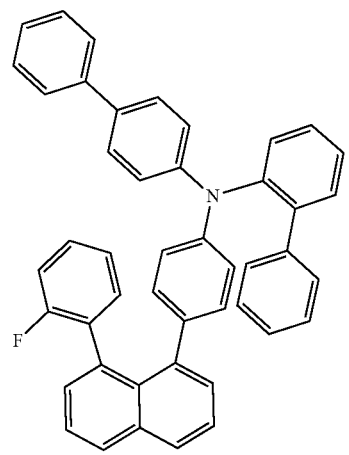
16
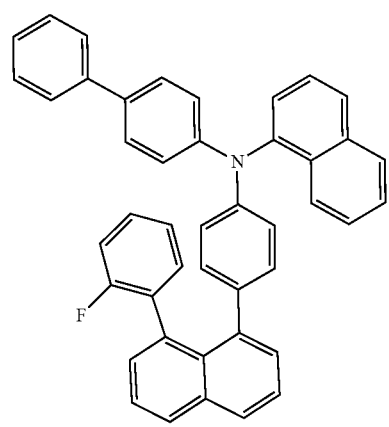
17
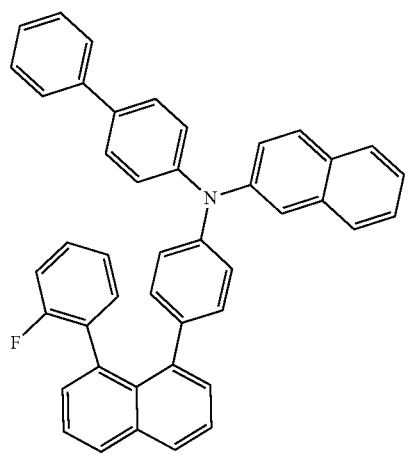
18
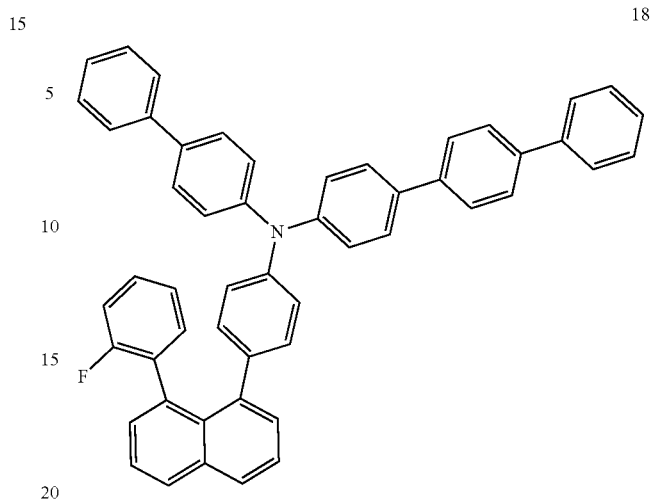
19
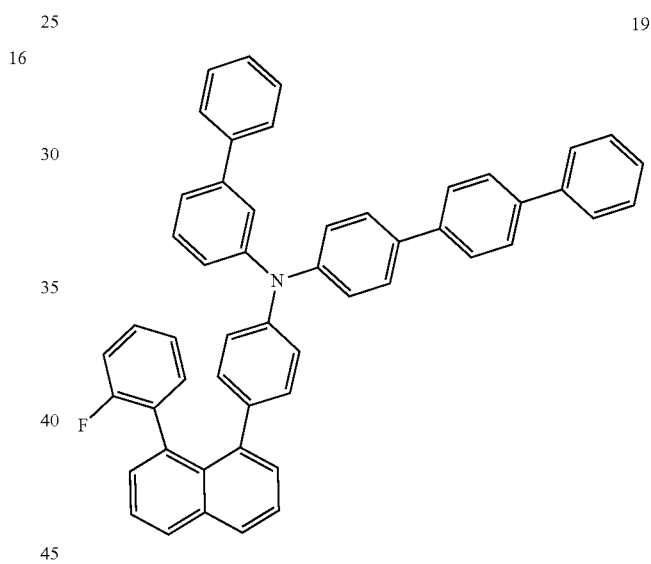
20
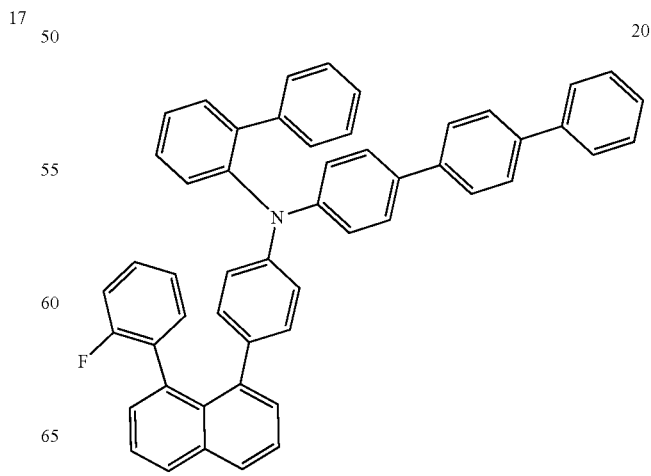

21
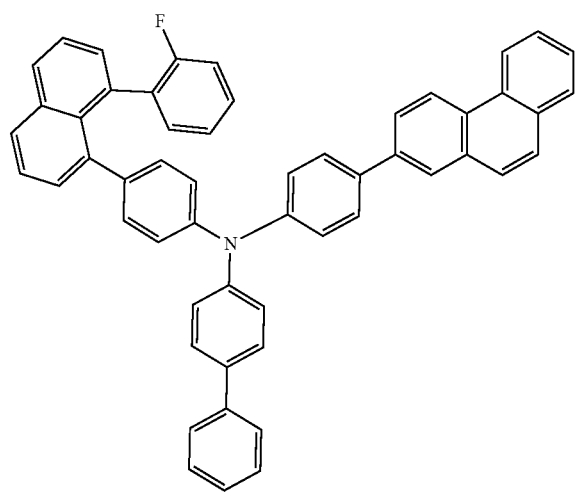
22
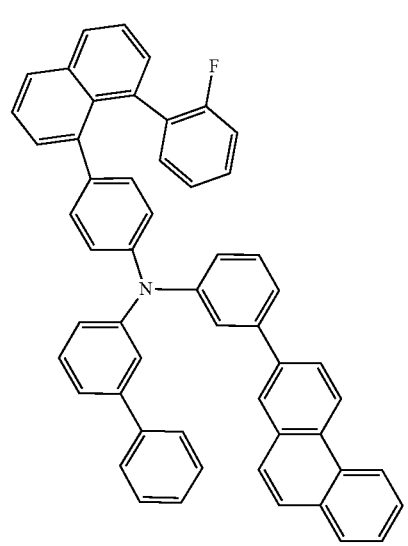
23
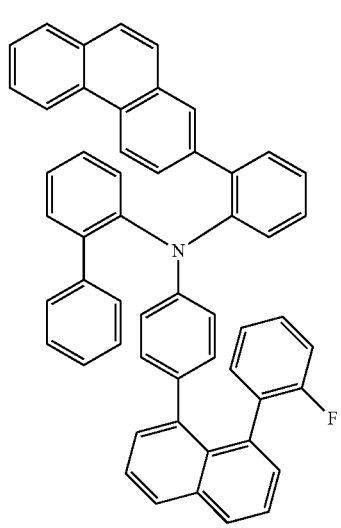
24
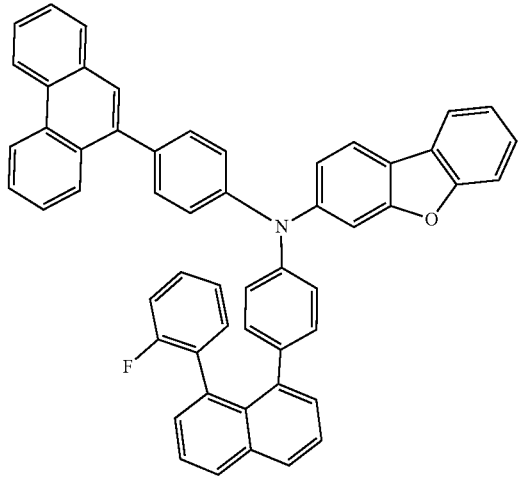
25
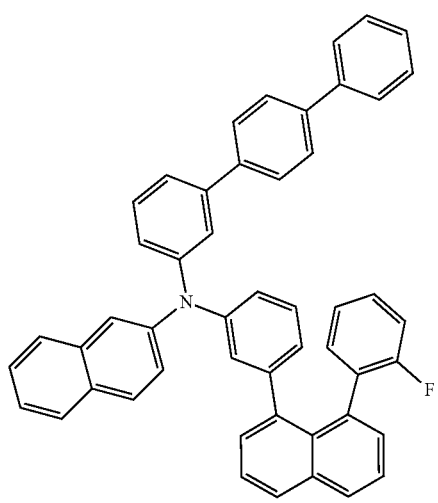
26
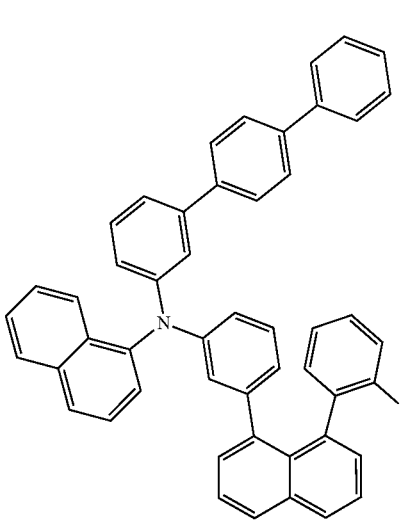

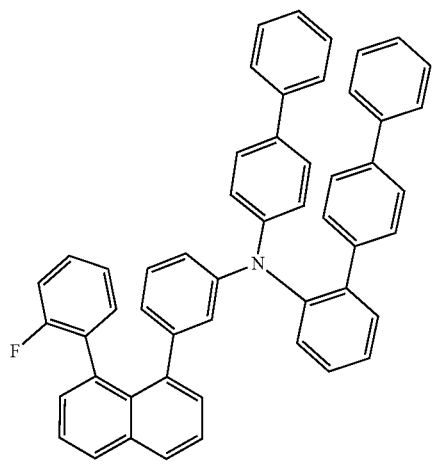
27
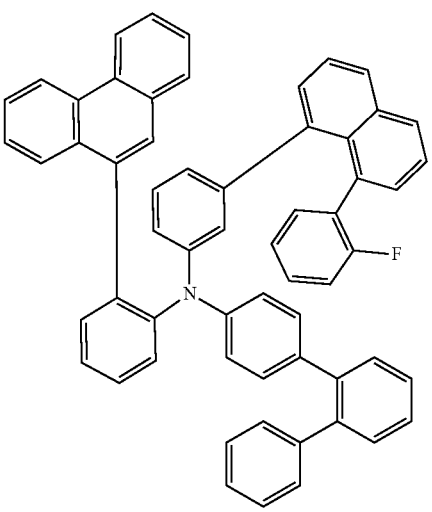
30
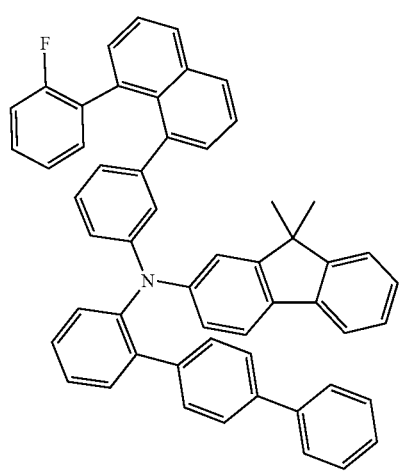
28
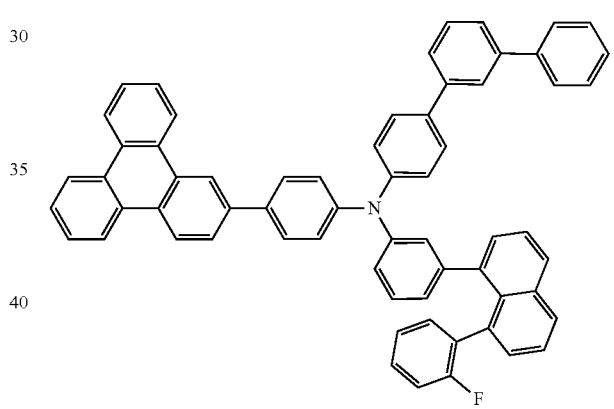
31
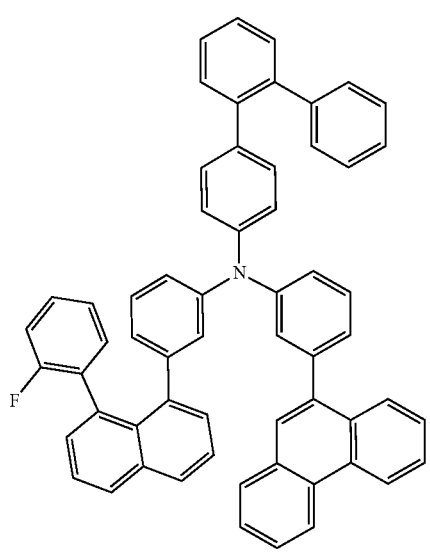
29
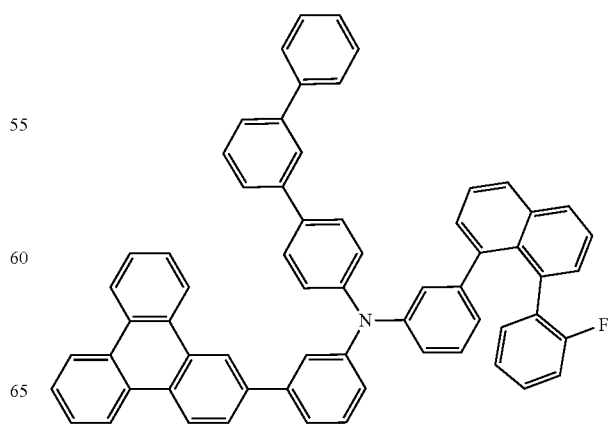
32

-continued
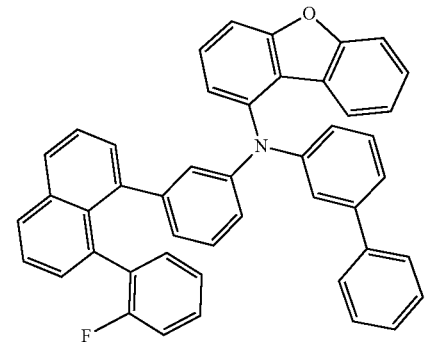
33
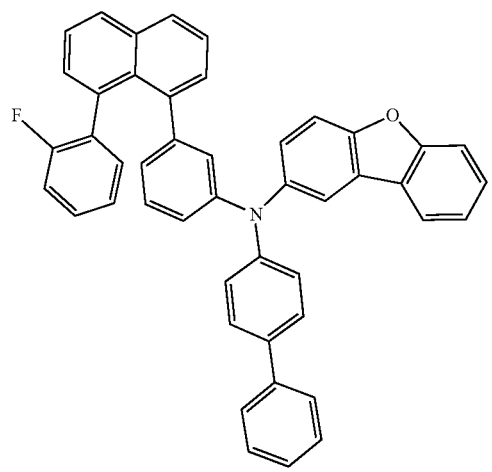
34
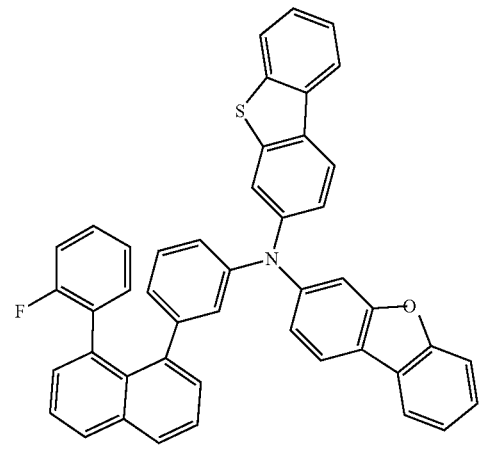
35
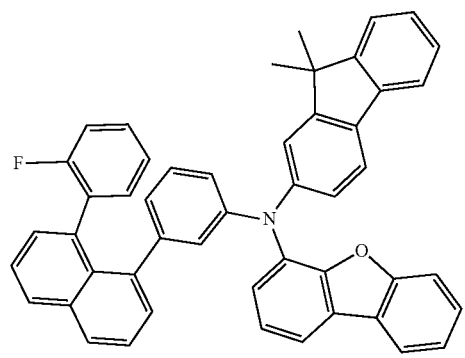
36
-continued
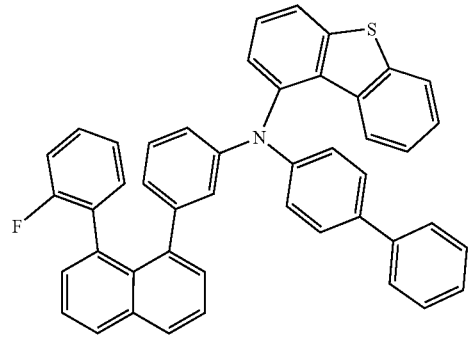
37
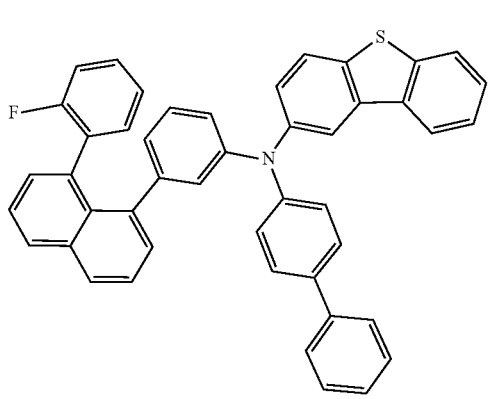
38
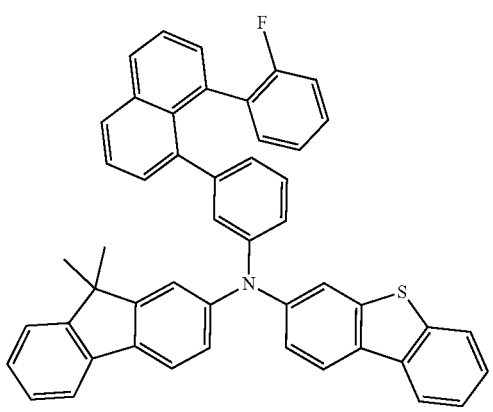
39
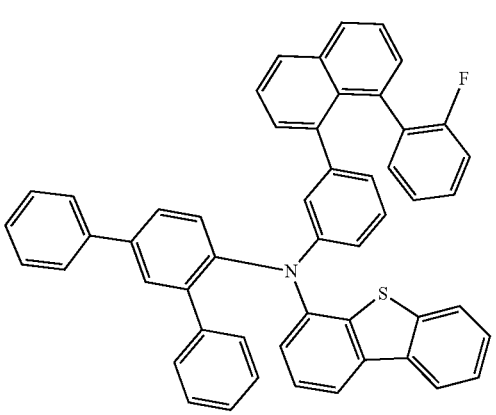
40

41
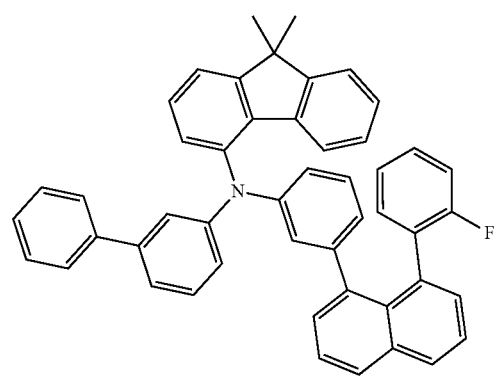
42
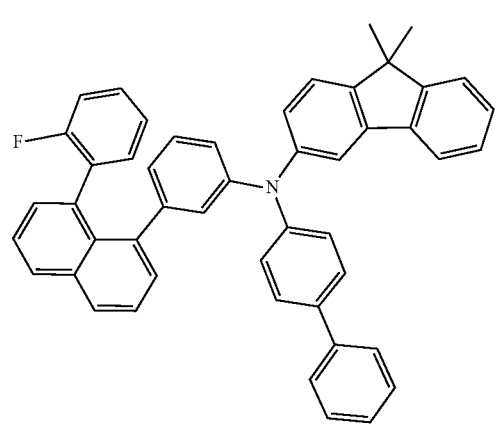
43
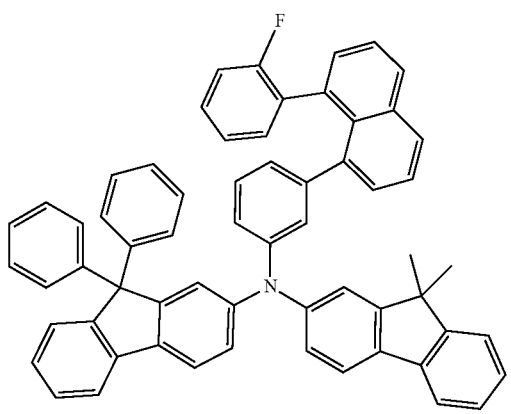
44
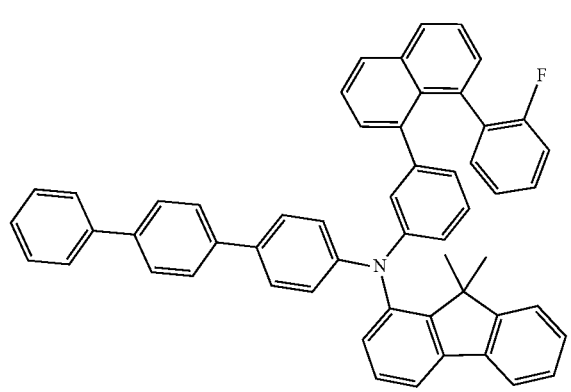
45
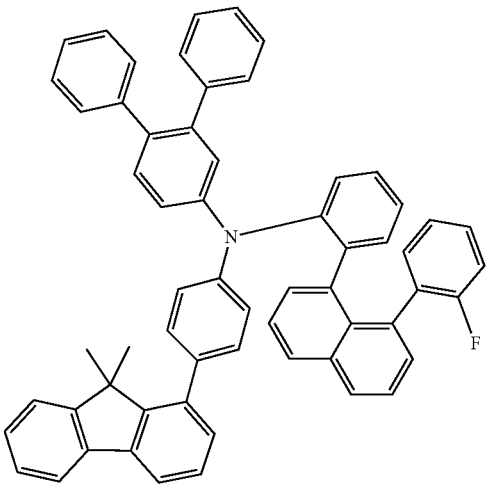
46
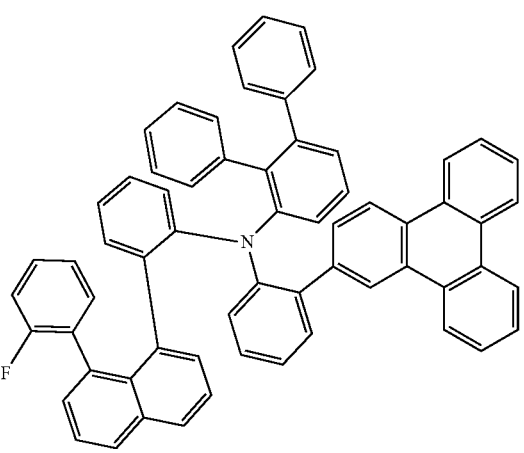
47
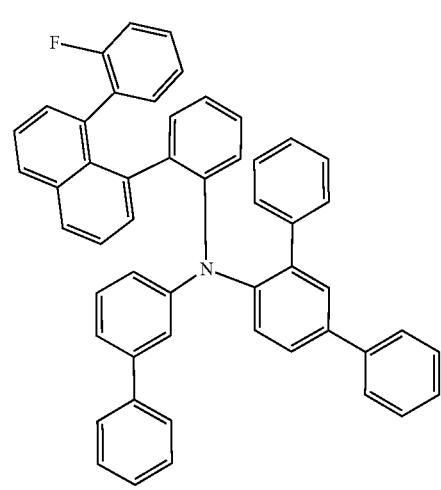

48
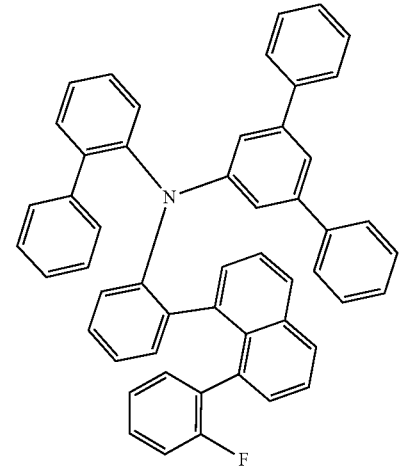
49
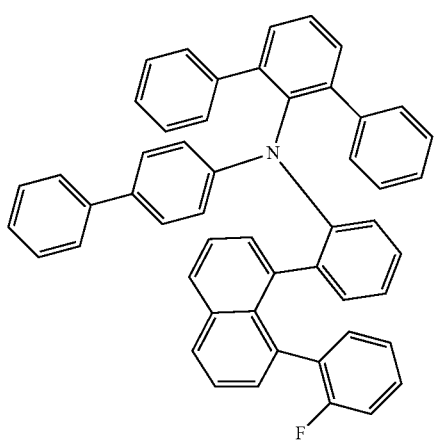
50
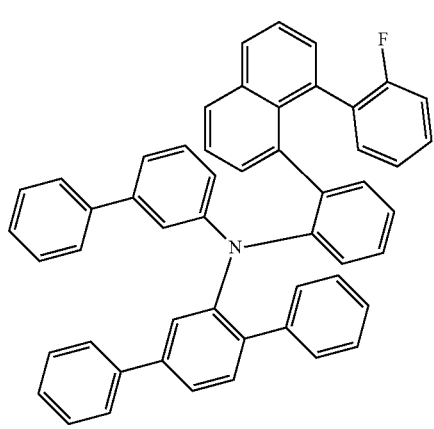
51
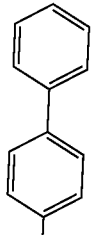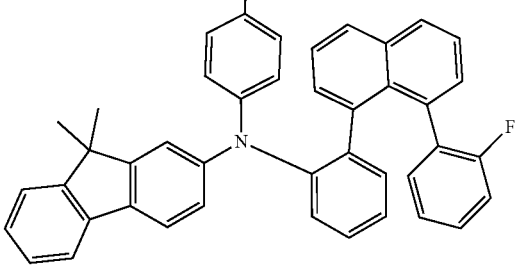
52
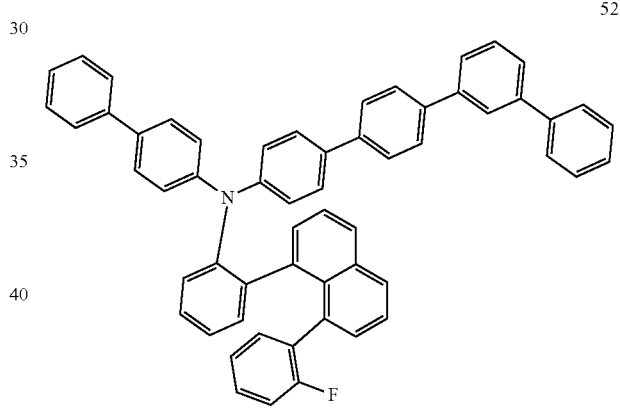
53
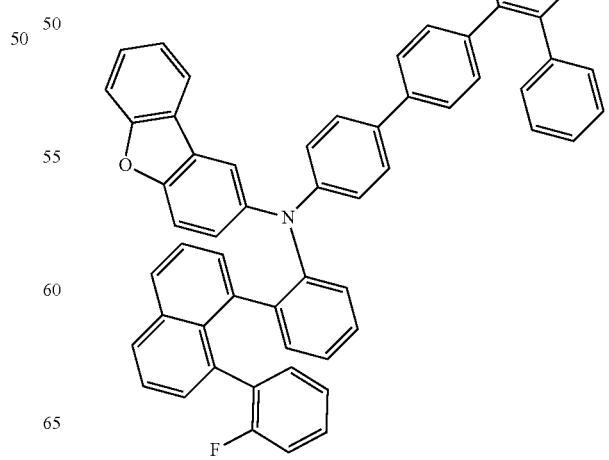

54
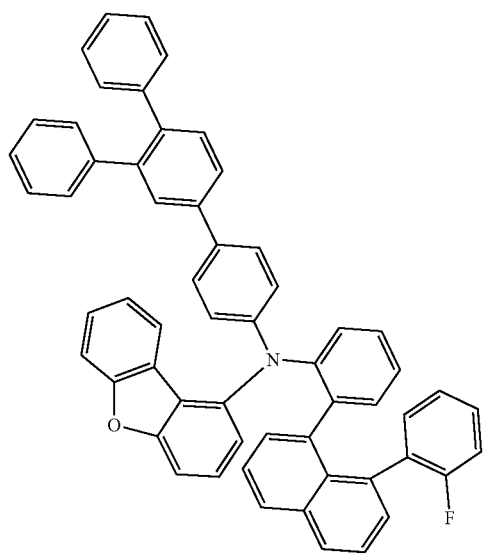
55
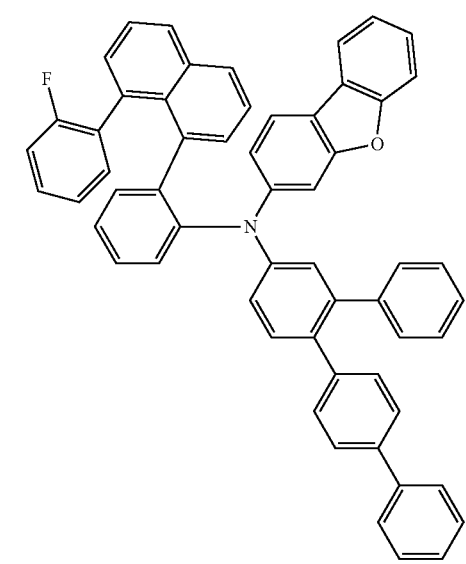
56
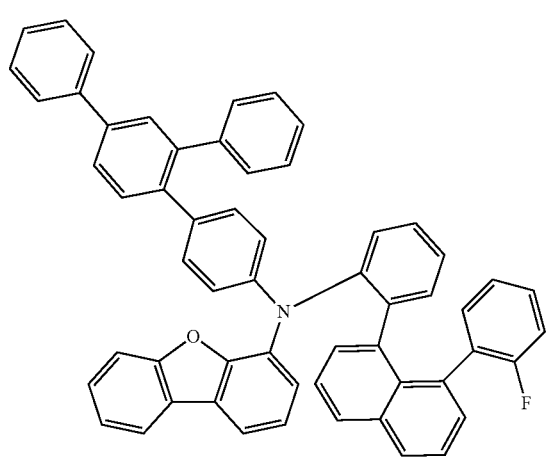
57
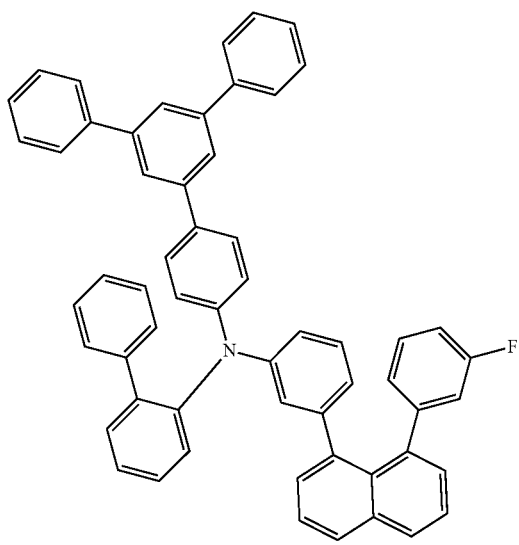
58
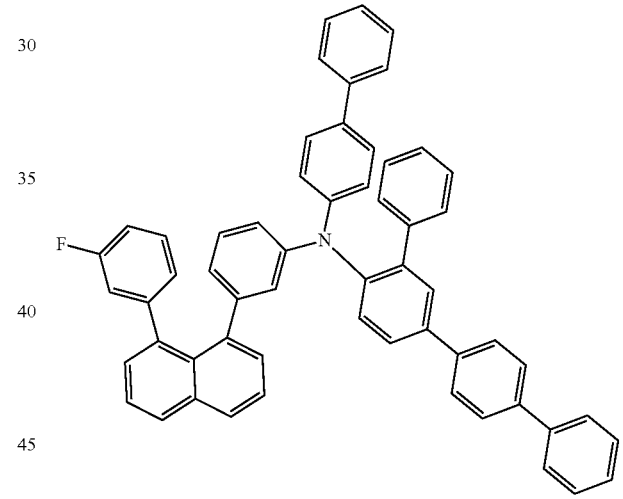
59
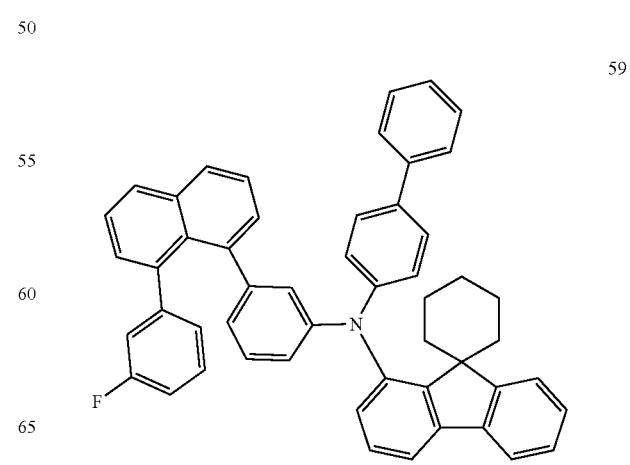

-continued
60
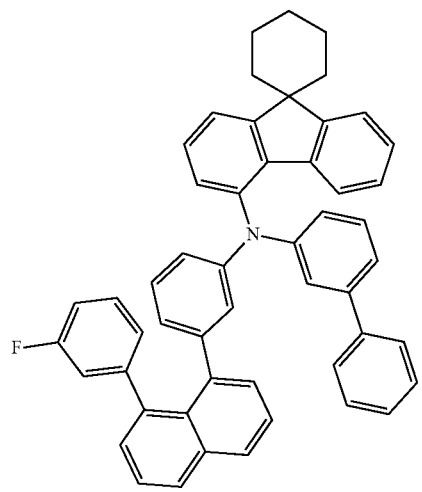
61
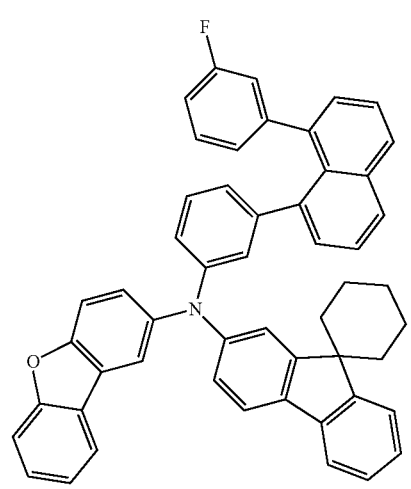
62
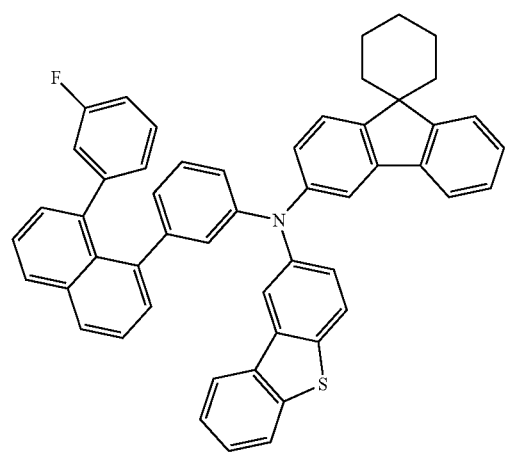
-continued
63
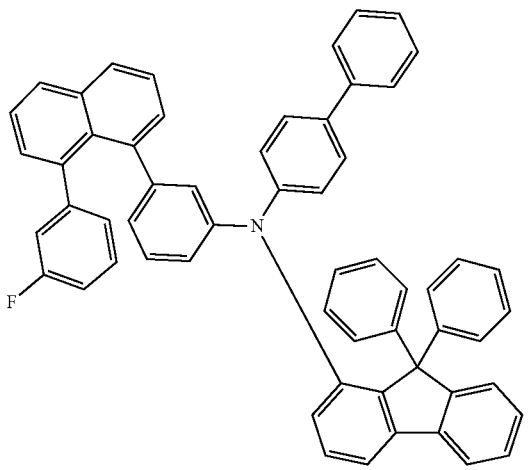
64
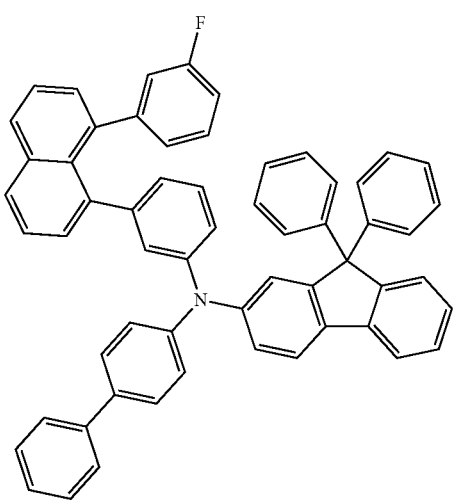
65
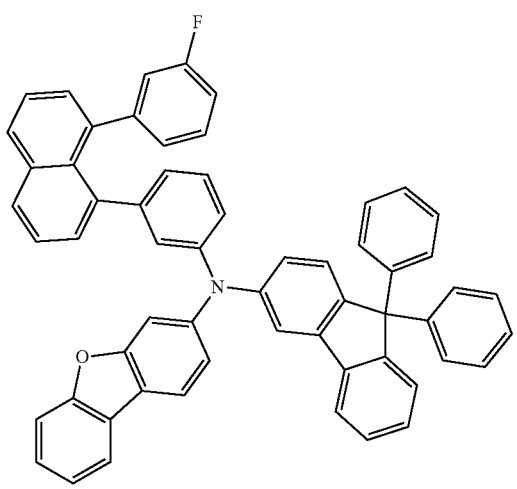

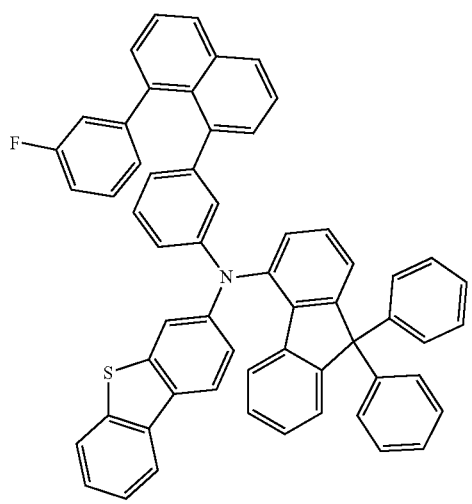
66
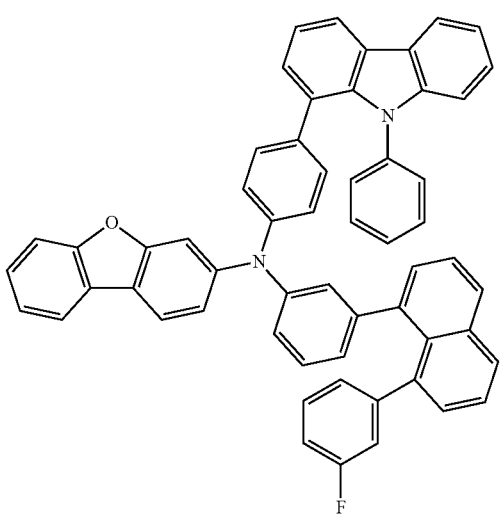
69
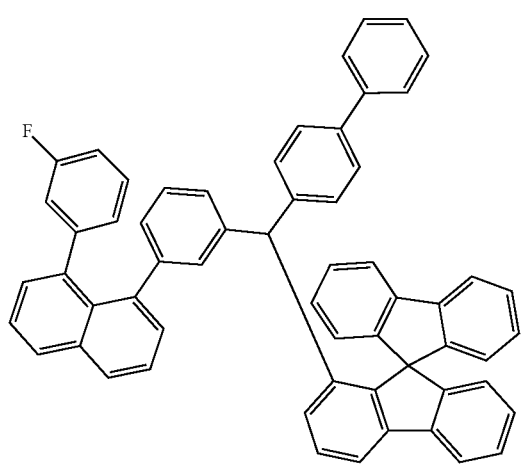
67
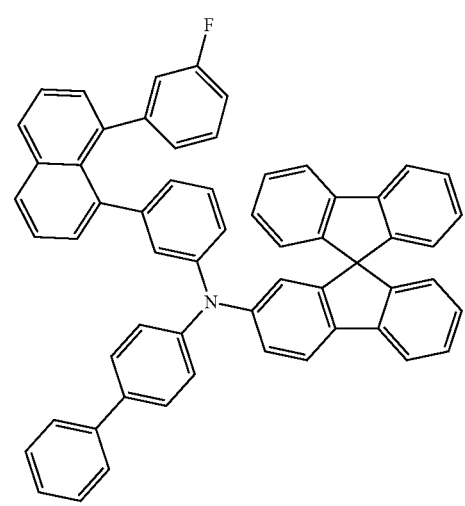
68
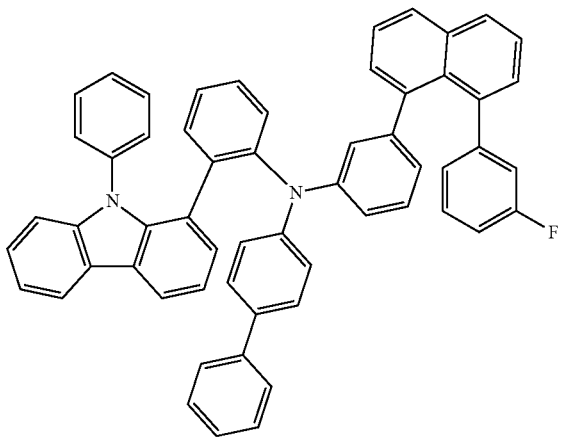
70
71

72
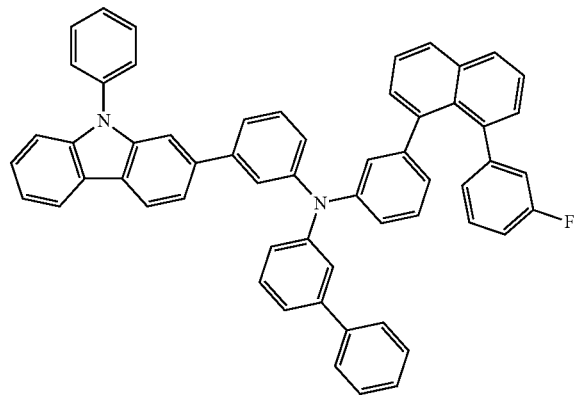
73
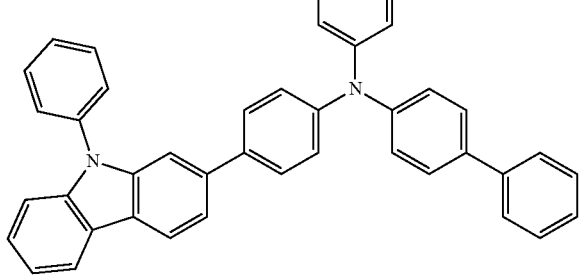
74
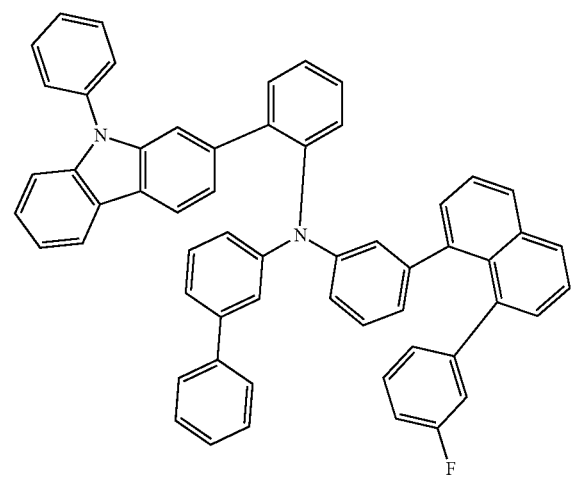
75
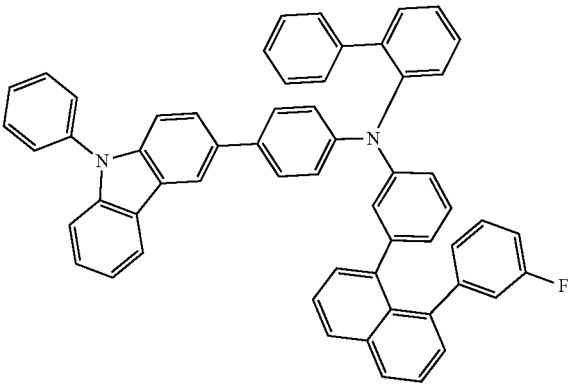
76
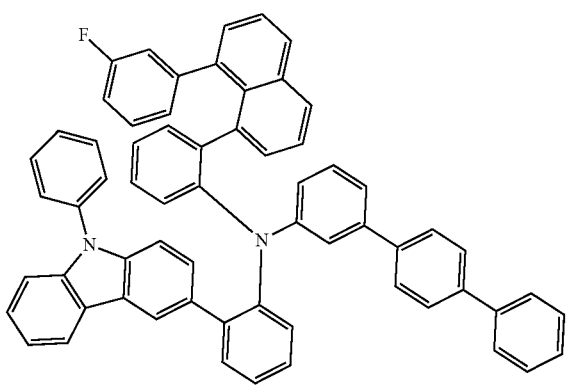
77
78
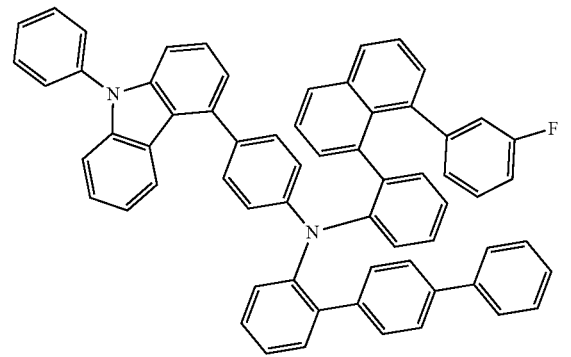

79
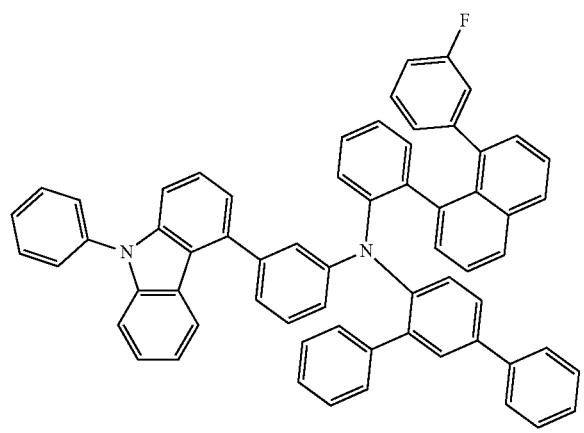
80
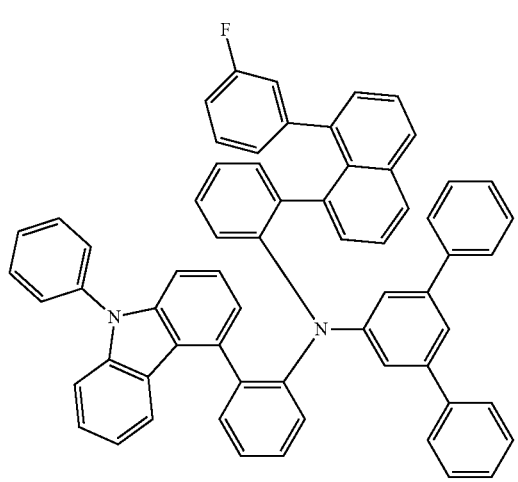
81
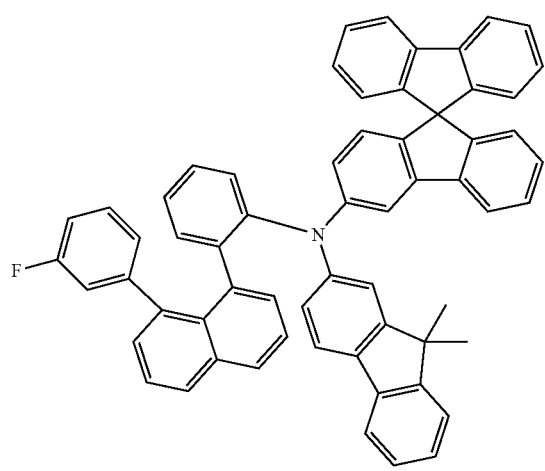
82
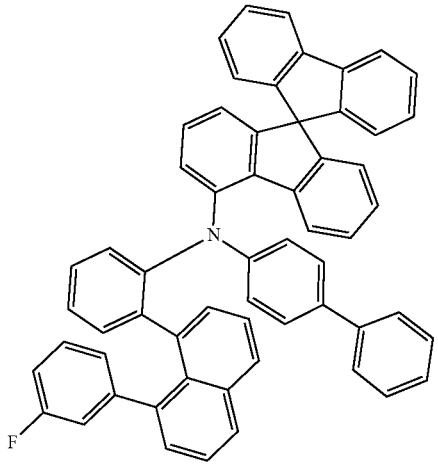
83
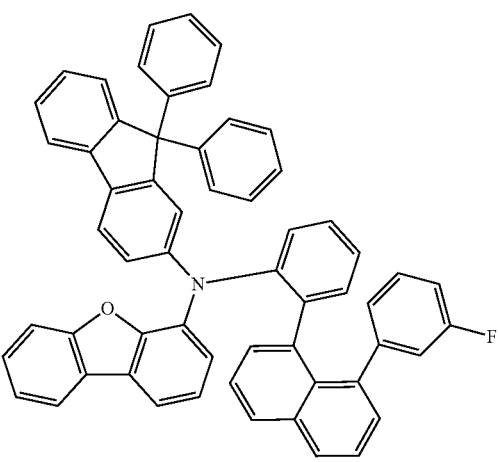
84
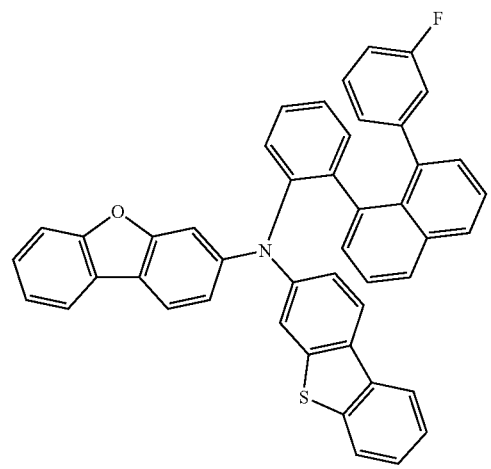

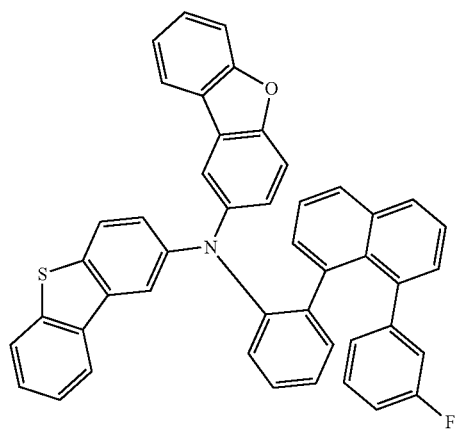
85
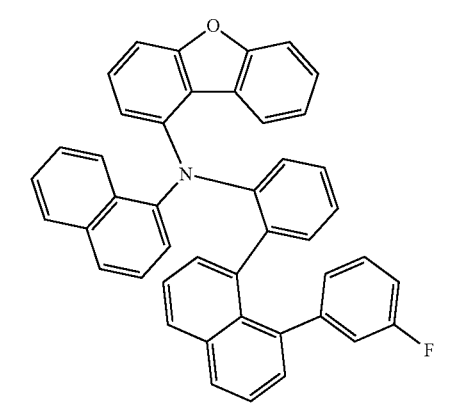
86
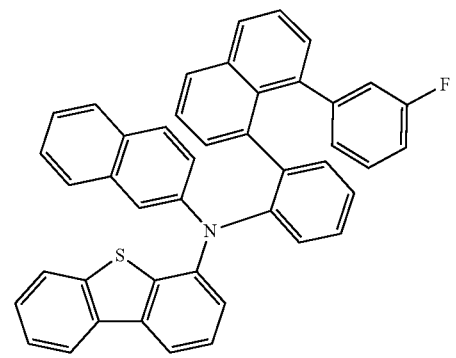
87
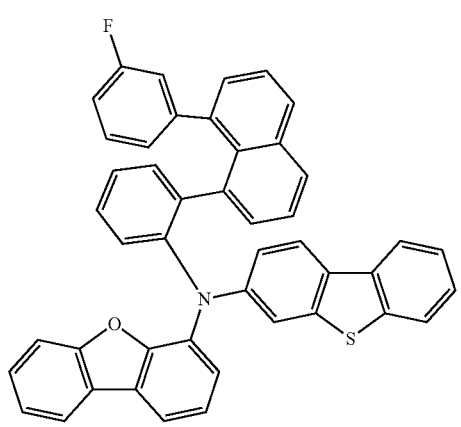
88
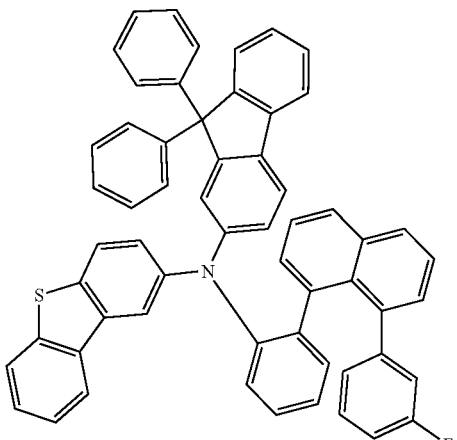
89
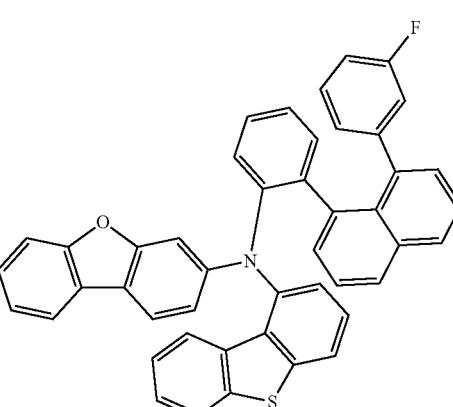
90
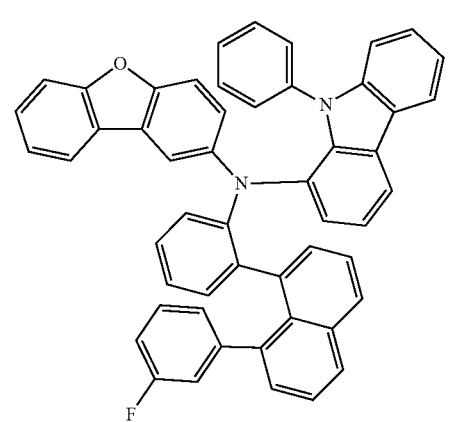
91

92
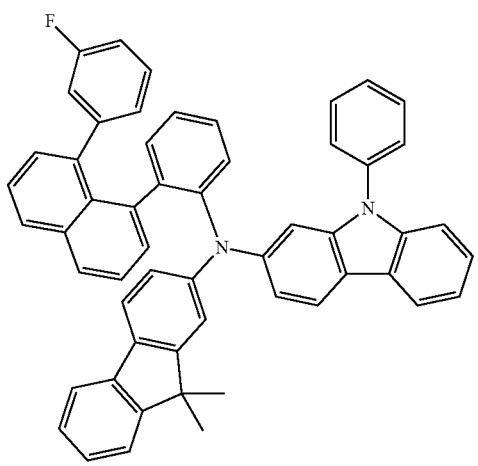
95
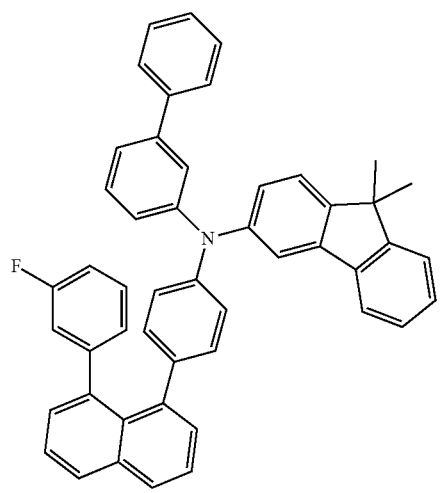
93
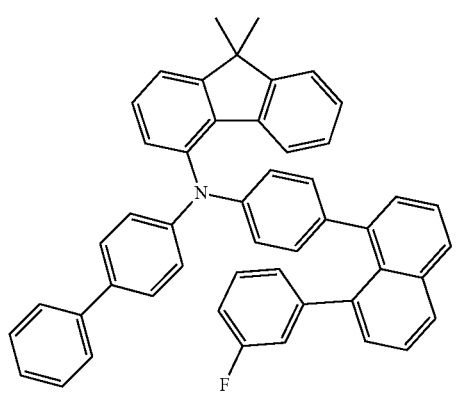
96
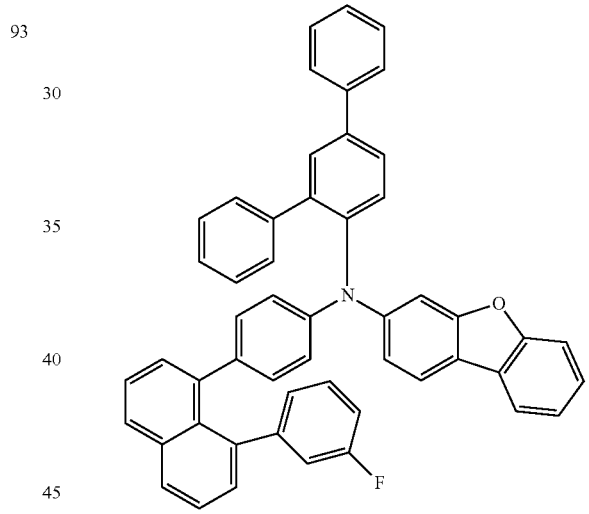
94
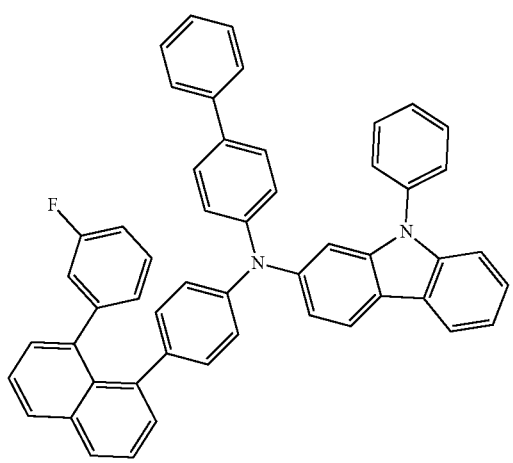
97
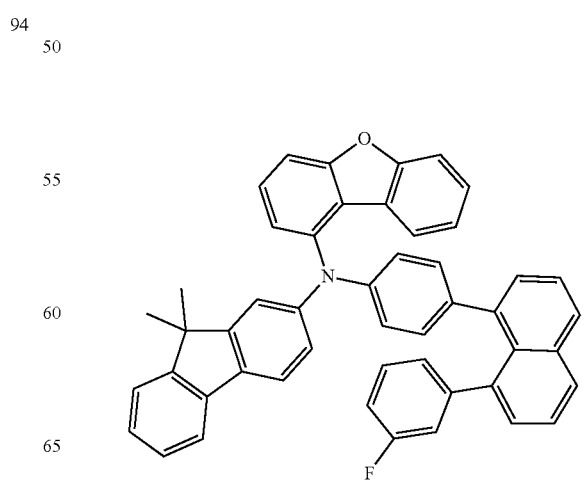

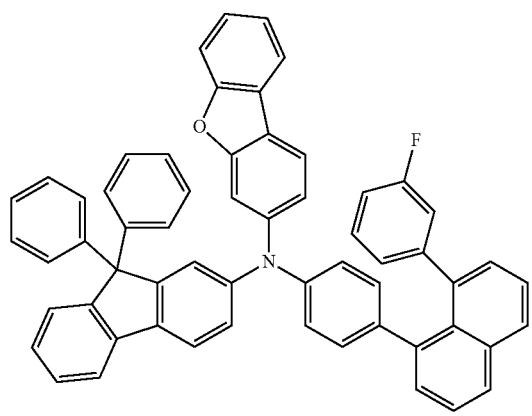
98
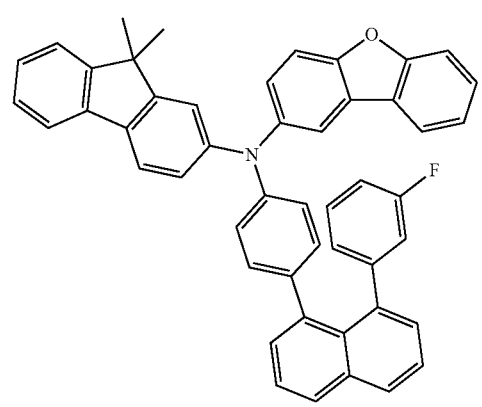
99
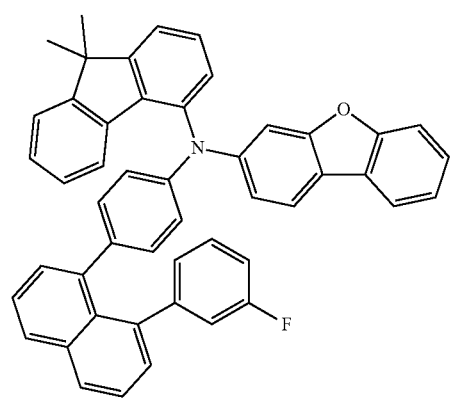
100
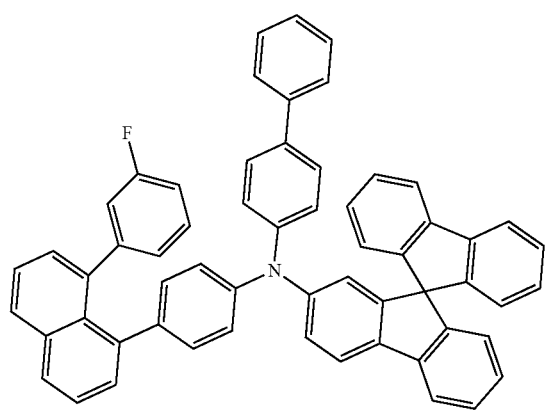
101
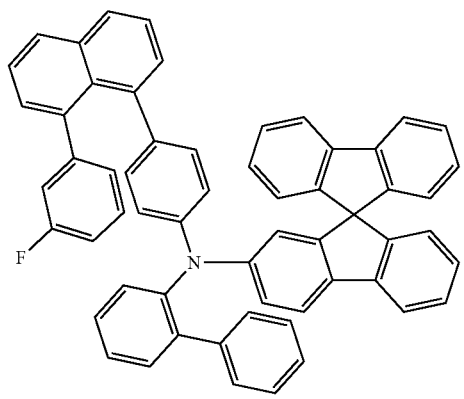
102
103
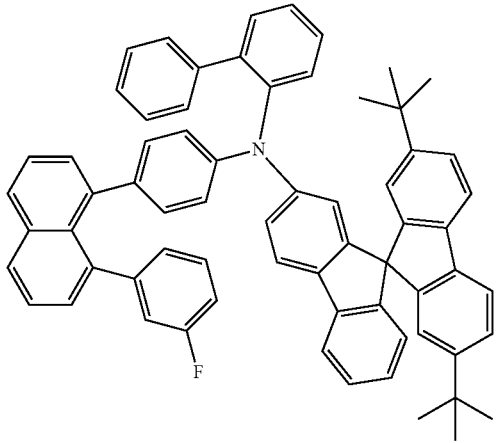
104

105
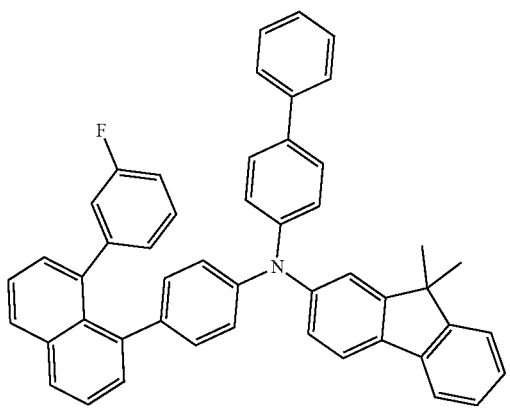
106
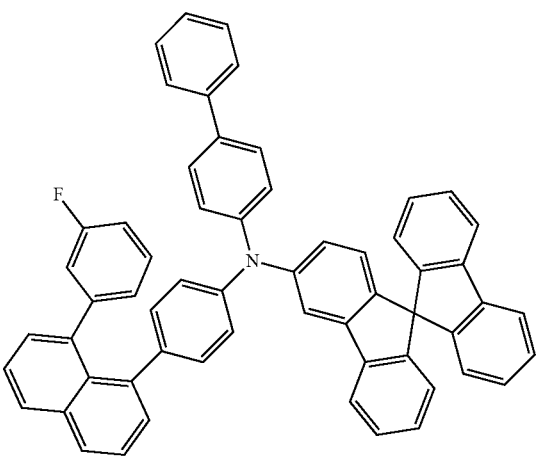
107
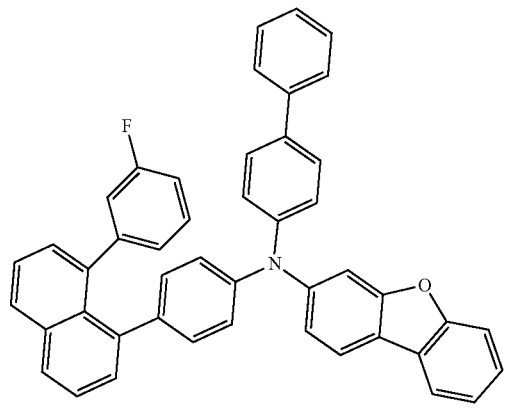
108
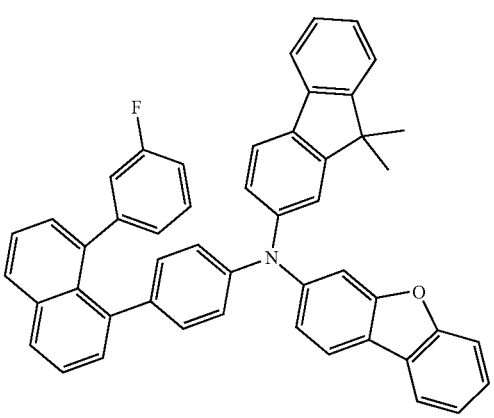
109
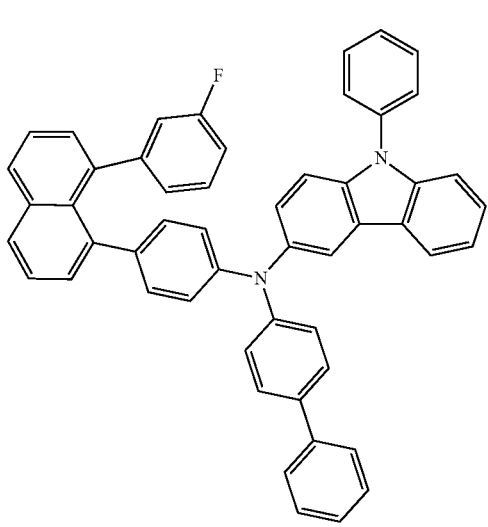
110
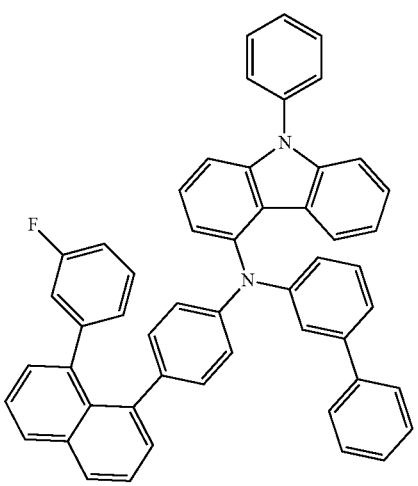

111
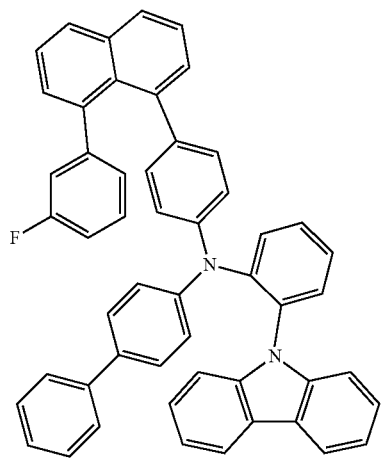
112
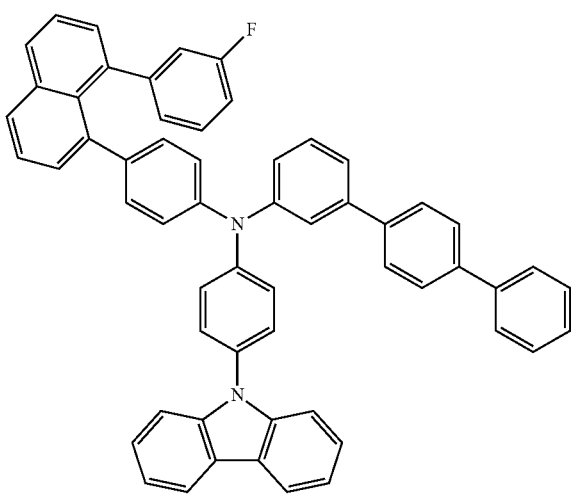
113
114
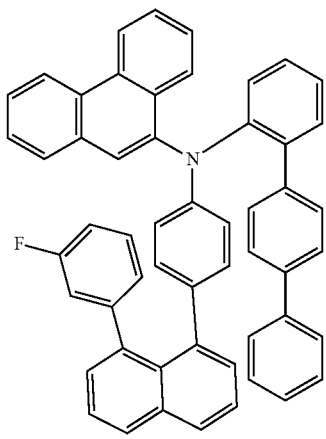
115
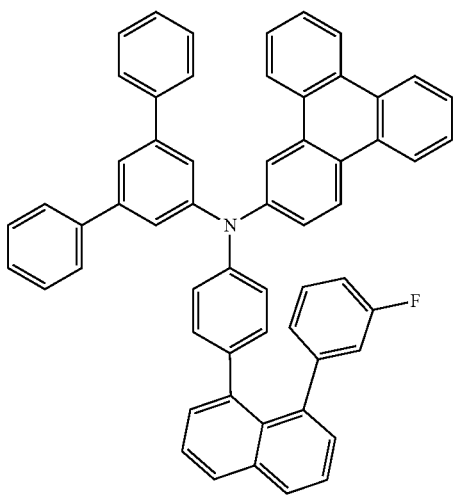
116

117
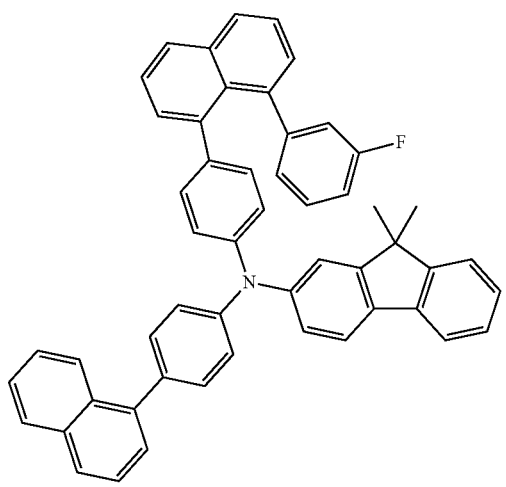
118
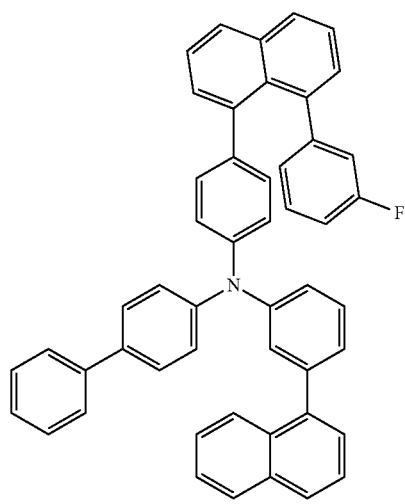
119
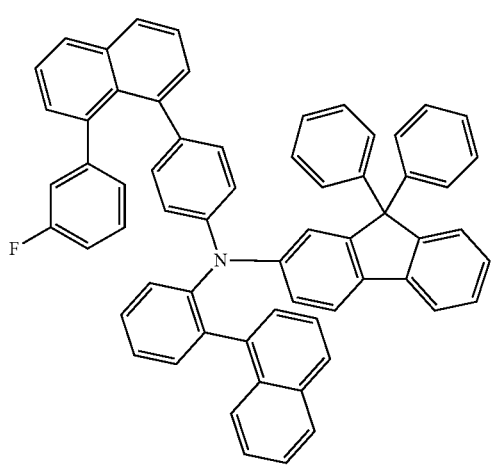
120
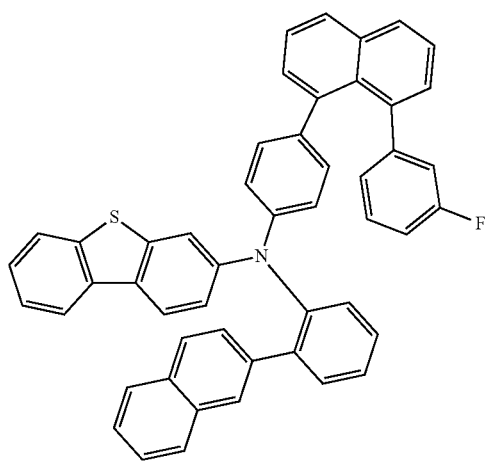
121
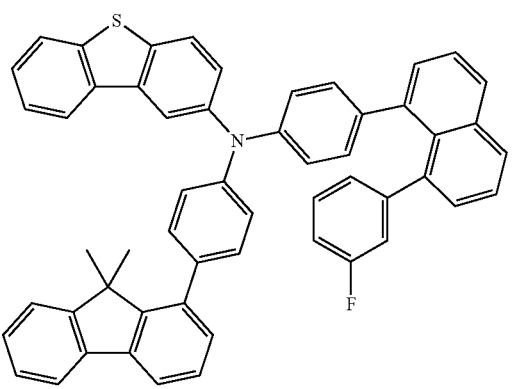
122
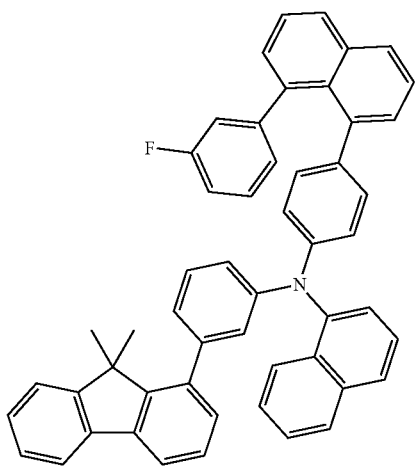

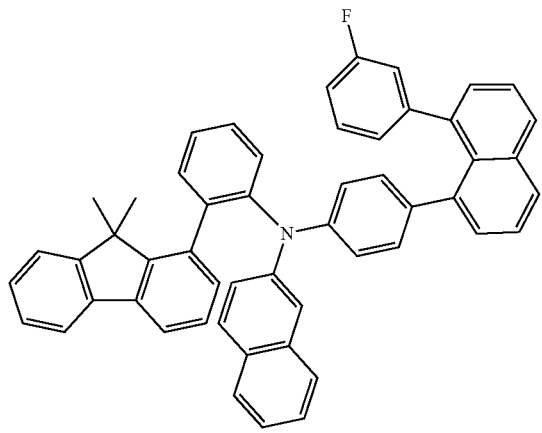
123
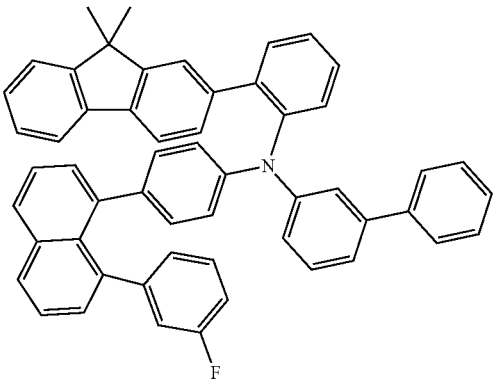
126
124
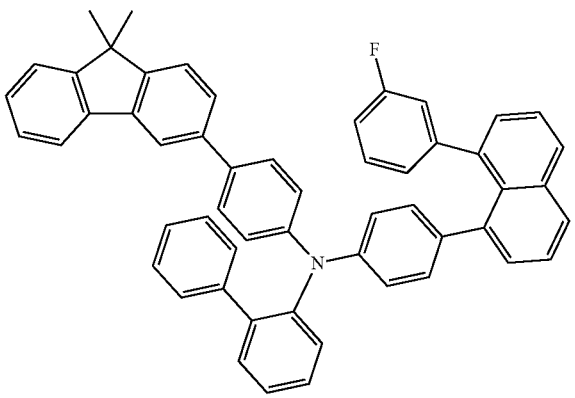
127
125
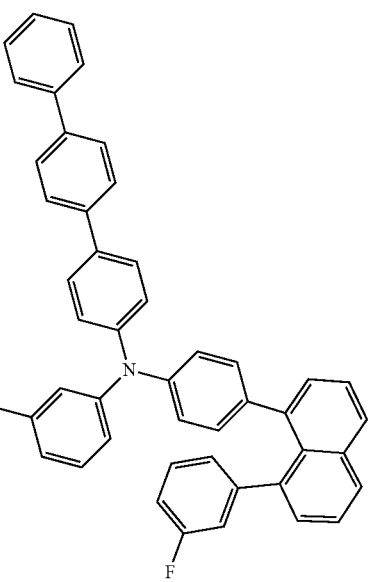
128

129
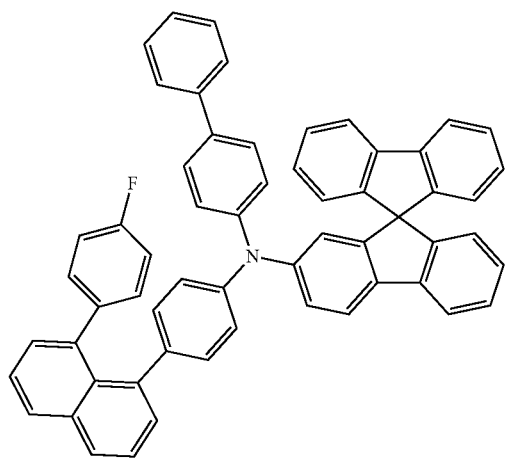
130
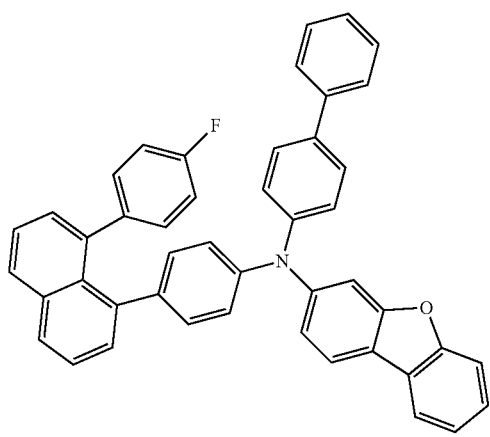
131
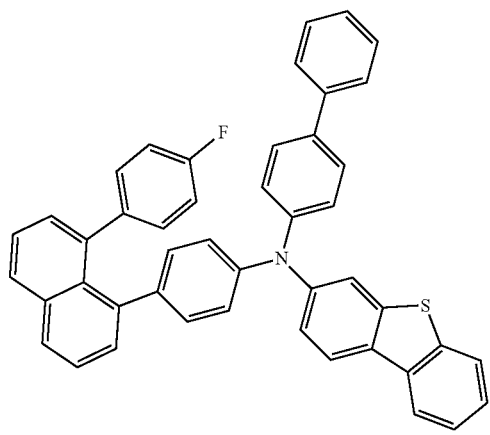
132
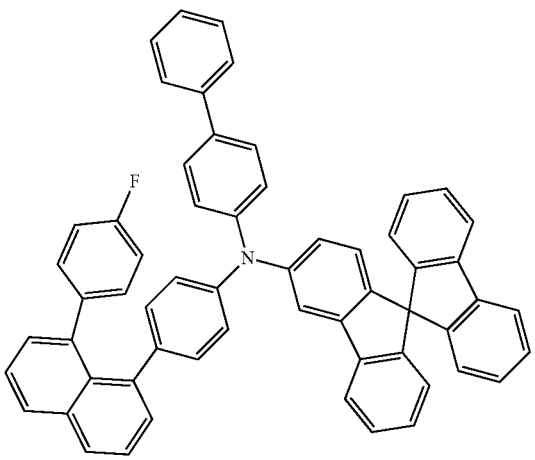
133
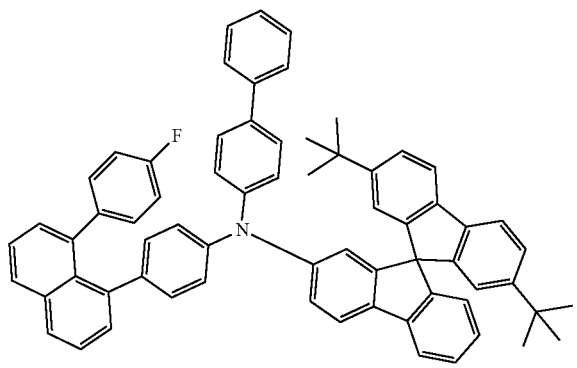
134
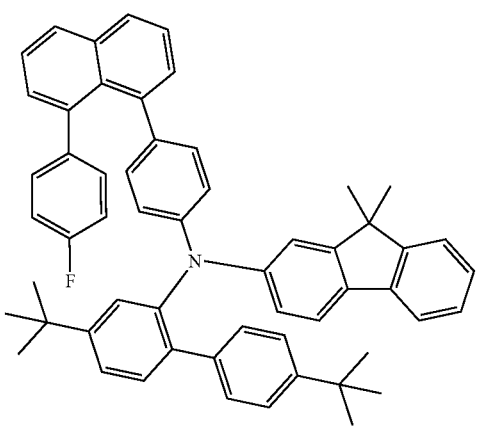

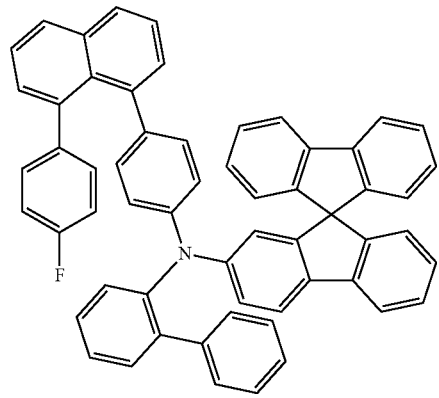
135
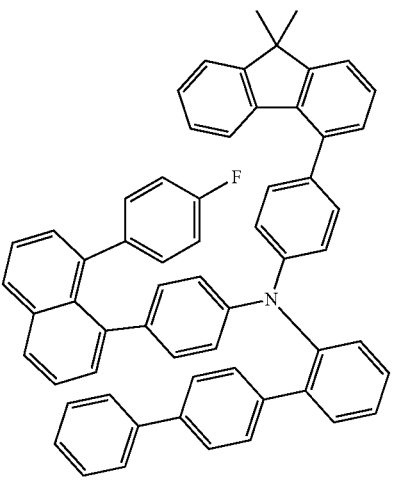
138
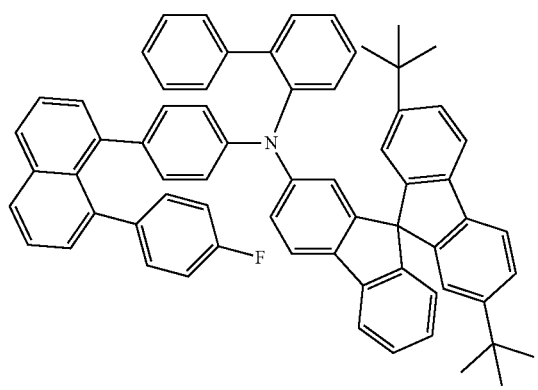
136
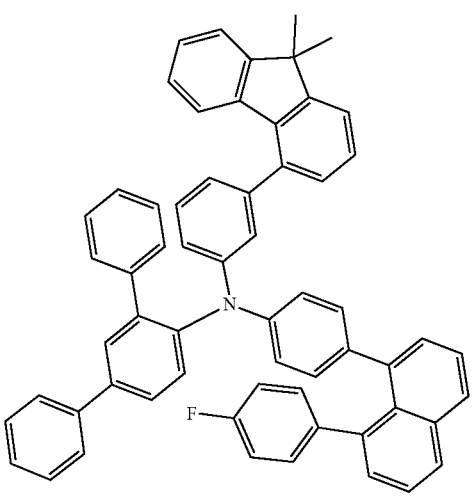
139
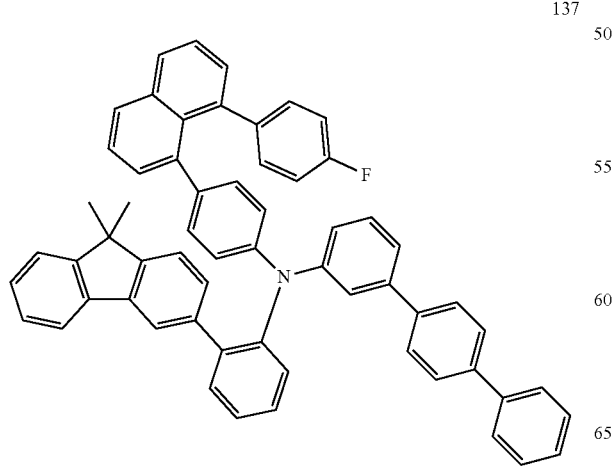
137
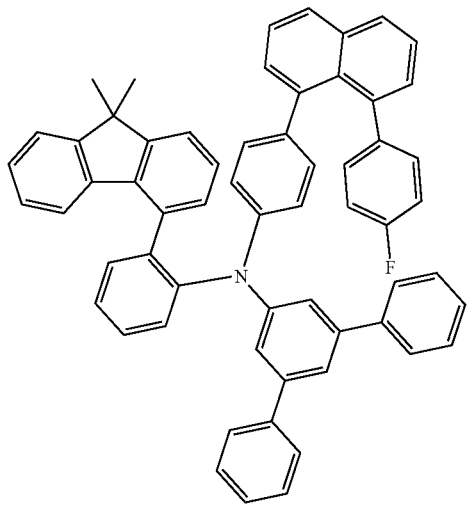
140

141
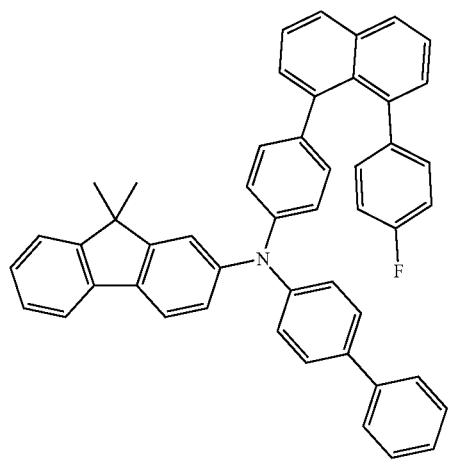
142
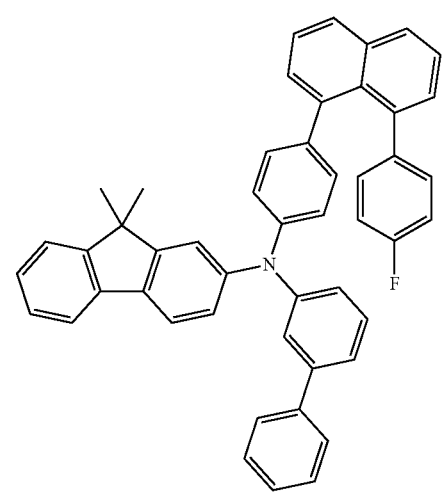
143
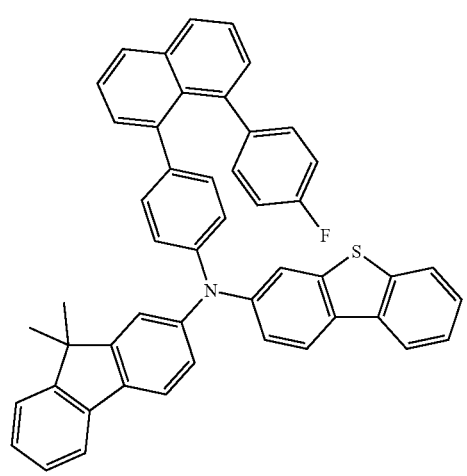
144
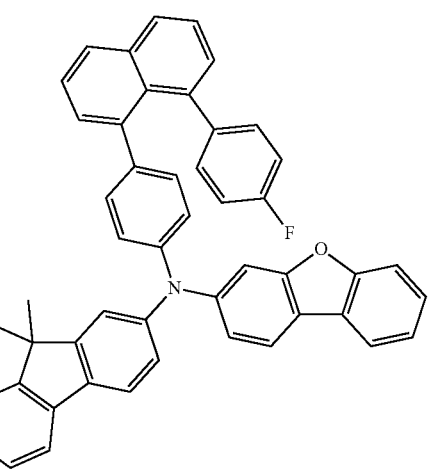
145
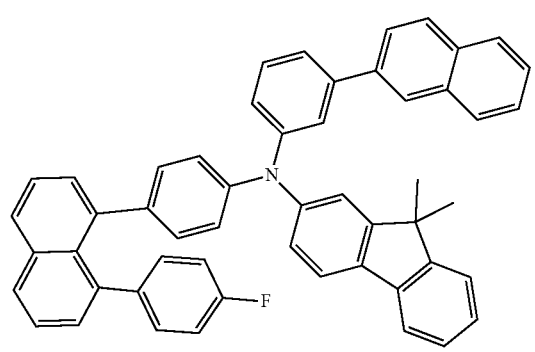
146
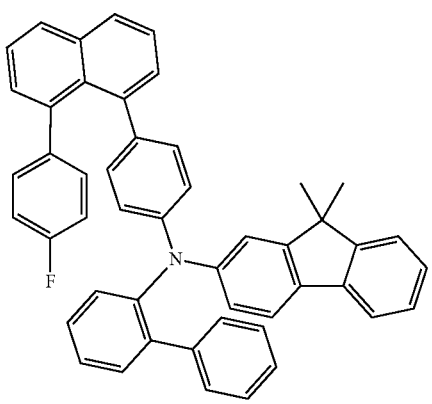
147
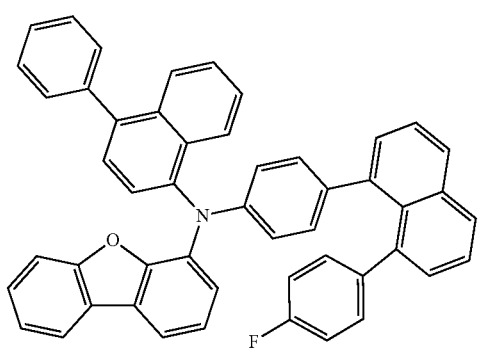

148
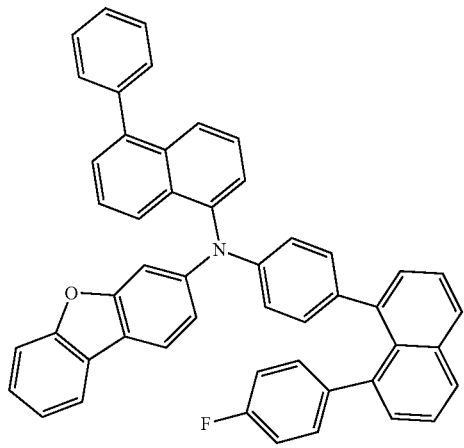
149
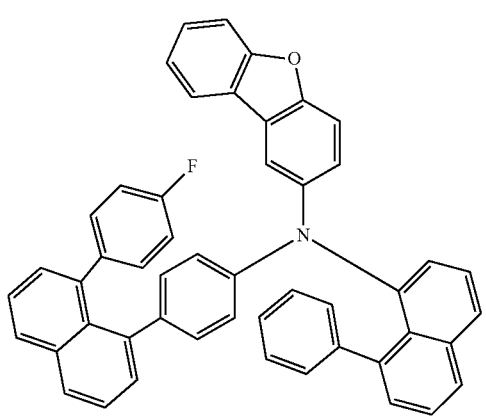
150
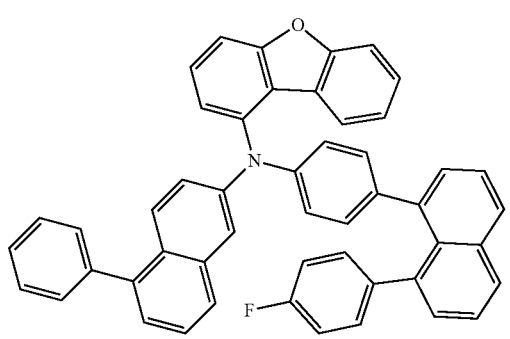
151
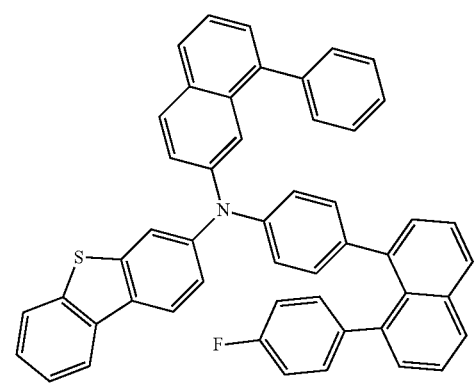
152
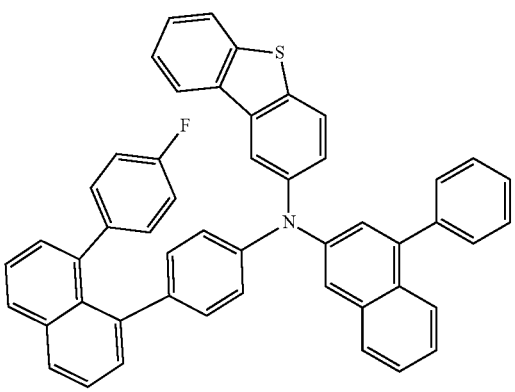
153
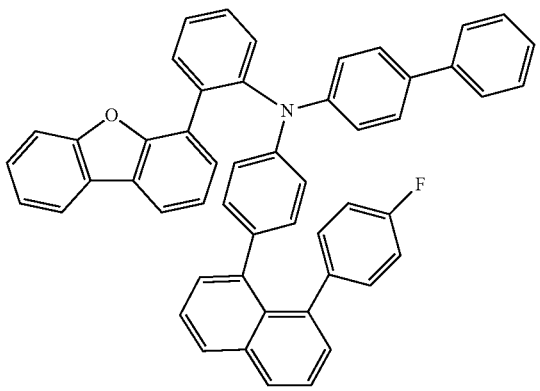
154
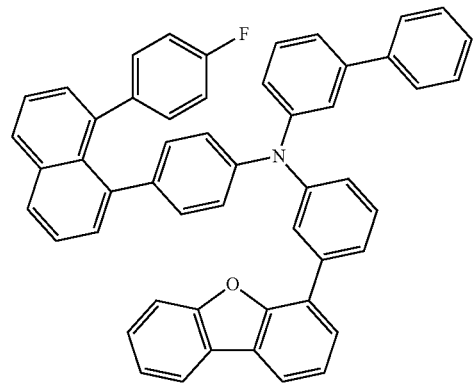

155
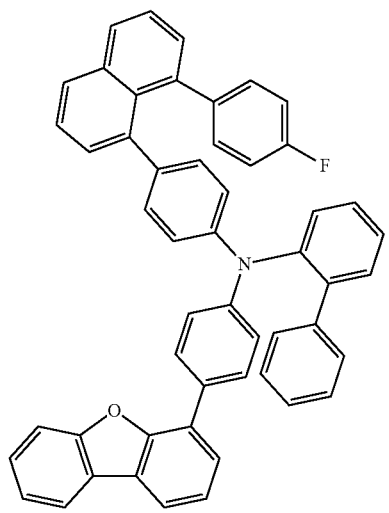
156
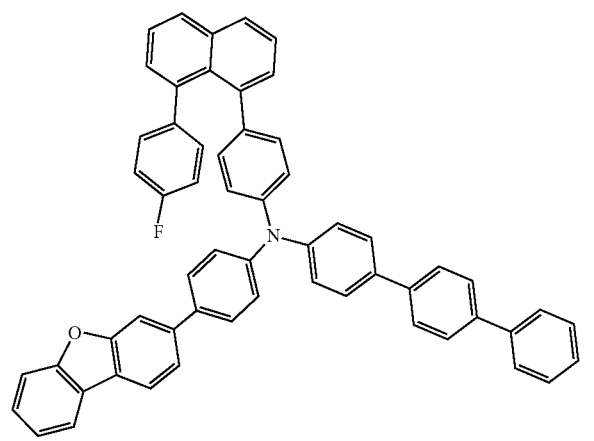
157
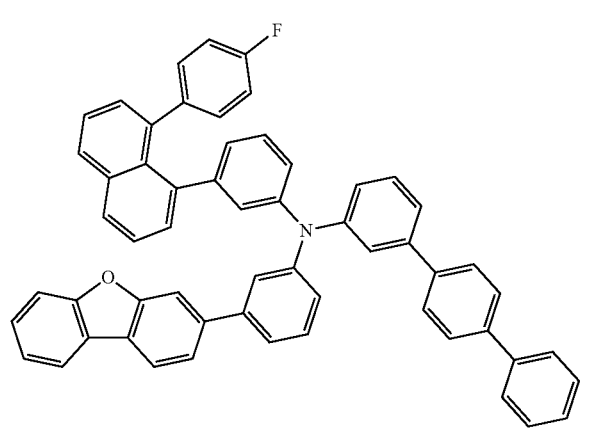
158
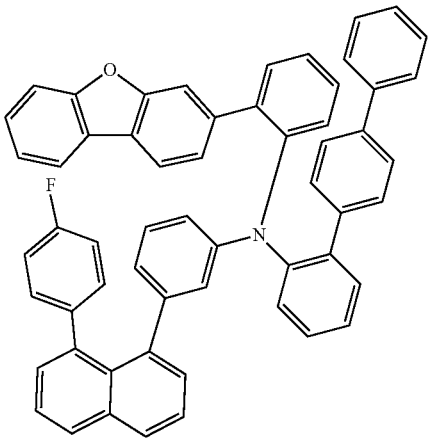
159
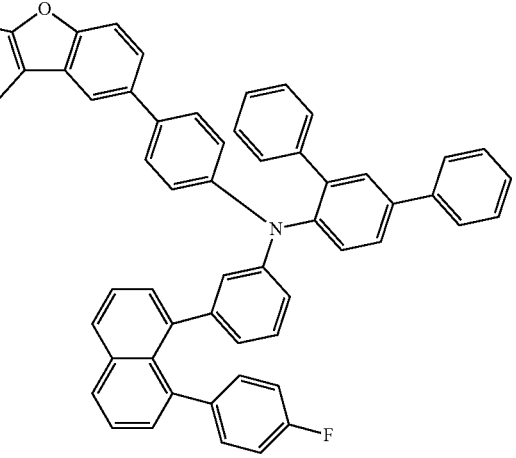
160
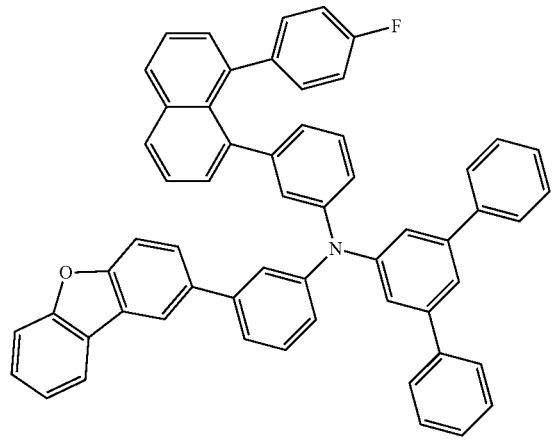

73
-continued
161
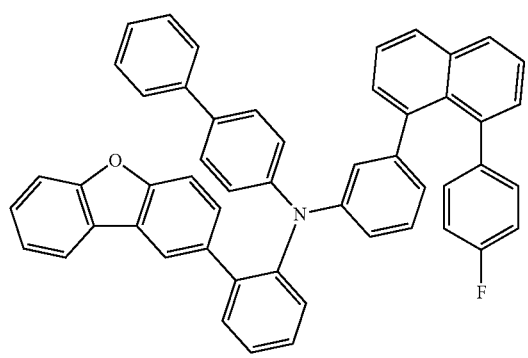
162
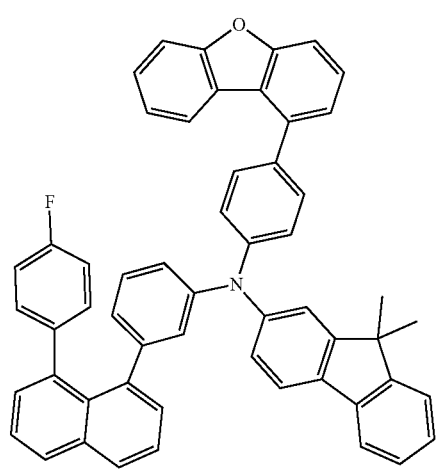
163
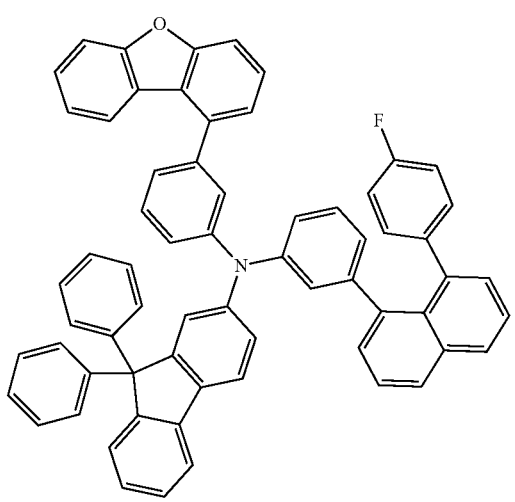
74
-continued
164
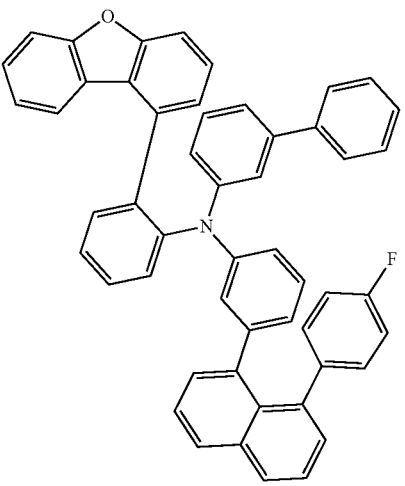
165
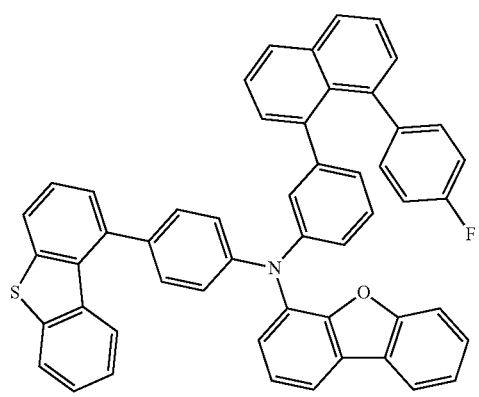
166
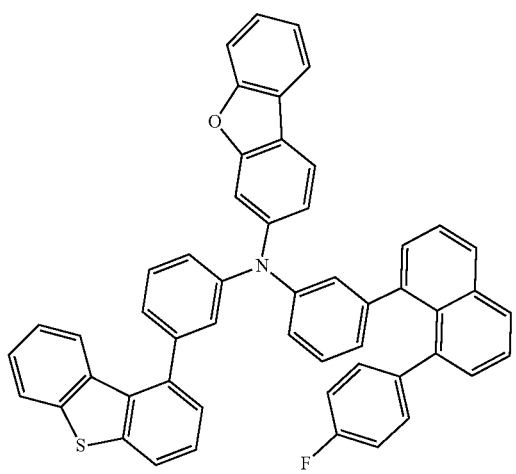

167
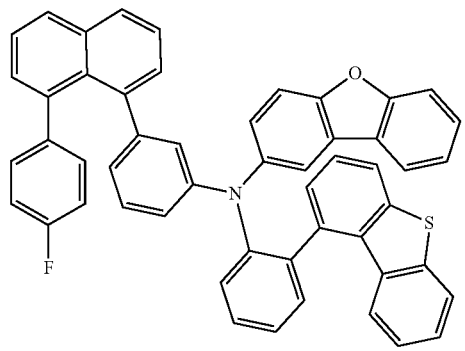
168
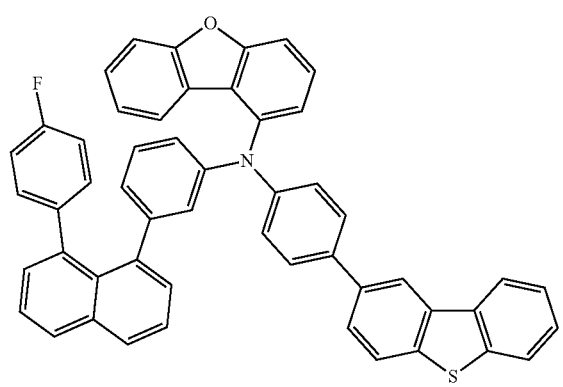
169
171
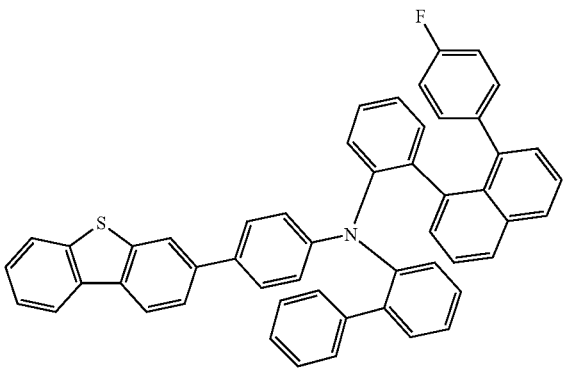
172
170
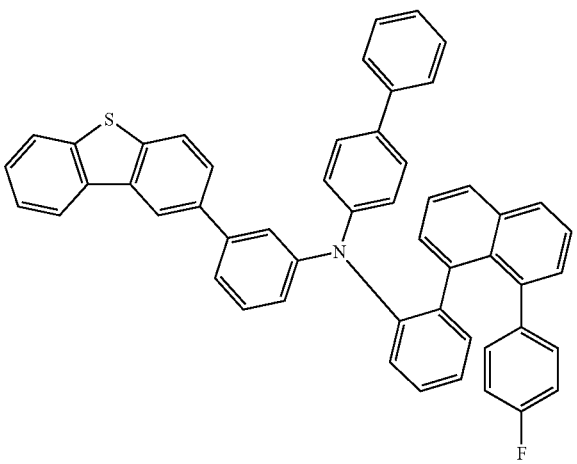
173

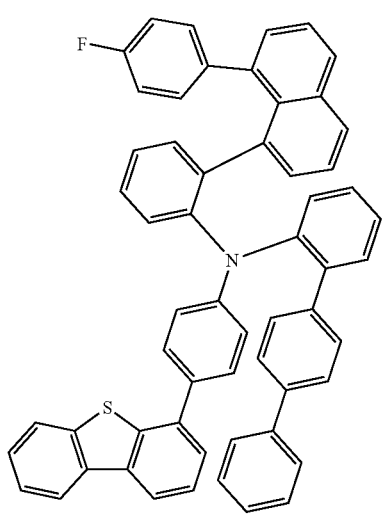
174
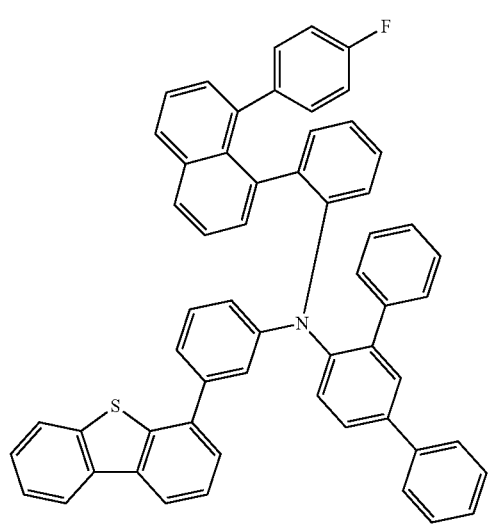
175
176
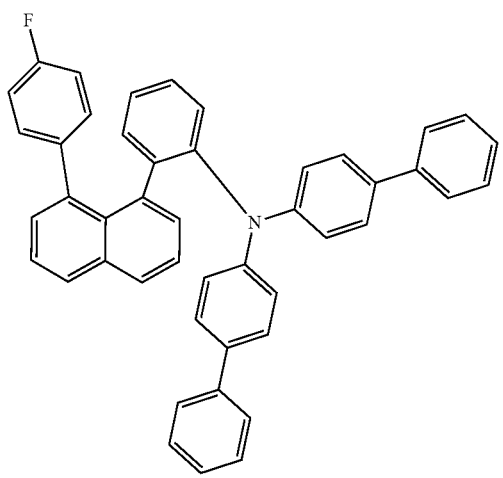
177
178
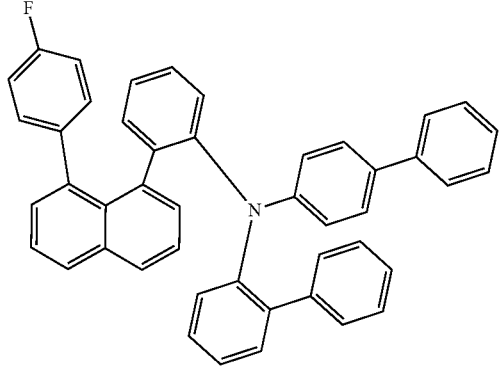
179

180
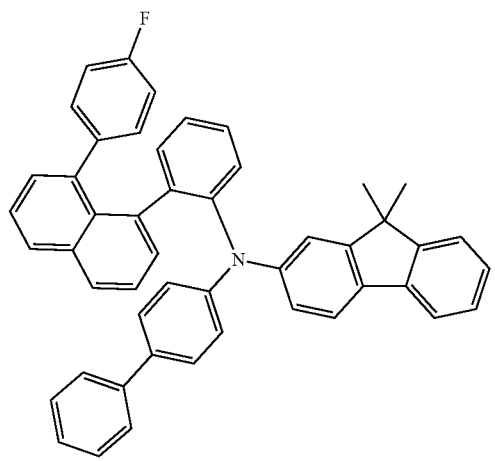
183
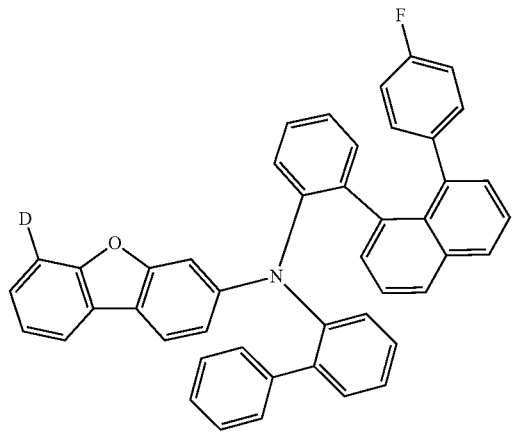
181
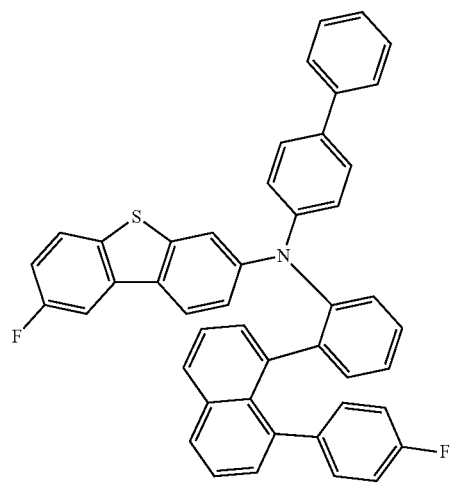
184
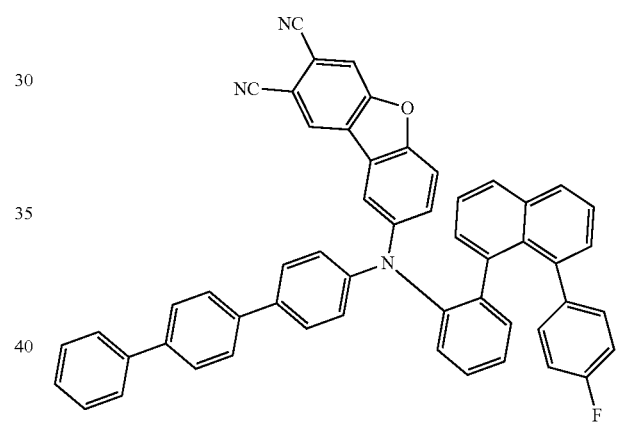
182
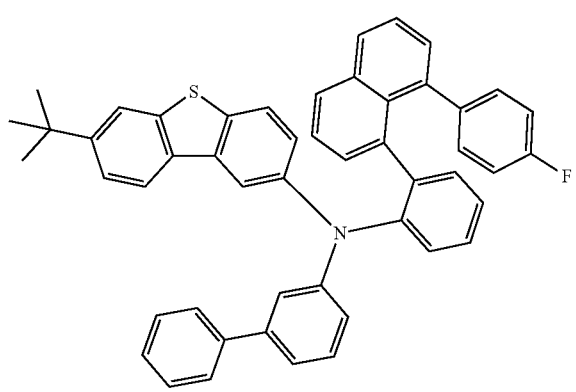
185
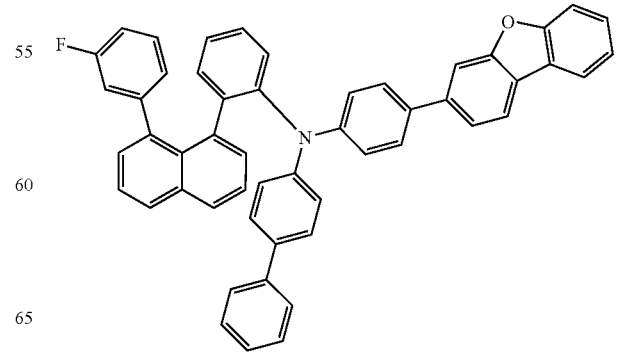

186
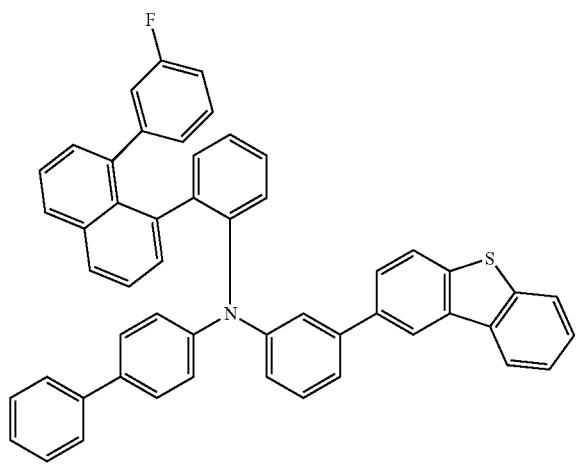
189
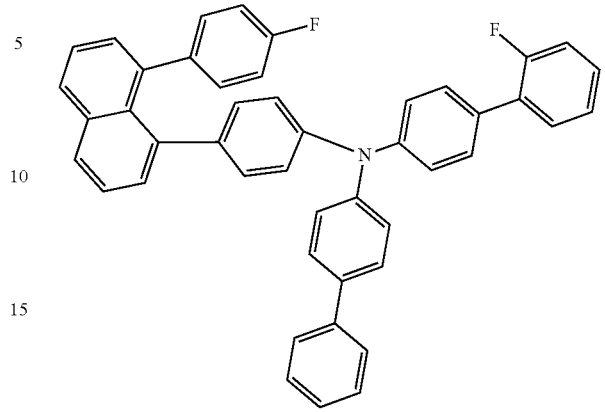
187
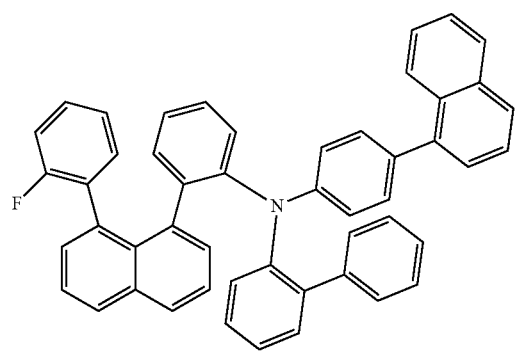
190
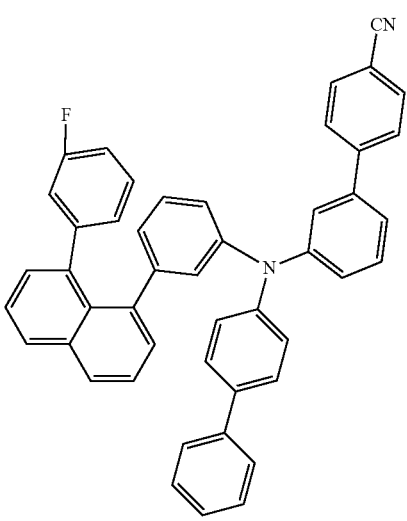
188
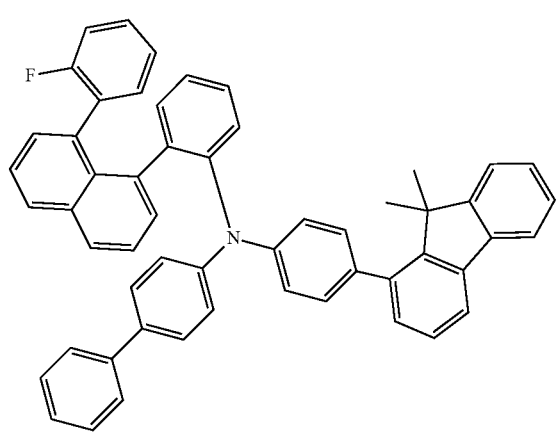
191
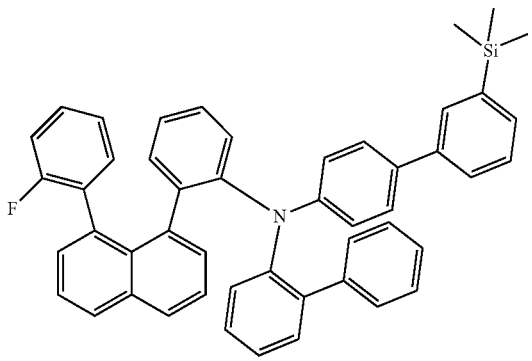

192

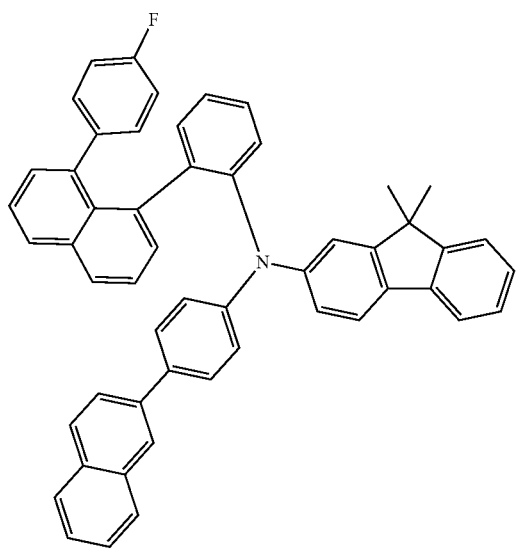

195

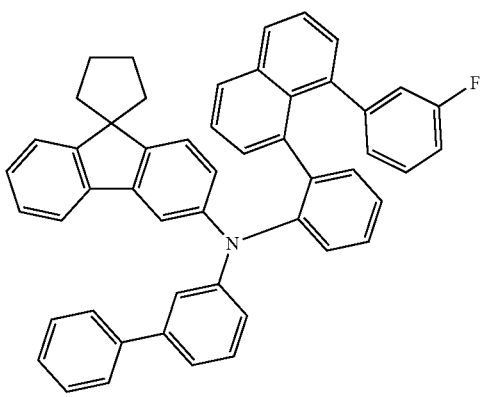

196

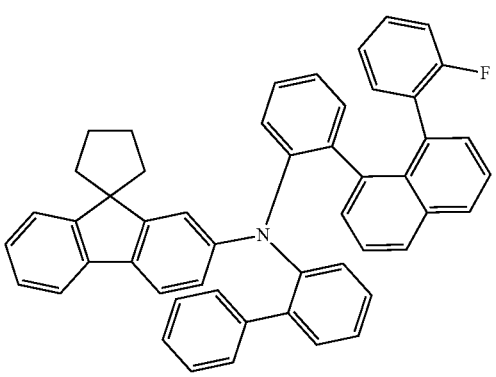

193

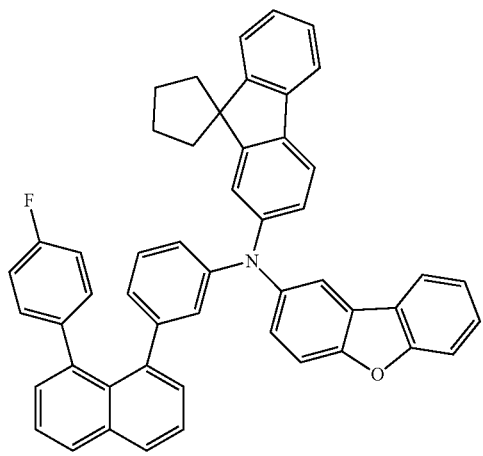

197

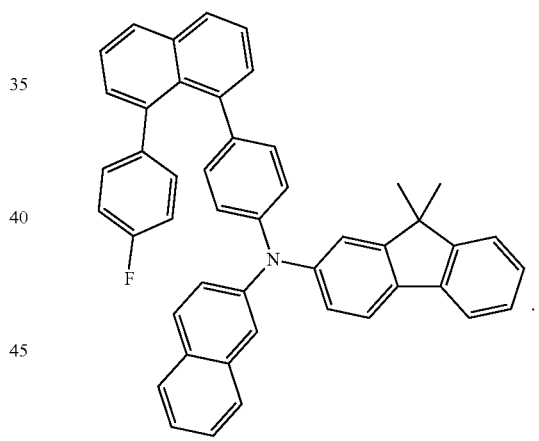

194

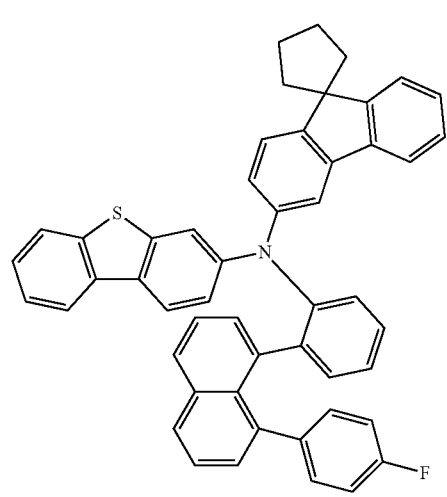

In a second aspect, the present application provides an electronic element, comprising an anode and a cathode which are oppositely disposed, and a functional layer disposed between the anode and the cathode; where the functional layer includes the organic compound of the present application.

Optionally, the electronic element is an organic electroluminescent device or a photoelectric conversion device.

Optionally, the functional layer comprises a hole transporting layer comprising the organic compound of the present application.

Further optionally, the hole transporting layer comprises a first hole transporting layer and a second hole transporting layer, the first hole transporting layer being closer to the anode relative to the second hole transporting layer, wherein the second hole transporting layer comprises the organic compound of the present application.

In one embodiment, the electronic element may be an organic electroluminescent device. As shown in FIG. 1, the organic electroluminescent device may include an anode 100, a first hole transporting layer 321, a second hole transporting layer 322, an organic light-emitting layer 330, an electron transporting layer 340, and a cathode 200 which are sequentially stacked. The first hole transporting layer 321 and the second hole transporting layer 322 constitute a hole transporting layer 320.

Optionally, the anode 100 includes the following anode materials, which are preferably materials having a large work function that facilitate hole injection into the functional layer. Specific examples of the anode materials include metals such as nickel, platinum, vanadium, chromium, copper, zinc, and gold; or their alloy; metal oxides such as zinc oxide, indium oxide, indium tin oxide (ITO) and indium zinc oxide (IZO); combined metals and oxides, such as ZnO: Al or $SnO_2$: Sb; or a conductive polymer such as poly(3-methylthiophene), poly[3,4-(ethylene-1,2-dioxy)thiophene] (PEDT), polypyrrole, and polyaniline, but are not limited to this. A transparent electrode containing indium tin oxide (ITO) as the anode is preferably included.

Optionally, the first hole transporting layer 321 includes one or more hole transport materials, and the hole transport materials may be selected from carbazole polymer, carbazole connected triarylamine compounds or other types of compounds, which are not specially limited in the present application. For example, the first hole transporting layer 321 may consist of a compound NPB and the second hole transporting layer 322 may contain the compound of the present application.

Optionally, the organic light-emitting layer 330 may be composed of a single light-emitting layer material and may also include a host material and a doping material. Optionally, the organic light-emitting layer 330 is composed of the host material and the doping material, holes injected into the organic light-emitting layer 330 and electrons injected into the organic light-emitting layer 330 may be recombined in the organic light-emitting layer 330 to form excitons, the excitons transfer energy to the host material, the host material transfers energy to the doping material, which in turn enables the doping material to emit light.

The host material of the organic light-emitting layer 330 may be a metal chelated compound, a distyryl derivative, an aromatic amine derivative, a dibenzofuran derivative or other types of materials, which is not specially limited in the present application. In one embodiment of the present application, the host material of the organic light-emitting layer 330 is RH-1.

The doping material of the organic light-emitting layer 330 may be a compound with a condensed aryl ring or its derivative, a compound with a heteroaryl ring or its derivative, an aromatic amine derivative or other materials, which is not specially limited in the present application. In one embodiment of the present application, the doping material of the organic light-emitting layer 330 is Ir(piq)$_2$(acac).

The electron transporting layer 340 may be of a single-layer structure or a multi-layer structure and may include one or more electron transport materials, and the electron transport materials may be selected from, but are not limited to, ET-1, TPBi, LiQ, a benzimidazole derivative, an oxadiazole derivative, a quinoxaline derivative or other electron transport materials.

In the present application, the cathode 200 may include a cathode material, which is a material with a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead; or their alloy; or multilayer materials such as LiF/Al, Liq/Al, $LiO_2$/Al, LiF/Ca, LiF/Al, and $BaF_2$/Ca. A metal electrode including magnesium and silver as the cathode is preferably included.

Optionally, as shown in FIG. 1, a hole injection layer 310 may be arranged between the anode 100 and the first hole transporting layer 321 to enhance the ability of injecting holes into the first hole transporting layer 321. The hole injection layer 310 may be made of a benzidine derivative, a starburst arylamine compound, a phthalocyanine derivative or other materials, which is not specially limited in the present application. For example, the hole injection layer 310 may consist of HAT-CN.

Optionally, as shown in FIG. 1, an electron injection layer 350 may be arranged between the cathode 200 and the electron transporting layer 340 to enhance the ability to inject electrons into the electron transporting layer 340. The electron injection layer 350 may include an inorganic material such as an alkali metal sulfide, and an alkali metal halide, or may include a complex of an alkali metal and an organic substance. For example, the electron injection layer 350 may include Yb.

Optionally, the organic electroluminescent device is a red light device.

Figure 3:
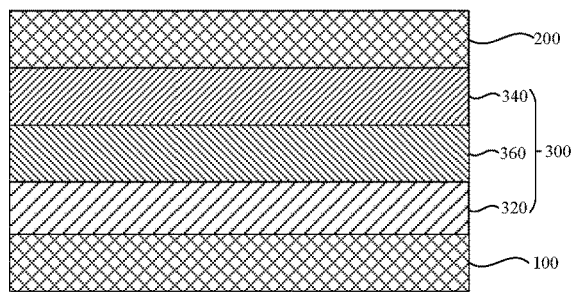
FIG. 3 is a structural schematic diagram of a photoelectric conversion device according to one embodiment of the present application.

According to another embodiment, the electronic element is a photoelectric conversion device. As shown in FIG. 3, the photoelectric conversion device may include an anode 100 and a cathode 200 which are oppositely disposed, and a functional layer 300 disposed between the anode 100 and the cathode 200; where the functional layer 300 includes the organic compound provided by the present application.

According to one specific embodiment, as shown in FIG. 3, a photoelectric conversion device may include an anode 100, a hole transporting layer 320, a photoelectric conversion layer 360, an electron transporting layer 340, and a cathode 200 which are sequentially stacked.

Optionally, the hole transporting layer includes the organic compound of the present application.

Optionally, the photoelectric conversion device may be a solar cell, and in particular may be an organic thin-film solar cell. For example, in one embodiment of the present application, the solar cell includes an anode, a hole transporting layer, a photoelectric conversion layer, an electron transporting layer, and a cathode which are sequentially stacked, where the hole transporting layer includes the organic compound of the present application.

In a third aspect, the present application provides an electronic device, including the electronic element according to the second aspect of the present application.

Figure 2:
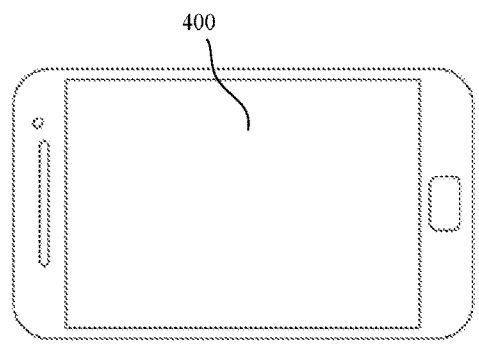
FIG. 2 is a schematic diagram of a first electronic device according to one embodiment of the present application.

According to one embodiment, as shown in FIG. 2, the electronic device is a first electronic device 400, and the first electronic device 400 includes the organic electroluminescent device described above. The first electronic device 400 may be, for example, a display device, a lighting device, an optical communication device or other types of electronic devices, and may include, for example, but is not limited to, a computer screen, a mobile phone screen, a television, an electronic paper, an emergency lighting lamp, an optical module and the like.

Figure 4:
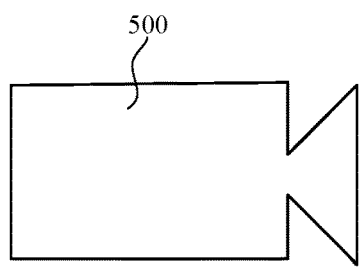
FIG. 4 is a schematic diagram of a second electronic device according to one embodiment of the present application.

According to another embodiment, as shown in FIG. 4, the electronic device is a second electronic device 500, and the second electronic device 500 includes the photoelectric conversion device described above. The second electronic device 500 may be, for example, a solar power plant, a light detector, a fingerprint identification device, a light module, a CCD camera, or other types of electronic devices.

A synthesis method of the organic compound of the present application is specifically described below in conjunction with synthesis examples, but the present application is not limited in any way thus.

Compounds of synthesis methods which are not mentioned in the present application are all commercially available raw material products.

Synthesis Example 1 Synthesis of IM A-1

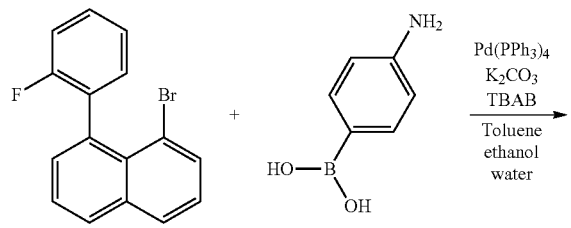

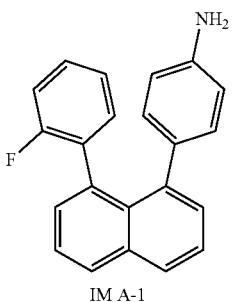

IM A-1

Under nitrogen atmosphere, 1-bromo-8-(2-fluorophenyl) naphthalene (20 g, 66.4 mmol), 4-aminobenzeneboronic acid (10 g, 73.1 mmol), tetrakis(triphenylphosphine)palladium (0.33 g, 0.38 mmol), potassium carbonate (18.4 g, 132.8 mmol), 160 mL of toluene, 80 mL of ethanol and 40 mL of water were added into a 500 mL of three-necked flask, and heated to 70° ° C. to 80° C. and refluxed overnight. After the reaction solution was cooled to room temperature, the reaction solution was washed with water for three times, and finally extracted with a saturated aqueous ammonium chloride solution once, and organic phases were mixed, dried over anhydrous magnesium sulfate, and concentrated by rotary evaporation. The obtained solid material was recrystallized with ethanol to give IM A-1 (13.2 g, yield: 63.5%).

IM A-x listed in Table 1 was synthesized with reference to the method of IM A-1, except that a raw material 1 was used instead of 1-bromo-8-(2-fluorophenyl)naphthalene and a raw material 2 was used instead of 4-aminobenzeneboronic acid, where the main raw materials used, the intermediates synthesized and their yields are as shown in Table 1.

TABLE 1

| Raw material 1 | Raw material 2 | IM A-x | Yield/% |
|---|---|---|---|
| (structure) | (structure) | (structure) | 61.2 |
| (structure) | (structure) | (structure) | 59.1 |
| (structure) | (structure) | (structure) | 61.9 |

TABLE 1-continued

| Raw material 1 | Raw material 2 | IM A-x | Yield/% |
|---|---|---|---|
| 8-bromo-1-(3-fluorophenyl)naphthalene | (3-aminophenyl)boronic acid | 8-(3-aminophenyl)-1-(3-fluorophenyl)naphthalene | 60.8 |
| 8-bromo-1-(3-fluorophenyl)naphthalene | (2-aminophenyl)boronic acid | 8-(2-aminophenyl)-1-(3-fluorophenyl)naphthalene | 59.3 |
| 8-bromo-1-(4-fluorophenyl)naphthalene | (4-aminophenyl)boronic acid | 8-(4-aminophenyl)-1-(4-fluorophenyl)naphthalene | 64.2 |
| 8-bromo-1-(4-fluorophenyl)naphthalene | (3-aminophenyl)boronic acid | 8-(3-aminophenyl)-1-(4-fluorophenyl)naphthalene | 62.5 |
| 8-bromo-1-(4-fluorophenyl)naphthalene | (2-aminophenyl)boronic acid | 8-(2-aminophenyl)-1-(4-fluorophenyl)naphthalene | 59.4 |

Synthesis Example 2 Synthesis of IM B-1

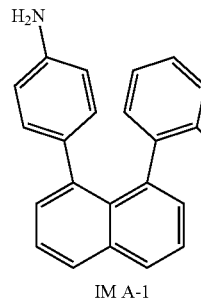

IM A-1

+

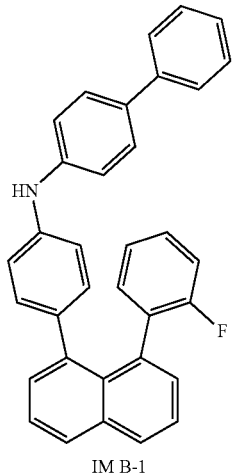

IM B-1

Under a nitrogen atmosphere, IM A-1 (5.5 g, 17.5 mmol), 4-bromobiphenyl (4 g, 17.2 mmol) and 50 mL of toluene were added into a 100 mL of three-necked flask, and heated to 70° C., sodium tert-butoxide (2.5 g, 25.8 mmol), X-Phos (0.16 g, 0.34 mmol) and Pd$_2$(dba)$_3$ (0.16 g, 0.17 mmol) were sequentially added, then heating was performed to 110° C., a reaction was carried out under reflux for 2 h, cooling was performed to room temperature, the reaction solution was washed with water for three times, and dried over anhydrous magnesium sulfate, after standing for 30 min, suction filtration was performed, concentration was performed under reduced pressure, and the concentrated material was allowed to pass through a chromatographic column for column chromatography to give IM B-1 (6.3 g, yield: 78.2%).

IM B-x listed in Table 2 was synthesized with reference to the method of IM B-1, except that IM A-x was used instead of IM A-1 and a raw material 3 was used instead of 4-bromobiphenyl, where the main raw materials used, the intermediates synthesized and their yields are as shown in Table 2.

TABLE 2

| IM A-x | Raw material 3 | IM B-x | Yield/% |
|---|---|---|---|
| 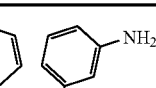<br>IM A-2 | 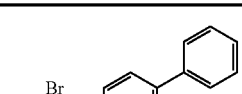 | 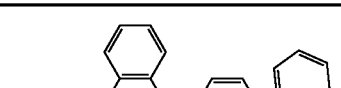<br>IM B-2 | 73.7 |
| <br>IM A-2 |  | <br>IM B-3 | 76.5 |

TABLE 2-continued
| IM A-x | Raw material 3 | IM B-x | Yield/% |
|---|---|---|---|
|  IM A-2 | 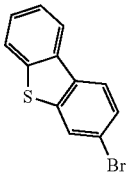 | 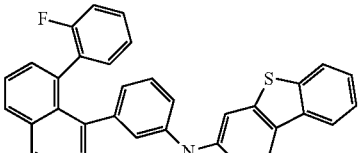 IM B-4 | 75.9 |
| 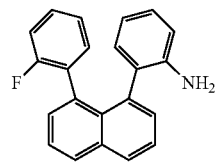 [SMILES: Nc1ccccc1-c1cccc2cccc(-c3ccccc3F)c12] IM A-3 | 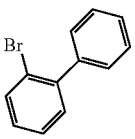 [SMILES: Brc1ccccc1-c1ccccc1] | 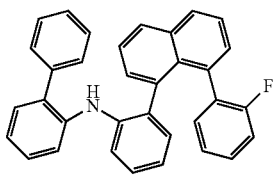 [SMILES: Fc1ccccc1-c1cccc2cccc(-c3ccccc3Nc3ccccc3-c3ccccc3)c12] IM B-5 | 72.6 |
| 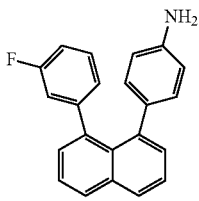 [SMILES: Nc1ccc(-c2cccc3cccc(-c4cccc(F)c4)c23)cc1] IM A-4 | 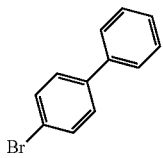 [SMILES: Brc1ccc(-c2ccccc2)cc1] | 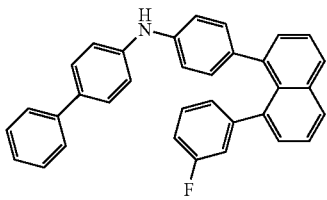 [SMILES: Fc1cccc(-c2cccc3cccc(-c4ccc(Nc5ccc(-c6ccccc6)cc5)cc4)c23)c1] IM B-6 | 76.4 |
| 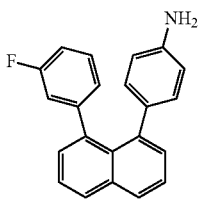 [SMILES: Nc1ccc(-c2cccc3cccc(-c4cccc(F)c4)c23)cc1] IM A-4 | 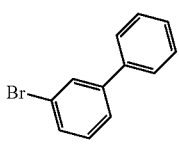 [SMILES: Brc1cccc(-c2ccccc2)c1] | 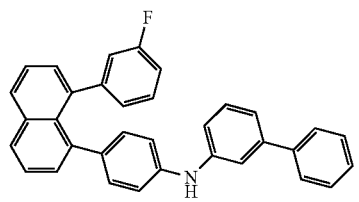 [SMILES: Fc1cccc(-c2cccc3cccc(-c4ccc(Nc5cccc(-c6ccccc6)c5)cc4)c23)c1] IM B-7 | 73.5 |
| 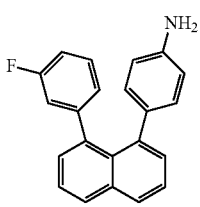 [SMILES: Nc1ccc(-c2cccc3cccc(-c4cccc(F)c4)c23)cc1] IM A-4 | 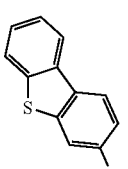 | 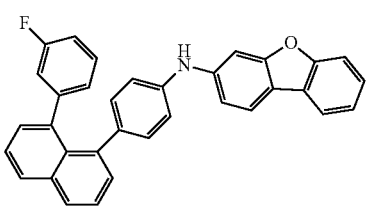 [SMILES: Fc1cccc(-c2cccc3cccc(-c4ccc(Nc5ccc6c(c5)oc5ccccc56)cc4)c23)c1] IM B-8 | 74.2 |
| 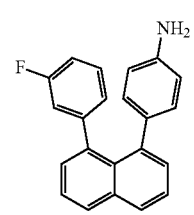 [SMILES: Nc1ccc(-c2cccc3cccc(-c4cccc(F)c4)c23)cc1] IM A-4 | 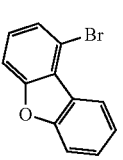 [SMILES: Brc1cccc2oc3ccccc3c12] | 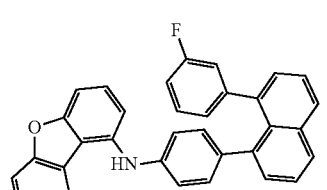 IM B-9 | 71.3 |

TABLE 2-continued
| IM A-x | Raw material 3 | IM B-x | Yield/% |
|---|---|---|---|
| 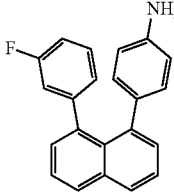<br>IM A-4 | 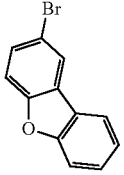 [SMILES: Brc1ccc2oc3ccccc3c2c1] | 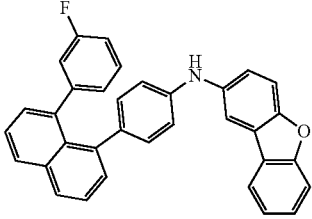 [SMILES: Fc1cccc(-c2cccc3cccc(-c4ccc(Nc5ccc6oc7ccccc7c6c5)cc4)c23)c1]<br>IM B-10 | 72.9 |
| 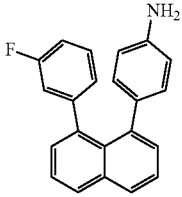 [SMILES: Nc1ccc(-c2cccc3cccc(-c4cccc(F)c4)c23)cc1]<br>IM A-4 | 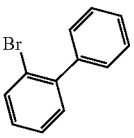 [SMILES: Brc1ccccc1-c1ccccc1] | 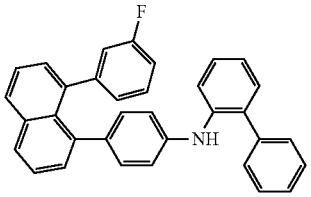 [SMILES: Fc1cccc(-c2cccc3cccc(-c4ccc(Nc5ccccc5-c5ccccc5)cc4)c23)c1]<br>IM B-11 | 73.7 |
| 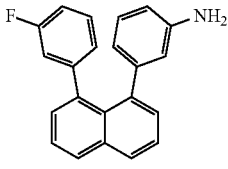 [SMILES: Nc1cccc(-c2cccc3cccc(-c4cccc(F)c4)c23)c1]<br>IM A-5 | 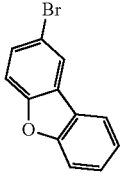 | 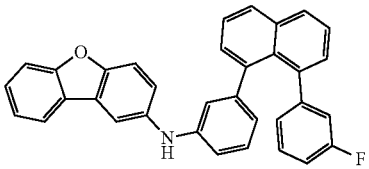 [SMILES: Fc1cccc(-c2cccc3cccc(-c4cccc(Nc5ccc6oc7ccccc7c6c5)c4)c23)c1]<br>IM B-12 | 71.3 |
| 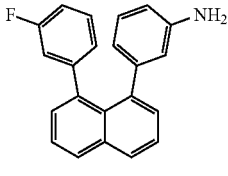 [SMILES: Nc1cccc(-c2cccc3cccc(-c4cccc(F)c4)c23)c1]<br>IM A-5 | 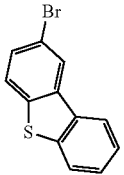 [SMILES: Brc1ccc2sc3ccccc3c2c1] | 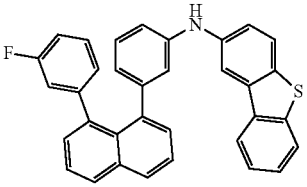 [SMILES: Fc1cccc(-c2cccc3cccc(-c4cccc(Nc5ccc6sc7ccccc7c6c5)c4)c23)c1]<br>IM B-13 | 70.4 |
| 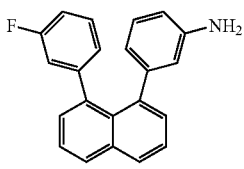 [SMILES: Nc1cccc(-c2cccc3cccc(-c4cccc(F)c4)c23)c1]<br>IM A-5 | 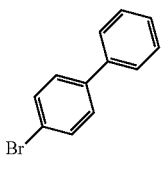 [SMILES: Brc1ccc(-c2ccccc2)cc1] | 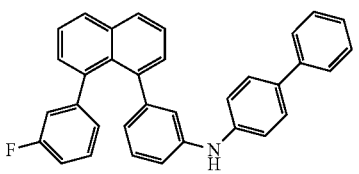 [SMILES: Fc1cccc(-c2cccc3cccc(-c4cccc(Nc5ccc(-c6ccccc6)cc5)c4)c23)c1]<br>IM B-14 | 75.6 |
| 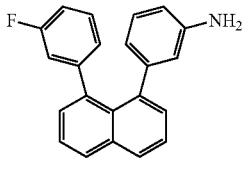 [SMILES: Nc1cccc(-c2cccc3cccc(-c4cccc(F)c4)c23)c1]<br>IM A-5 | 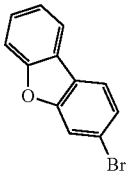 [SMILES: Brc1ccc2c(c1)oc1ccccc12] | 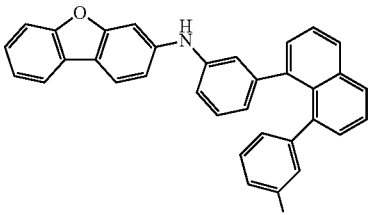<br>IM B-15 | 73.1 |

TABLE 2-continued

| IM A-x | Raw material 3 | IM B-x | Yield/% |
|---|---|---|---|
| IM A-5 | (dibenzothiophene-Br) | IM B-16 | 75.3 |
| IM A-6 | (9,9-dimethylfluorene-Br) | IM B-17 | 72.5 |
| IM A-6 | (4-bromobiphenyl) | IM B-18 | 77.8 |
| IM A-7 | (4-bromobiphenyl) | IM B-19 | 76.9 |
| IM A-7 | (9,9-dimethylfluorene-Br) | IM B-20 | 75.7 |
| IM A-7 | (2-bromobiphenyl) | IM B-21 | 71.2 |

TABLE 2-continued
| IM A-x | Raw material 3 | IM B-x | Yield/% |
|---|---|---|---|
| 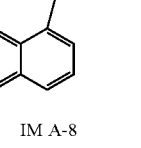<br>IM A-8 | 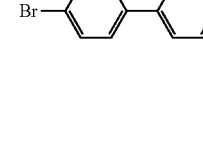 | 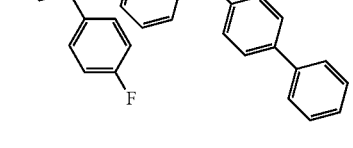<br>IM B-22 | 73.4 |
| 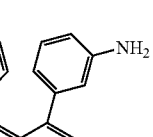<br>IM A-8 | 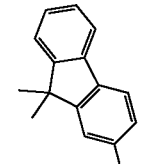 | 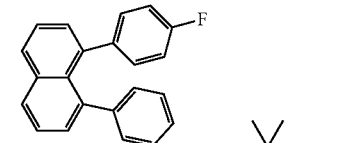<br>IM B-23 | 73.8 |
| <br>IM A-8 | 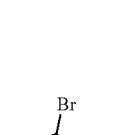 | <br>IM B-24 | 68.3 |
| <br>IM A-9 |  | <br>IM B-25 | 72.1 |

Synthesis Example 3 Synthesis of a Compound 13

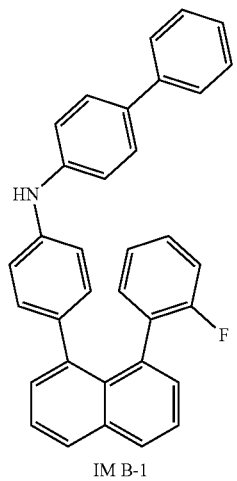

IM B-1

+

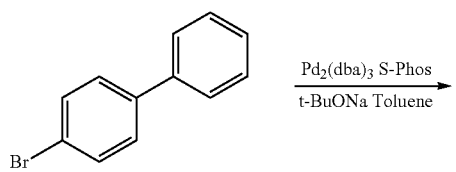

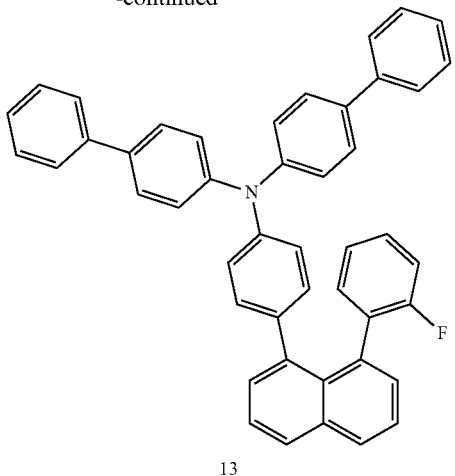

13

Under a nitrogen atmosphere, IM B-1 (5 g, 10.7 mmol), 4-bromobiphenyl (2.5 g, 10.7 mmol) and 50 mL of toluene were added into a 100 mL of three-necked flask, heated to 70° C., sodium tert-butoxide (1.5 g, 16.1 mmol), 2-dicyclohexylphosphine-2',6'-dimethoxy-1,1'-biphenyl (S-Phos) (0.09 g, 0.21 mmol) and $Pd_2(dba)_3$ (0.10 g, 0.11 mmol) were sequentially added, then heating was performed to 110° C., a reaction was carried out under reflux for 2 h, cooling was performed to room temperature, the reaction solution was washed with water for three times, and dried over anhydrous magnesium sulfate, after standing for 30 min, suction filtration was performed, concentration was performed under reduced pressure, the concentrated material was allowed to pass through a chromatographic column for column chromatography, and finally recrystallization was performed by using n-heptane to give Compound 13 (3.7 g, yield: 55.8%); mass spectrum (m/z)=618.25 [M+H]$^+$.

Compounds listed in Table 3 were synthesized with reference to the method of Compound 13, except that IM B-x was used instead of IM B-1 and a raw material 4 was used instead of 4-bromobiphenyl, where the main raw materials used, the compounds synthesized and their yields and mass spectra are shown in Table 3.

TABLE 3

| IM B-x | Raw material 4 | Compound | Yield/% | Mass spectrum (m/z)/[M + H]+ |
|---|---|---|---|---|
| IM B-1 | | 18 | 58.3 | 694.28 |
| IM B-2 | | 28 | 50.4 | 734.31 |

TABLE 3-continued

| IM B-x | Raw material 4 | Compound | Yield/% | Mass spectrum (m/z)/[M + H]+ |
|---|---|---|---|---|
| IM B-3 | | 34 | 51.6 | 632.23 |
| IM B-4 | | 53 | 51.3 | 662.19 |

TABLE 3-continued

| IM B-x | Raw material 4 | Compound | Yield/% | Mass spectrum (m/z)/[M + H]+ |
|---|---|---|---|---|
| IM B-5 | | 48 | 47.6 | 694.28 |
| IM B-5 | | 191 | 45.8 | 690.29 |
| IM B-6 | | 93 | 46.4 | 658.29 |

TABLE 3-continued

| IM B-x | Raw material 4 | Compound | Yield/% | Mass spectrum (m/z) [M + H]+ |
|---|---|---|---|---|
| IM B-6 | | 94 | 51.6 | 707.28 |
| IM B-6 | | 101 | 48.3 | 780.30 |

TABLE 3-continued

| IM B-x | Raw material 4 | Compound | Yield/% | Mass spectrum (m/z)/[M + H]⁺ |
|---|---|---|---|---|
| IM B-6 | | 103 | 52.4 | 892.43 |
| IM B-6 | | 105 | 52.8 | 658.29 |

TABLE 3-continued

| IM B-x | Raw material 4 | Compound | | Yield/% | Mass spectrum (m/z)/[M + H]+ |
|---|---|---|---|---|---|
| IM B-6 | (9,9'-spirobifluorene-Br) | 106 | | 53.4 | 780.30 |
| IM B-6 | (dibenzofuran-Br) | 107 | | 47.8 | 632.23 |

TABLE 3-continued

| IM B-x | Raw material 4 | Compound | Yield/% | Mass spectrum (m/z)/[M + H]+ |
|---|---|---|---|---|
| IM B-6 | | 109 | 45.3 | 707.28 |
| IM B-7 | | 95 | 46.1 | 659.29 |

TABLE 3-continued

| IM B-x | Raw material 4 | Compound | Yield/% | Mass spectrum (m/z)/[M + H]⁺ |
|---|---|---|---|---|
| IM B-8 | | 96 | 52.9 | 708.27 |
| IM B-8 | | 98 | 49.2 | 796.30 |

TABLE 3-continued

| IM B-x | Raw material 4 | Compound | Yield/% | Mass spectrum (m/z) [M + H]⁺ |
|---|---|---|---|---|
| IM B-8 | | 100 | 47.8 | 672.27 |
| IM B-8 | | 108 | 53.7 | 672.27 |
| IM B-9 | | 97 | 46.9 | 672.27 |

TABLE 3-continued

| IM B-x | Raw material 4 | Compound | Yield/% | Mass spectrum (m/z)/[M + H]+ |
|---|---|---|---|---|
| IM B-10 | | 99 | 53.7 | 672.27 |
| IM B-11 | | 102 | 46.2 | 780.30 |
| IM B-11 | | 104 | 44.8 | 892.43 |

TABLE 3-continued

| IM B-x | Raw material 4 | Compound | Yield/% | Mass spectrum (m/z)/[M + H]+ |
|---|---|---|---|---|
| IM B-12 | | 61 | 45.8 | 712.30 |
| IM B-13 | | 62 | 42.9 | 728.27 |

TABLE 3-continued

| IM B-x | Raw material 4 | Compound | Yield/% | Mass spectrum (m/z)/[M + H]+ |
|---|---|---|---|---|
| IM B-14 | | 63 | 45.5 | 782.32 |
| IM B-14 | | 67 | 44.8 | 780.30 |

TABLE 3-continued

| IM B-x | Raw material 4 | Compound | Yield/% | Mass spectrum (m/z)/[M + H]+ |
|---|---|---|---|---|
| IM B-14 | | 73 | 46.9 | 783.31 |
| IM B-14 | | 190 | 50.2 | 643.25 |

TABLE 3-continued

| IM B-x | Raw material 4 | Compound | Yield/% | Mass spectrum (m/z)/[M + H]+ |
|---|---|---|---|---|
| IM B-15 | | 65 | 48.5 | 796.30 |
| IM B-16 | | 66 | 47.7 | 812.27 |

TABLE 3-continued

| IM B-x | Raw material 4 | Compound | Yield/% | Mass spectrum (m/z)/[M + H]+ |
|---|---|---|---|---|
| IM B-17 | | 81 | 49.4 | 820.33 |
| IM B-18 | | 82 | 50.1 | 780.30 |
| IM B-18 | | 185 | 48.9 | 208.26 |

TABLE 3-continued

| IM B-x | Raw material 4 | Compound | Yield/% | Mass spectrum (m/z)/[M + H]⁺ |
|---|---|---|---|---|
| IM B-18 | | 186 | 46.5 | 724.24 |
| IM B-19 | | 129 | 50.6 | 780.30 |

TABLE 3-continued

| IM B-x | Raw material 4 | Compound | Yield/% | Mass spectrum (m/z)/[M + H]⁺ |
|---|---|---|---|---|
| IM B-19 | | 130 | 53.4 | 632.23 |
| IM B-19 | | 131 | 54.8 | 648.21 |
| IM B-19 | | 132 | 53.9 | 780.30 |

TABLE 3-continued

| IM B-x | Raw material 4 | Compound | Yield/% | Mass spectrum (m/z) [M + H]+ |
|---|---|---|---|---|
| IM B-19 | | 133 | 50.7 | 892.43 |
| IM B-19 | | 141 | 56.6 | 658.29 |

TABLE 3-continued

| IM B-x | Raw material 4 | Compound | Yield/% | Mass spectrum (m/z)/[M + H]⁺ |
|---|---|---|---|---|
| IM B-19 | | 189 | 53.5 | 636.35 |
| IM B-20 | | 142 | 52.1 | 658.29 |
| IM B-20 | | 134 | 45.8 | 770.41 |

TABLE 3-continued

| IM B-x | Raw material 4 | Compound | Yield/% | Mass spectrum (m/z)/[M + H]+ |
|---|---|---|---|---|
| IM B-20 | | 143 | 53.5 | 688.24 |
| IM B-20 | | 144 | 50.9 | 672.27 |

TABLE 3-continued
| IM B-x | Raw material 4 | Compound | Yield/% | Mass spectrum (m/z)/[M + H]+ |
|---|---|---|---|---|
| 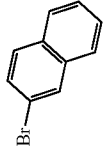 IM B-20 | 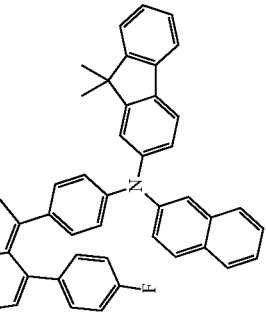 | 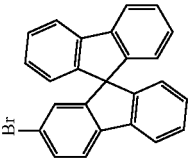 197 | 49.9 | 632.27 |
|  IM B-21 | 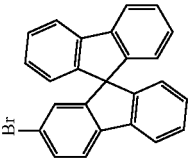 |  135 | 45.7 | 780.30 |
| IM B-21 |  | 136 | 44.9 | 892.43 |

TABLE 3-continued

| IM B-x | Raw material 4 | Compound | Yield/% | Mass spectrum (m/z)/[M + H]+ |
|---|---|---|---|---|
| IM B-22 | | 159 | 46.2 | 784.30 |
| IM B-23 | | 162 | 50.1 | 748.30 |

TABLE 3-continued

| IM B-x | Raw material 4 | Compound | Yield/% | Mass spectrum (m/z)/[M + H]+ |
|---|---|---|---|---|
| IM B-24 | | 193 | 50.1 | 698.28 |
| IM B-25 | | 177 | 49.3 | 618.26 |

TABLE 3-continued

| IM B-x | Raw material 4 | Compound | Yield/% | Mass spectrum (m/z)/[M + H]+ |
|---|---|---|---|---|
| IM B-25 | | 180 | 48.4 | 658.29 |

NMR data for the compound 13:

$^1$H-NMR (CDCl$_3$, 400 MHz): 7.82-7.80 (d, 2H), 7.59-7.50 (m, 10H), 7.42-7.12 (m, 14H), 6.77-6.75 (d, 2H), 6.51-6.48 (d, 4H).

NMR data for a compound 131:

$^1$H-NMR (CDCl$_3$, 400 MHZ): 8.21-8.19 (d, 1H), 8.06-8.04 (d, 1H), 7.96-7.94 (d, 1H), 7.78-7.75 (d, 2H), 7.64-7.63 (d, 1H), 7.57-7.48 (m, 7H), 7.44-7.25 (m, 12H), 6.95-6.93 (m, 1H), 6.84-6.82 (d, 2H), 6.68-6.66 (d, 2H).

DEVICE EXAMPLES

Example 1: Red Organic Electroluminescent Device

An ITO/Ag/ITO substrate (manufactured by Corning) having a thickness of 1200 Å was cut into a size of 40 mm (length)×40 mm (width)×0.7 mm (height) to be prepared into an experimental substrate having an anode and an insulating layer pattern by using a photoetching process, and surface treatment was performed by utilizing ultraviolet ozone and O$_2$: N$_2$ plasma to increase the work function of the anode (the experimental substrate) and remove scum.

First, HAT-CN was vacuum evaporated on the experimental substrate (the anode) to form a hole injection layer (HIL) having a thickness of 100 Å, and NPB was evaporated on the hole injection layer to form a first hole transporting layer (HTL) having a thickness of 1115 Å.

A compound 13 was vacuum evaporated on the first hole transporting layer to form a second hole transporting layer having a thickness of 840 Å.

RH-1 and Ir(piq)$_2$(acac) were co-evaporated on the second hole transporting layer at an evaporation ratio of 95%:5% to form an organic light-emitting layer (R-EML) having a thickness of 380 Å.

ET-1 and LiQ were co-evaporated on the organic light-emitting layer at an evaporation ratio of 1:1 to form an electron transporting layer (ETL) having a thickness of 350 Å, Yb was evaporated on the electron transporting layer to form an electron injection layer (EIL) having a thickness of 10 Å, and then magnesium (Mg) and silver (Ag) were vacuum evaporated on the electron injection layer at an evaporation rate of 1:9 to form a cathode having a thickness of 125 Å.

Finally, CP-1 was evaporated on the cathode to form an organic capping layer (CPL) having a thickness of 630 Å, thus completing the manufacture of the organic light-emitting device.

Examples 2-55

An organic electroluminescent device was manufactured by the same method as that in Example 1 except that Compounds shown in Table 5 below were used instead of Compound 13 when the second hole transporting layer was formed.

Comparative Examples 1-5

An organic electroluminescent device was manufactured by the same method as that in Example 1 except that Compound A, Compound B, Compound C, Compound D and Compound E were used instead of Compound 13 when the second hole transporting layer was formed.

The structures of main materials used in Examples and Comparative examples are shown in Table 4 below:

TABLE 4

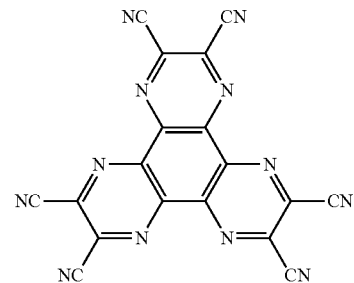 [SMILES: N#Cc1nc2c3nc(C#N)c(C#N)nc3c3nc(C#N)c(C#N)nc3c2nc1C#N]

HAT-CN

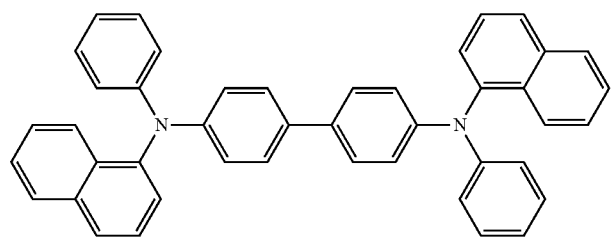 [SMILES: c1ccc(N(c2ccc(-c3ccc(N(c4ccccc4)c4cccc5ccccc45)cc3)cc2)c2cccc3ccccc23)cc1]

NPB

TABLE 4-continued
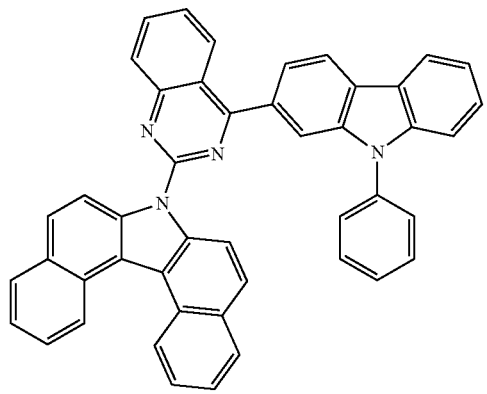 [SMILES: c1ccc(-n2c3ccccc3c3ccc(-c4nc(-n5c6ccc7ccccc7c6c6c7ccccc7ccc65)nc5ccccc45)cc32)cc1]
RH-1
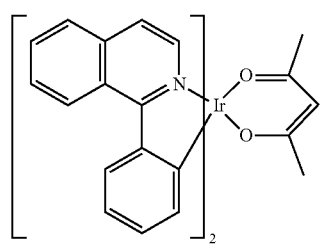
Ir(piq)₂(acac)
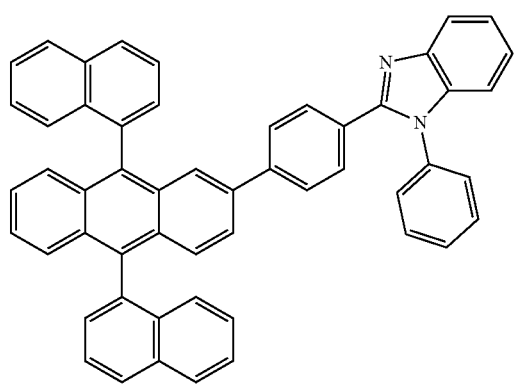 [SMILES: c1ccc(-n2c(-c3ccc(-c4ccc5c(-c6cccc7ccccc67)c6ccccc6c(-c6cccc7ccccc67)c5c4)cc3)nc3ccccc32)cc1]
ET-1
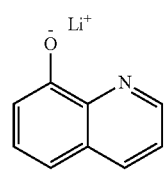
LiQ TABLE 4-continued
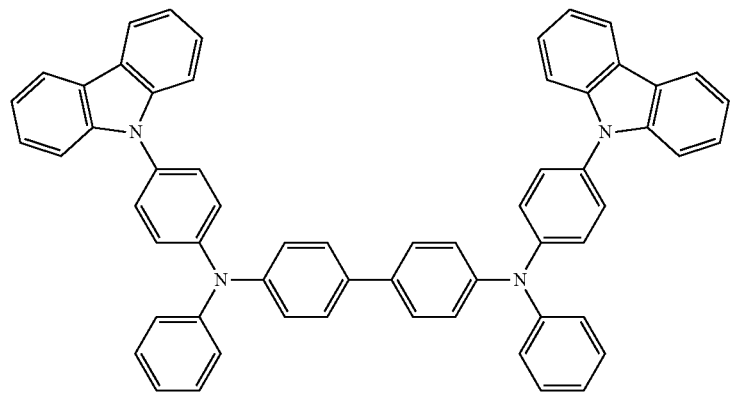 [SMILES: c1ccc(N(c2ccc(-c3ccc(N(c4ccccc4)c4ccc(-n5c6ccccc6c6ccccc65)cc4)cc3)cc2)c2ccc(-n3c4ccccc4c4ccccc43)cc2)cc1]
CP-1
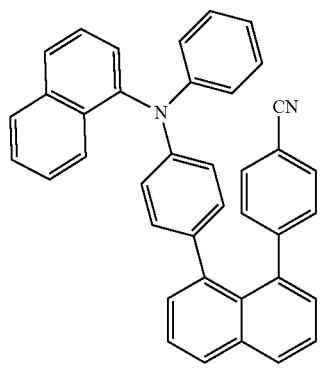 [SMILES: N#Cc1ccc(-c2cccc3cccc(-c4ccc(N(c5ccccc5)c5cccc6ccccc56)cc4)c23)cc1]
Compound A
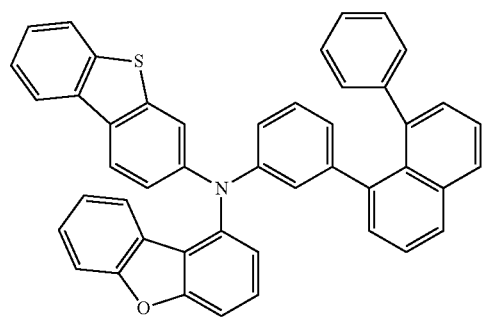 [SMILES: c1ccc(-c2cccc3cccc(-c4cccc(N(c5ccc6c(c5)sc5ccccc56)c5cccc6oc7ccccc7c56)c4)c23)cc1]
Compound B TABLE 4-continued
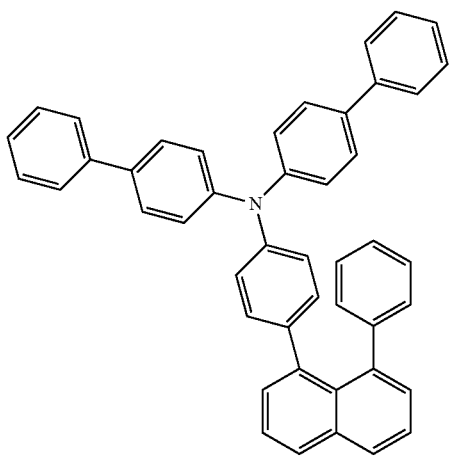 [SMILES: c1ccc(-c2ccc(N(c3ccc(-c4ccccc4)cc3)c3ccc(-c4cccc5cccc(-c6ccccc6)c45)cc3)cc2)cc1]
Compound C
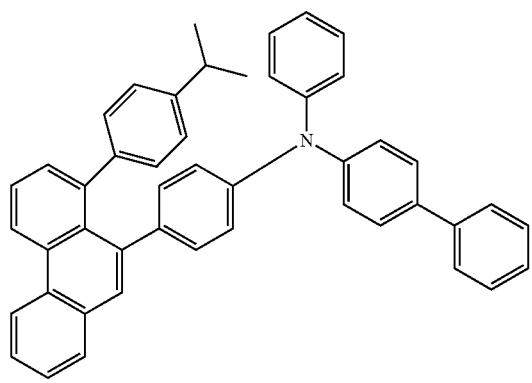 [SMILES: CC(C)c1ccc(-c2cccc3c2c(-c2ccc(N(c4ccccc4)c4ccc(-c5ccccc5)cc4)cc2)cc2ccccc23)cc1]
Compound D
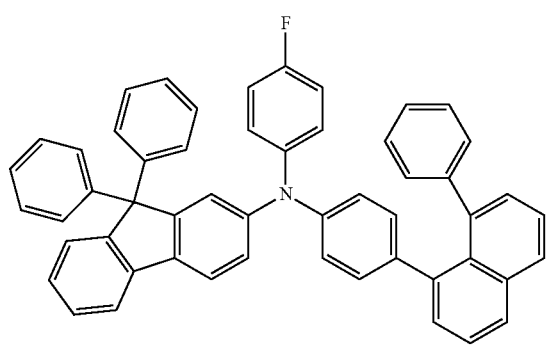 [SMILES: Fc1ccc(N(c2ccc(-c3cccc4cccc(-c5ccccc5)c34)cc2)c2ccc3c(c2)C(c2ccccc2)(c2ccccc2)c2ccccc2-3)cc1]
Compound E The devices manufactured in Examples and Comparative examples were subjected to performance tests, where IVL (Operating voltage, Current efficiency, and Chromaticity coordinate) data was tested at a current density of 10 mA/cm$^2$ and T95 service life was tested at a current density of 20 mA/cm$^2$, and the results are shown in Table 5.

TABLE 5

| Example No. | Second hole transporting layer | Operating voltage (V) | Current efficiency (Cd/A) | Chromaticity coordinate CIEx, CIEy | T95 service life (h) |
|---|---|---|---|---|---|
| Example 1 | Compound 13 | 3.77 | 36.49 | 0.678, 0.318 | 367 |
| Example 2 | Compound 18 | 3.75 | 37.21 | 0.677, 0.318 | 357 |
| Example 3 | Compound 28 | 3.74 | 35.83 | 0.676, 0.317 | 387 |
| Example 4 | Compound 34 | 3.81 | 35.91 | 0.677, 0.318 | 376 |
| Example 5 | Compound 35 | 3.82 | 35.57 | 0.679, 0.318 | 401 |
| Example 6 | Compound 48 | 3.73 | 35.72 | 0.679, 0.318 | 356 |
| Example 7 | Compound 191 | 3.65 | 34.83 | 0.676, 0.317 | 360 |
| Example 8 | Compound 93 | 3.78 | 35.27 | 0.679, 0.318 | 385 |
| Example 9 | Compound 94 | 3.77 | 37.72 | 0.679, 0.319 | 343 |
| Example 10 | Compound 101 | 3.74 | 37.45 | 0.677, 0.317 | 355 |
| Example 11 | Compound 103 | 3.80 | 36.63 | 0.677, 0.319 | 346 |
| Example 12 | Compound 105 | 3.66 | 36.29 | 0.678, 0.318 | 394 |
| Example 13 | Compound 106 | 3.77 | 36.15 | 0.677, 0.317 | 354 |
| Example 14 | Compound 107 | 3.71 | 37.47 | 0.678, 0.317 | 380 |
| Example 15 | Compound 109 | 3.71 | 37.42 | 0.676, 0.317 | 342 |
| Example 16 | Compound 95 | 3.79 | 36.98 | 0.677, 0.318 | 388 |
| Example 17 | Compound 96 | 3.81 | 36.44 | 0.676, 0.318 | 376 |
| Example 18 | Compound 98 | 3.78 | 36.28 | 0.676, 0.317 | 407 |
| Example 19 | Compound 100 | 3.74 | 37.11 | 0.678, 0.317 | 408 |
| Example 20 | Compound 108 | 3.75 | 36.52 | 0.679, 0.318 | 415 |
| Example 21 | Compound 97 | 3.75 | 36.18 | 0.676, 0.318 | 411 |
| Example 22 | Compound 99 | 3.69 | 37.32 | 0.676, 0.317 | 410 |
| Example 23 | Compound 102 | 3.73 | 35.68 | 0.679, 0.318 | 353 |
| Example 24 | Compound 104 | 3.74 | 36.62 | 0.678, 0.317 | 347 |
| Example 25 | Compound 61 | 3.70 | 35.43 | 0.676, 0.318 | 371 |
| Example 26 | Compound 62 | 3.82 | 34.71 | 0.676, 0.317 | 368 |
| Example 27 | Compound 63 | 3.76 | 35.75 | 0.676, 0.317 | 384 |
| Example 28 | Compound 67 | 3.74 | 35.92 | 0.676, 0.317 | 349 |
| Example 29 | Compound 73 | 3.77 | 35.34 | 0.677, 0.318 | 341 |
| Example 30 | Compound 190 | 3.67 | 35.09 | 0.677, 0.317 | 362 |
| Example 31 | Compound 65 | 3.73 | 34.92 | 0.677, 0.317 | 404 |
| Example 32 | Compound 66 | 3.81 | 36.19 | 0.676, 0.318 | 401 |
| Example 33 | Compound 81 | 3.79 | 35.23 | 0.678, 0.317 | 382 |
| Example 34 | Compound 82 | 3.74 | 35.96 | 0.676, 0.318 | 348 |
| Example 35 | Compound 185 | 3.69 | 36.66 | 0.676, 0.317 | 374 |
| Example 36 | Compound 186 | 3.72 | 36.37 | 0.676, 0.317 | 369 |
| Example 37 | Compound 129 | 3.68 | 36.54 | 0.676, 0.318 | 352 |
| Example 38 | Compound 130 | 3.71 | 34.97 | 0.676, 0.319 | 379 |
| Example 39 | Compound 131 | 3.72 | 36.38 | 0.677, 0.319 | 370 |
| Example 40 | Compound 132 | 3.70 | 37.63 | 0.676, 0.318 | 351 |
| Example 41 | Compound 133 | 3.81 | 37.81 | 0.676, 0.317 | 345 |
| Example 42 | Compound 141 | 3.76 | 35.82 | 0.676, 0.317 | 398 |
| Example 43 | Compound 189 | 3.74 | 35.81 | 0.677, 0.317 | 363 |
| Example 44 | Compound 142 | 3.81 | 36.61 | 0.677, 0.317 | 393 |
| Example 45 | Compound 134 | 3.75 | 36.75 | 0.677, 0.317 | 390 |
| Example 46 | Compound 143 | 3.68 | 36.26 | 0.676, 0.317 | 405 |
| Example 47 | Compound 144 | 3.80 | 37.82 | 0.678, 0.317 | 413 |
| Example 48 | Compound 135 | 3.76 | 37.43 | 0.676, 0.319 | 350 |
| Example 49 | Compound 136 | 3.82 | 36.81 | 0.676, 0.318 | 344 |
| Example 50 | Compound 159 | 3.81 | 35.14 | 0.677, 0.319 | 373 |
| Example 51 | Compound 162 | 3.75 | 35.66 | 0.678, 0.318 | 400 |
| Example 52 | Compound 193 | 3.73 | 36.12 | 0.676, 0.318 | 340 |
| Example 53 | Compound 177 | 3.73 | 35.95 | 0.676, 0.318 | 364 |
| Example 54 | Compound 180 | 3.77 | 35.84 | 0.678, 0.317 | 395 |
| Example 55 | Compound 197 | 3.76 | 36.48 | 0.678, 0.318 | 392 |
| Comparative example 1 | Compound A | 4.01 | 29.22 | 0.678, 0.318 | 295 |
| Comparative example 2 | Compound B | 3.95 | 29.94 | 0.676, 0.317 | 291 |
| Comparative example 3 | Compound C | 3.98 | 28.71 | 0.676, 0.318 | 303 |
| Comparative example 4 | Compound D | 4.05 | 29.31 | 0.676, 0.319 | 301 |
| Comparative example 5 | Compound E | 3.94 | 28.83 | 0.676, 0.318 | 298 |

From the results of the above Table 5, it can be seen that the performance of the organic electroluminescent devices in Examples 1-55 is improved compared with the organic electroluminescent devices in Comparative examples 1-5; specifically, the organic electroluminescent devices in Examples 1-55 have the advantages that the current efficiency is improved by at least 15.9%, and the service life is improved by at least 12.2% compared with Comparative examples. Thus, when the organic compound of the present application is used in a second hole transporting layer of an organic electroluminescent device, the current efficiency and service life can be simultaneously improved while maintaining a low operating voltage.

It will be understood by those of ordinary skill in the art that the above embodiments are specific examples for implementing the present application, and that various changes may be made in form and detail in actual application without departing from the spirit and scope of the present application.

What is claimed is:

1. An organic compound having a structure represented by Formula I:

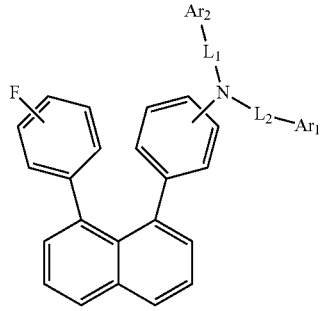

Formula I wherein Ar$_1$ and Ar$_2$ are each independently selected from a substituted or unsubstituted aryl with 6 to 33 carbon atoms, or a substituted or unsubstituted heteroaryl with 12 to 18 carbon atoms;

substituents of Ar$_1$ and Ar$_2$ are each independently selected from deuterium, a fluorine, a cyano, a trialkylsilyl with 3 to 6 carbon atoms, a haloalkyl with 1 to 5 carbon atoms, an alkyl with 1 to 5 carbon atoms, an aryl with 6 to 12 carbon atoms or a heteroaryl with 5 to 12 carbon atoms; optionally, in Ar$_1$ and Ar$_2$, any two adjacent substituents form a substituted or unsubstituted 5-membered to 13-membered ring; and substituents of the 5-membered to 13-membered ring are independently selected from deuterium, a fluorine, a cyano, a trimethylsilyl, a trifluoromethyl, a methyl, an ethyl, an isopropyl or a tert-butyl;

L$_1$ and L$_2$ are selected from a single bond, or a substituted or unsubstituted group V, wherein the unsubstituted group V is selected from the following groups:

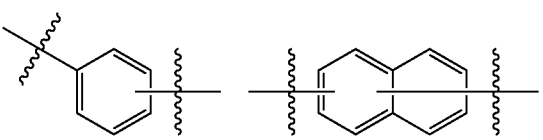

-continued

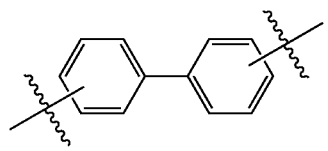

where the substituted group V has one or two or more substituents, the substituents are independently selected from a methyl, an ethyl, an isopropyl, a tert-butyl or a phenyl, and when the number of the substituents is greater than 1, the substituents are the same or different.

2. The organic compound of claim 1, wherein $Ar_1$ and $Ar_2$ are each independently selected from a substituted or unsubstituted phenyl, a substituted or unsubstituted naphthyl, a substituted or unsubstituted biphenyl, a substituted or unsubstituted fluorenyl, a substituted or unsubstituted dibenzofuranyl, a substituted or unsubstituted pyridyl, a substituted or unsubstituted dibenzothienyl, a substituted or unsubstituted carbazolyl, a substituted or unsubstituted phenanthryl, or a substituted or unsubstituted triphenylene.

3. The organic compound of claim 1, wherein $Ar_1$ and $Ar_2$ are each independently selected from a substituted or unsubstituted group W, wherein the unsubstituted group W is selected from the following groups:

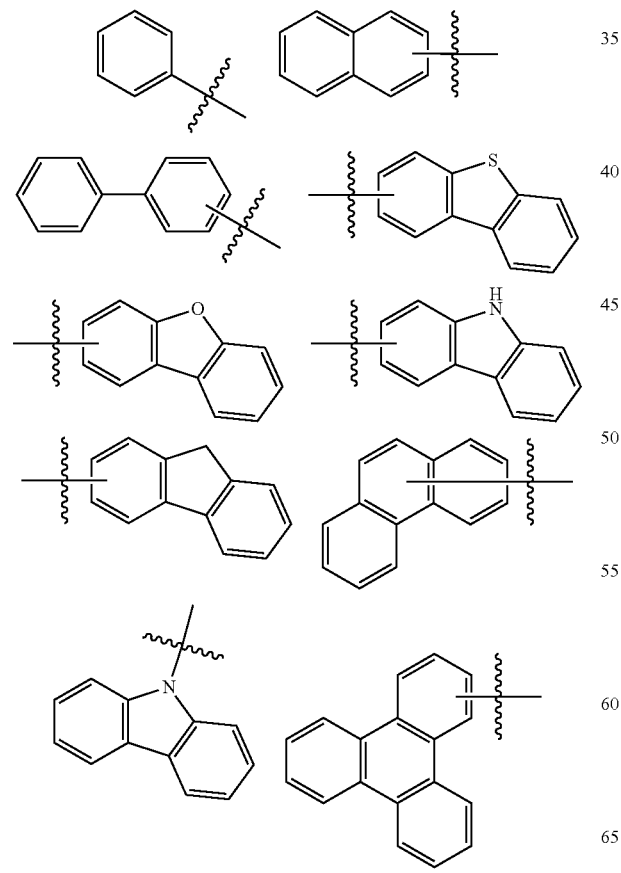

-continued

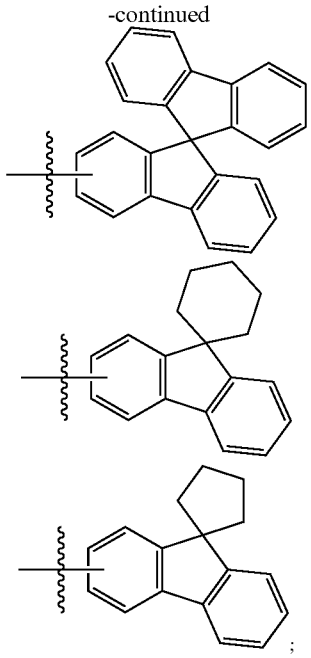

and where the substituted group W has one or two or more substituents, the substituents are independently selected from deuterium, a fluorine, a cyano, a trimethylsilyl, a trifluoromethyl, a methyl, an ethyl, an isopropyl, a tert-butyl, a phenyl, a naphthyl or a biphenyl, and when the number of the substituents is greater than 1, the substituents are the same or different.

4. The organic compound of claim 1, wherein $Ar_1$ and $Ar_2$ are each independently selected from the following groups:

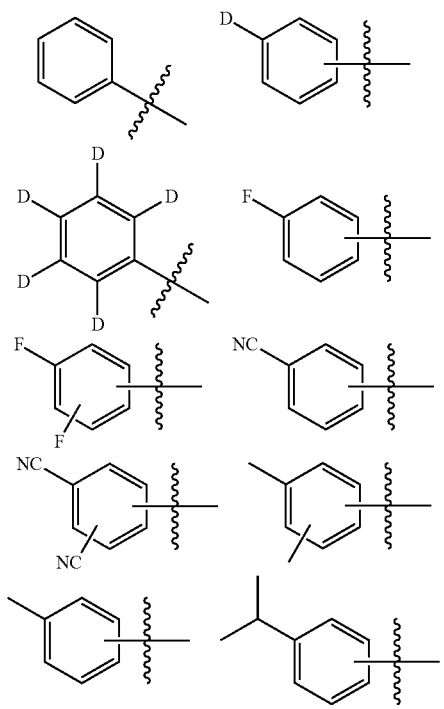

163
-continued
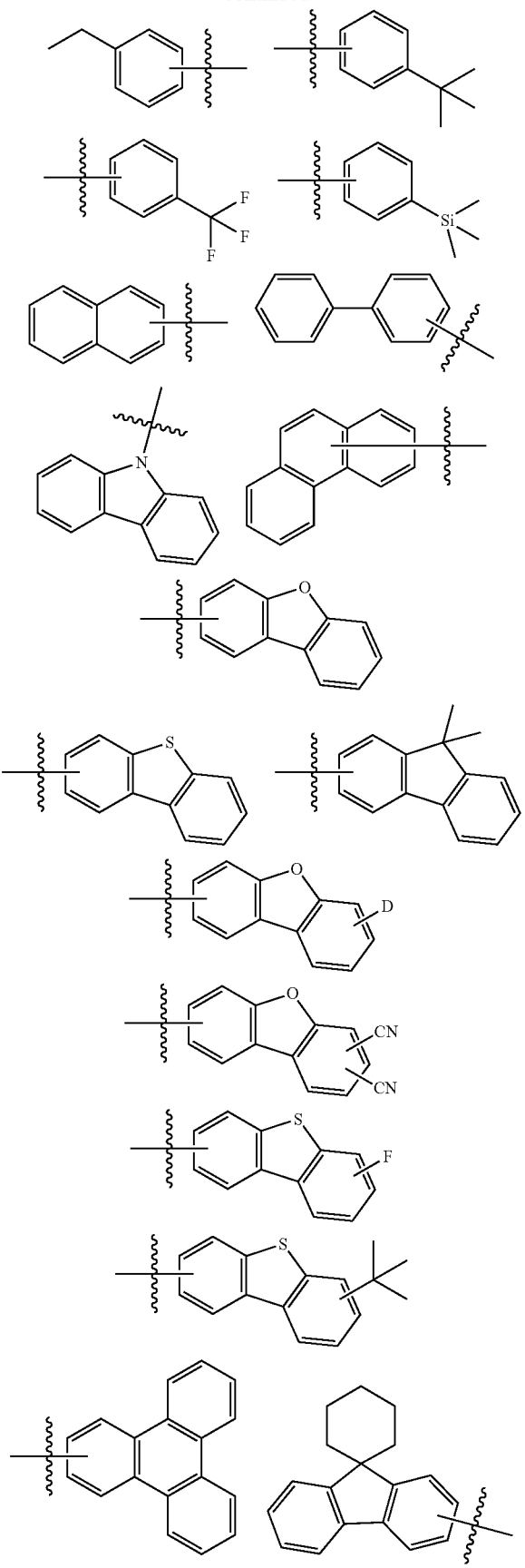
164
-continued
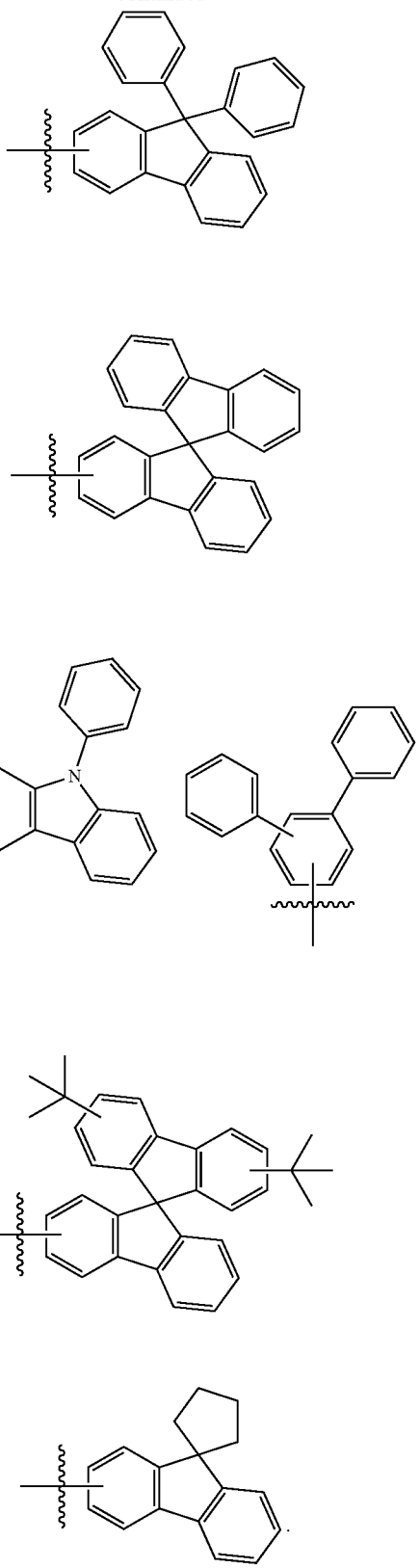
5. The organic compound of claim 1, wherein the organic compound is selected from the group consisting of the following compounds:

1
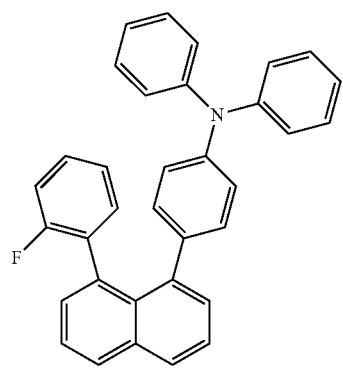
2
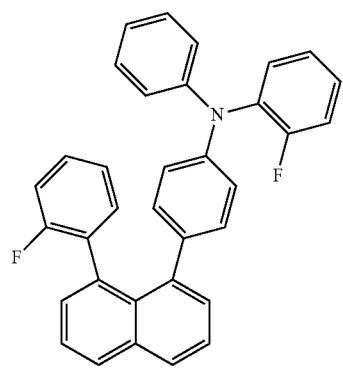
3
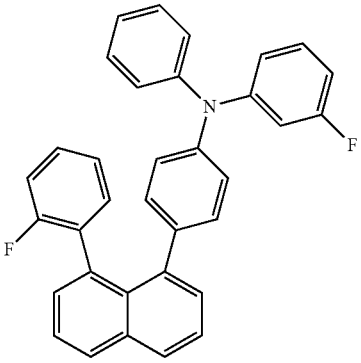
4
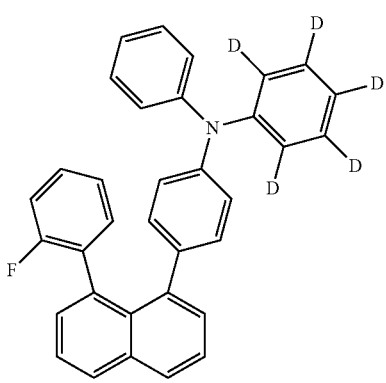
-continued
5
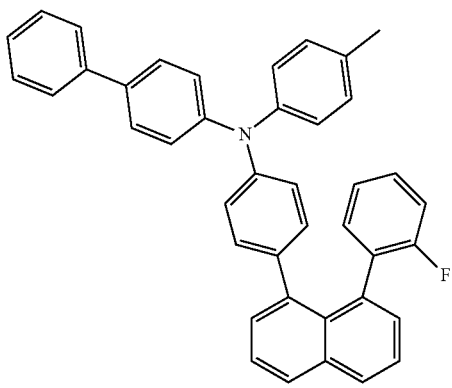
6
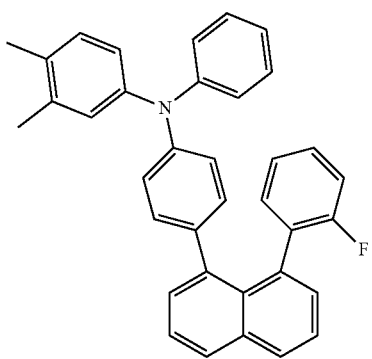
7
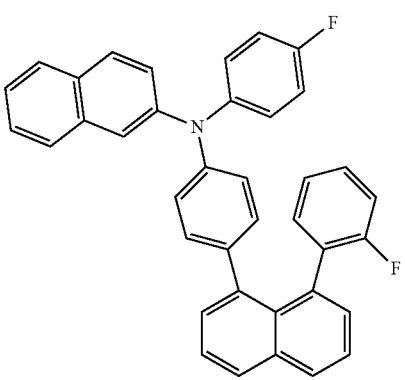
8
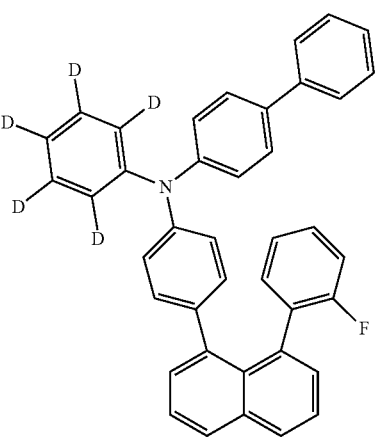

9
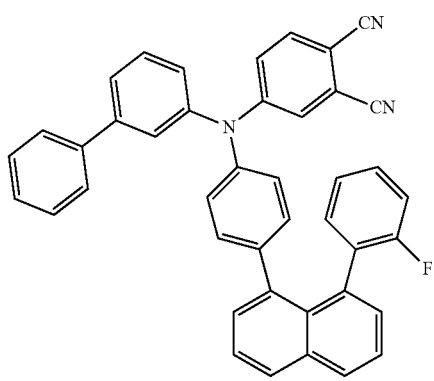
10
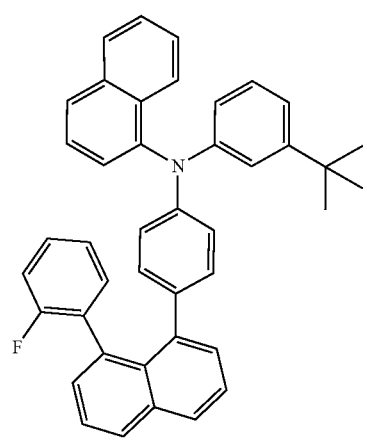
11
13
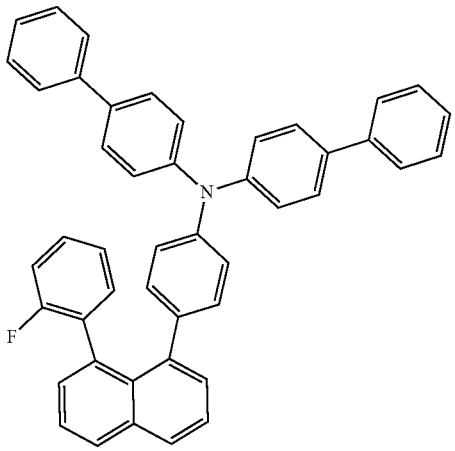
14
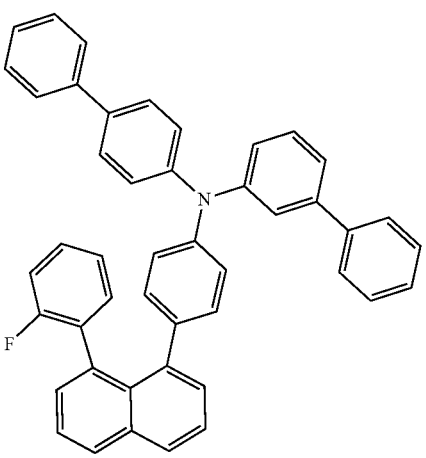
12
15
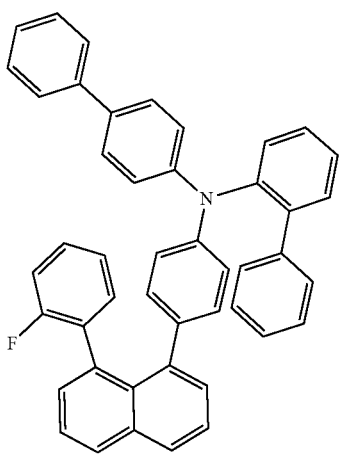

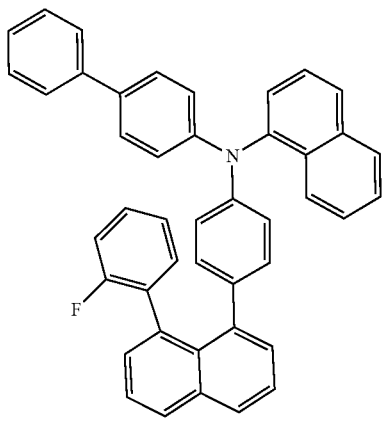
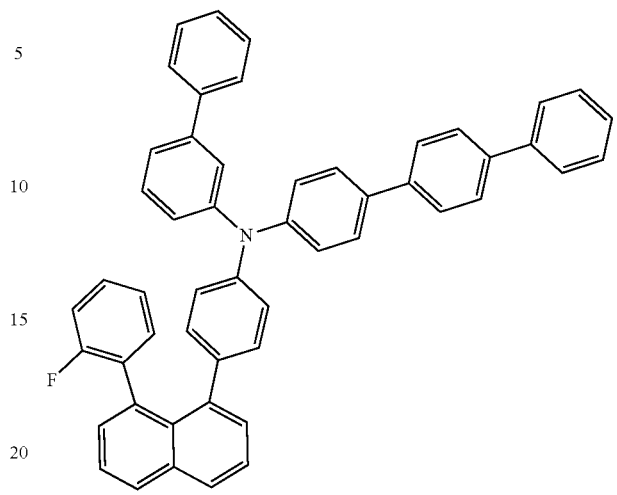
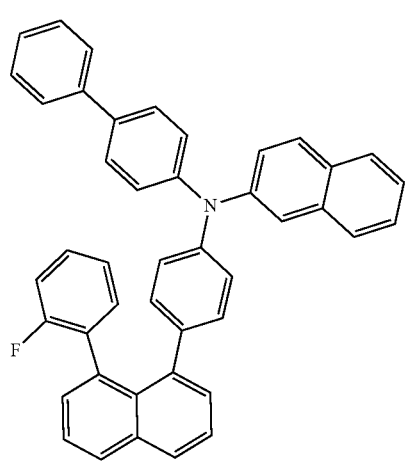
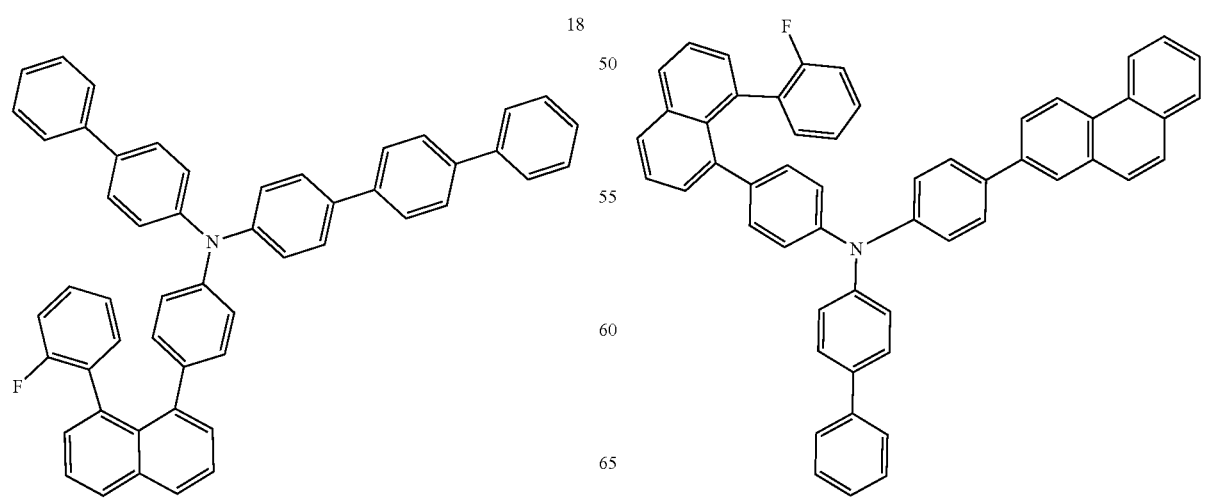

171
-continued
22
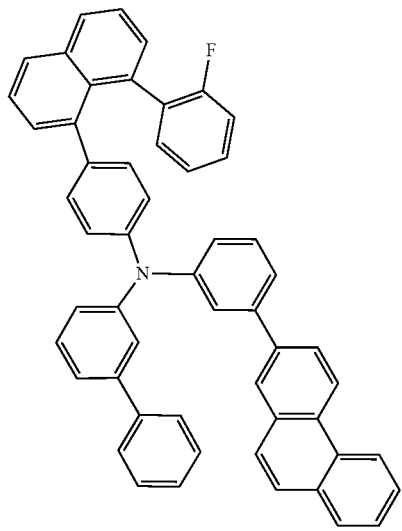
23
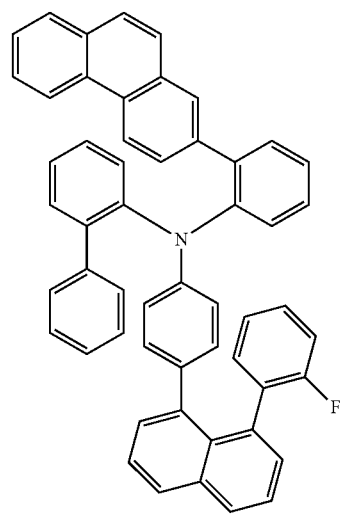
24
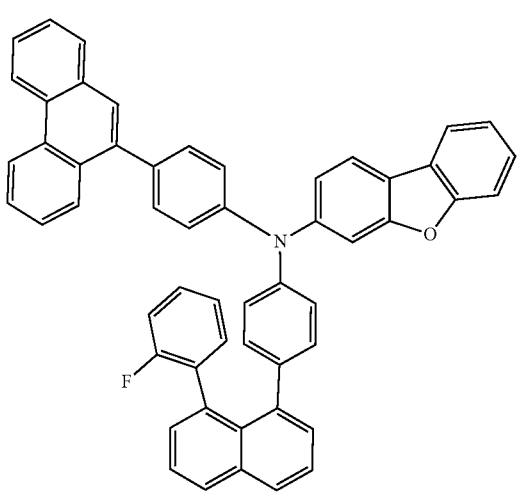
172
-continued
25
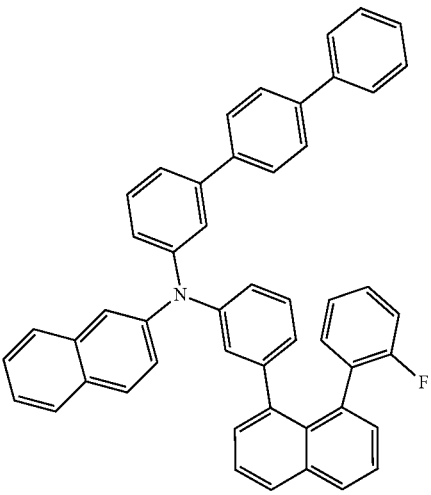
26
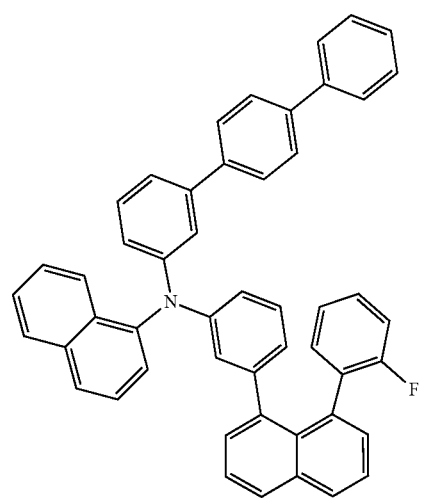
27
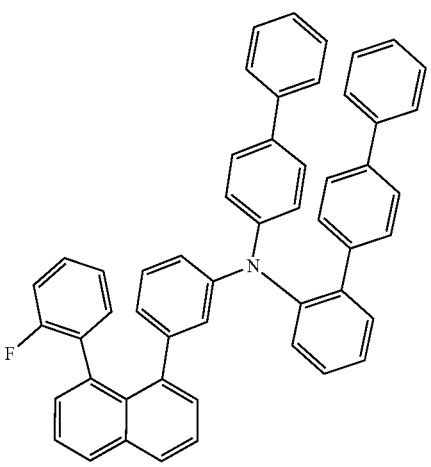

28
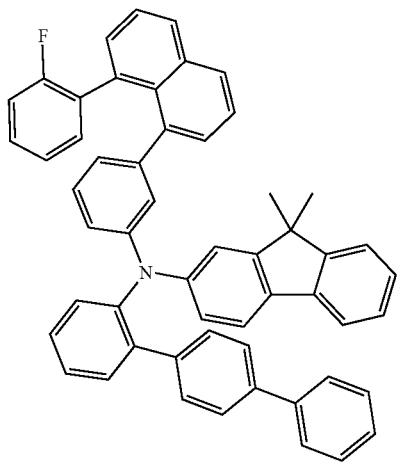
29
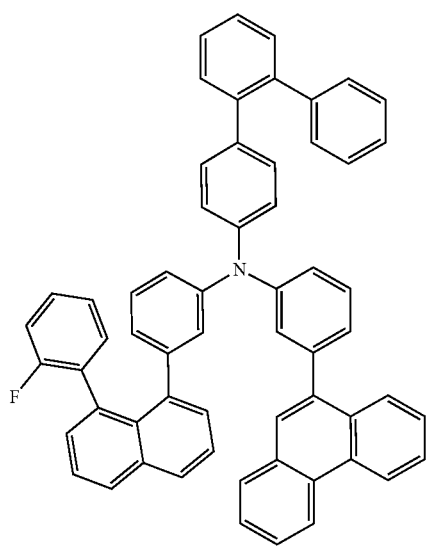
30
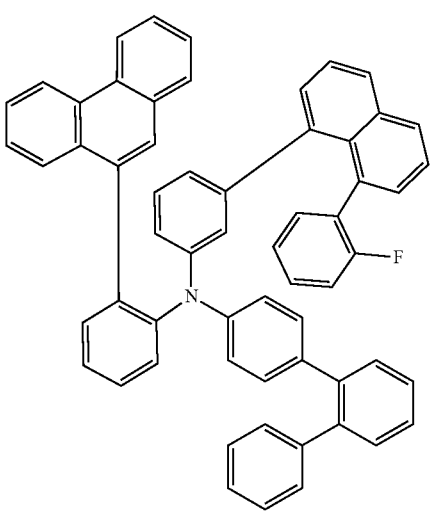
31
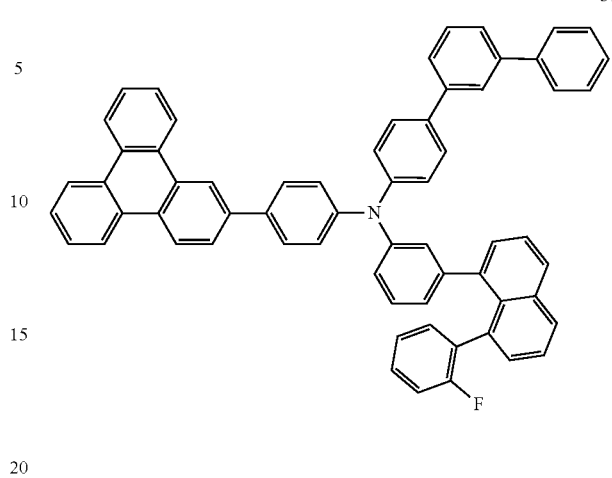
32
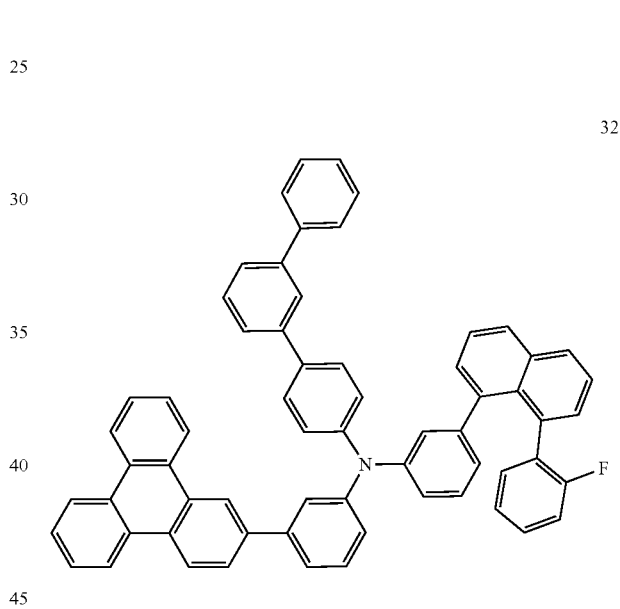
33
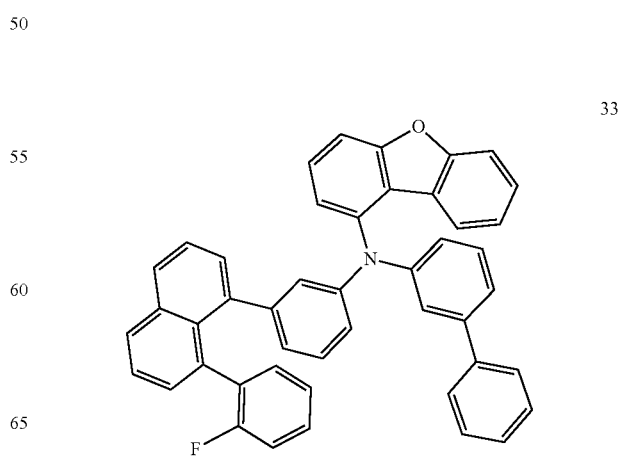

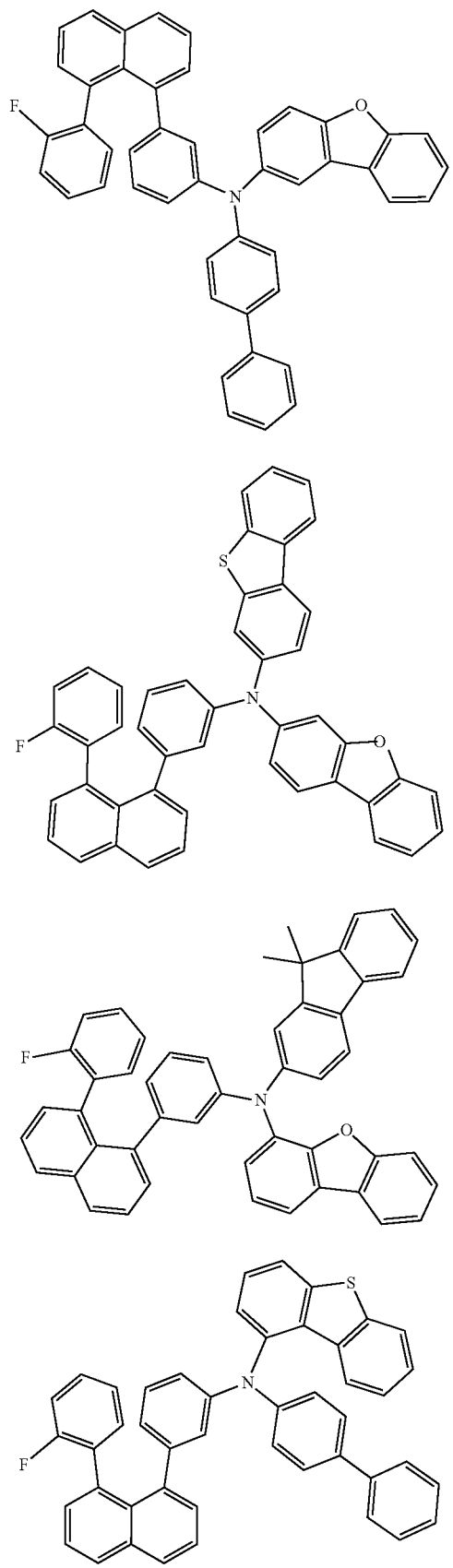
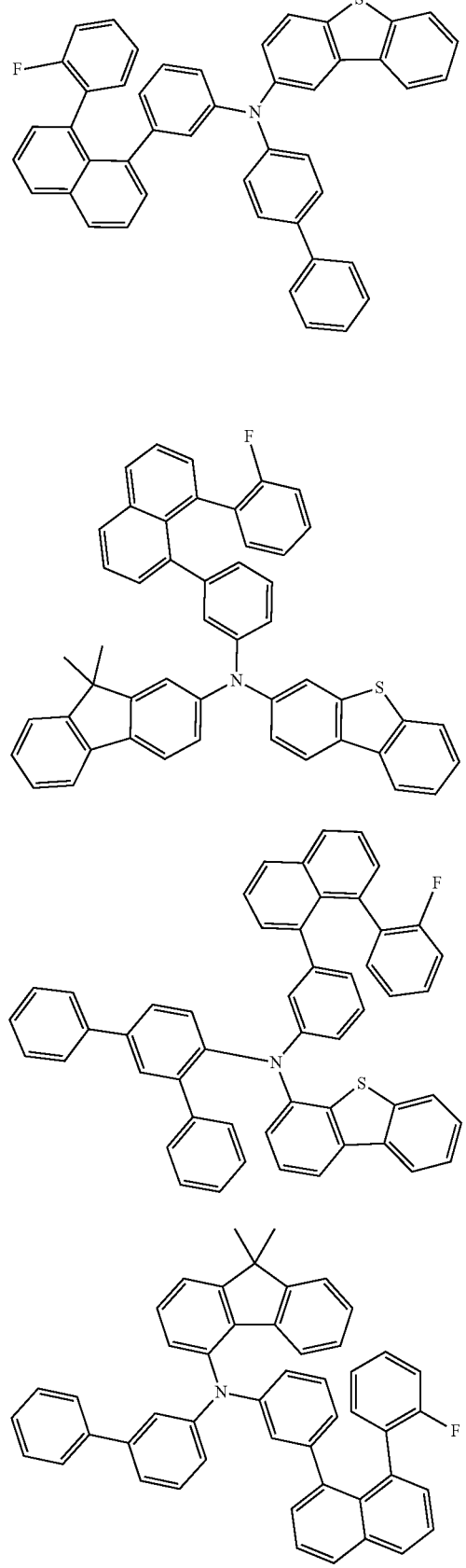

42
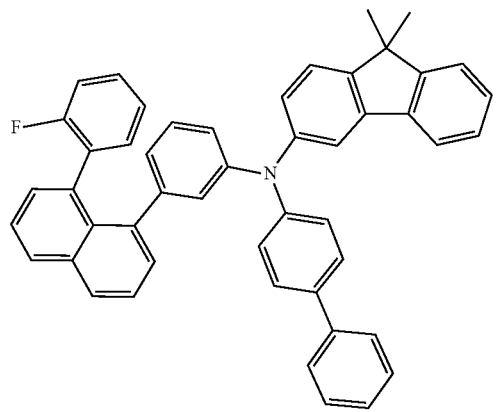
43
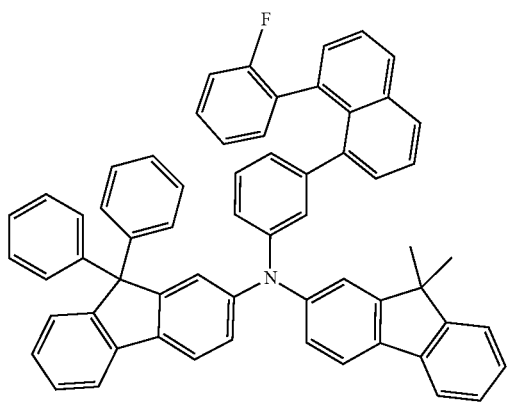
45
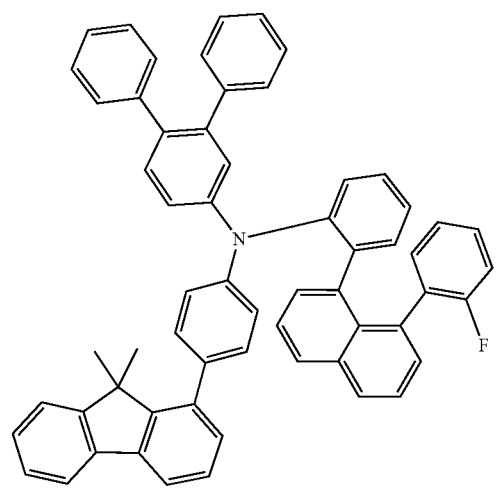
46
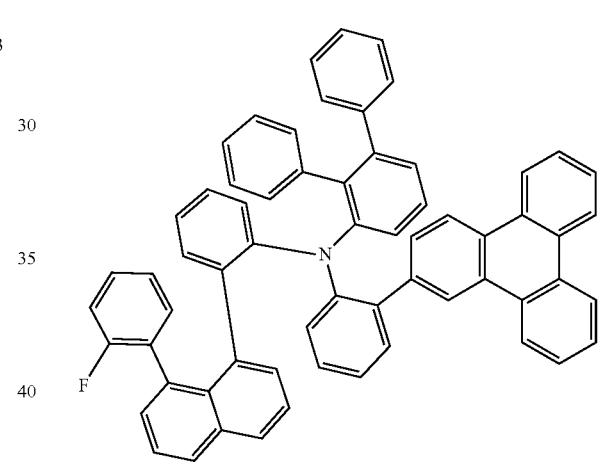
44
47
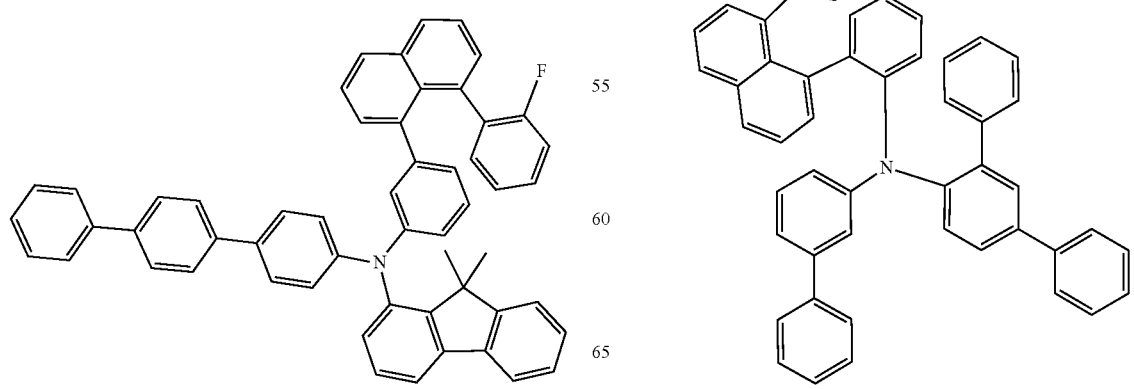

48
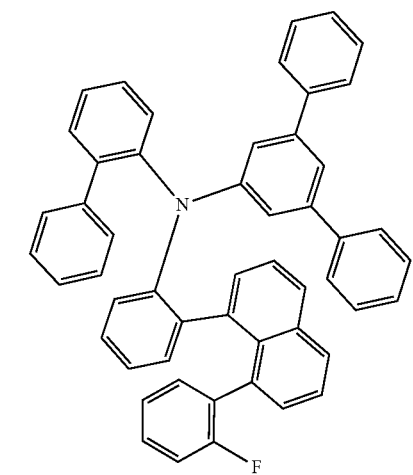
49
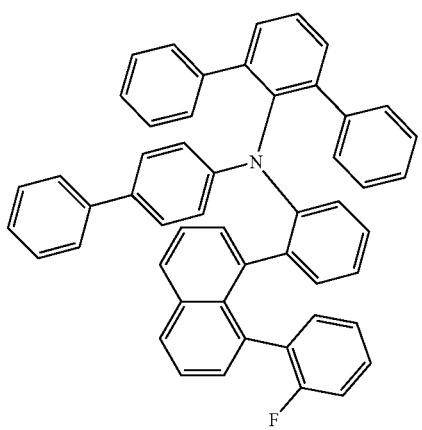
50
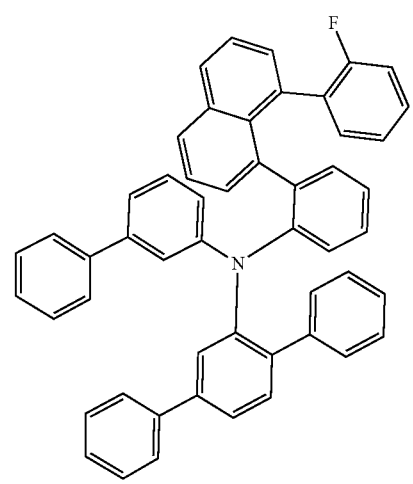
51
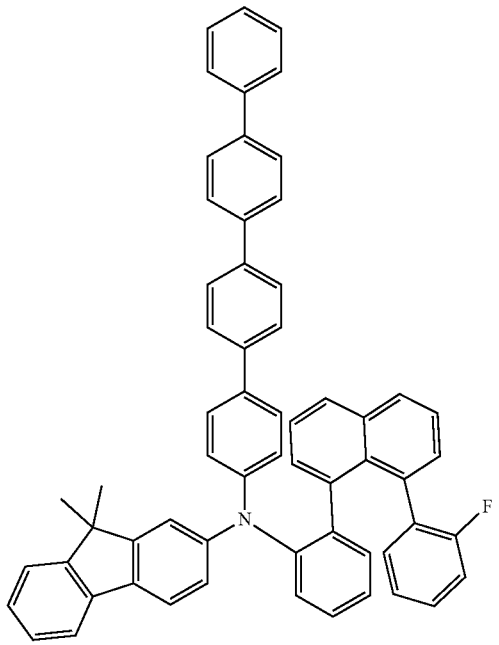
52
53
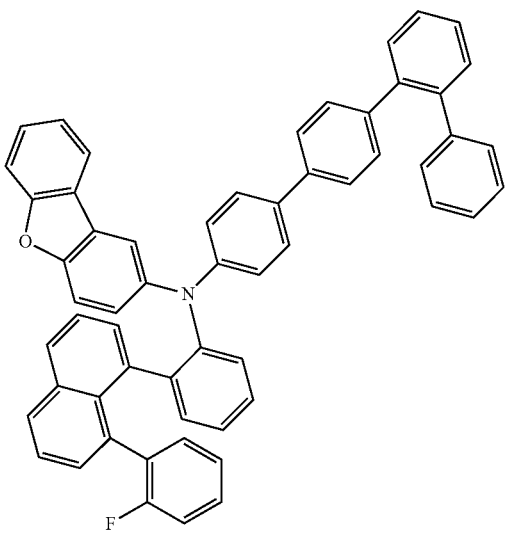

54
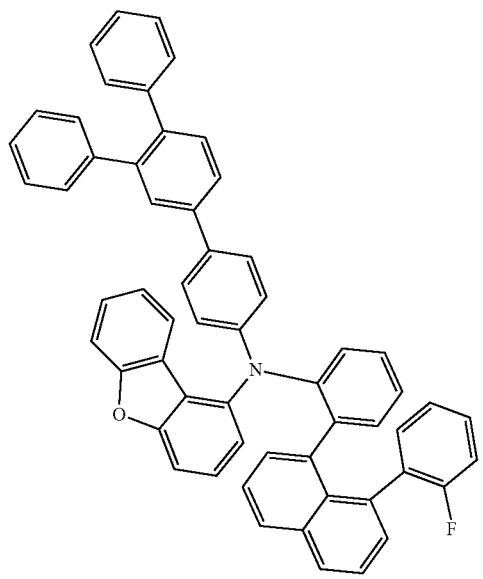
55
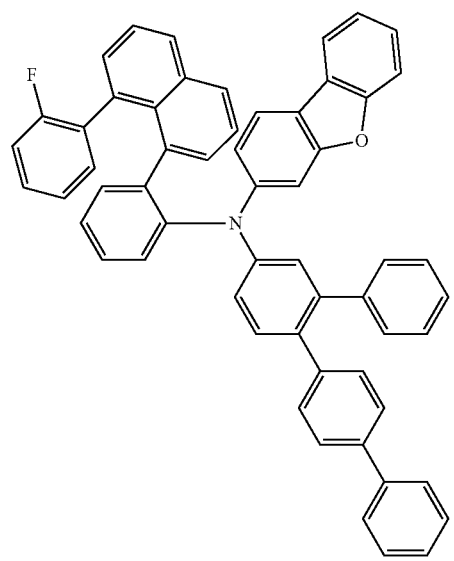
56
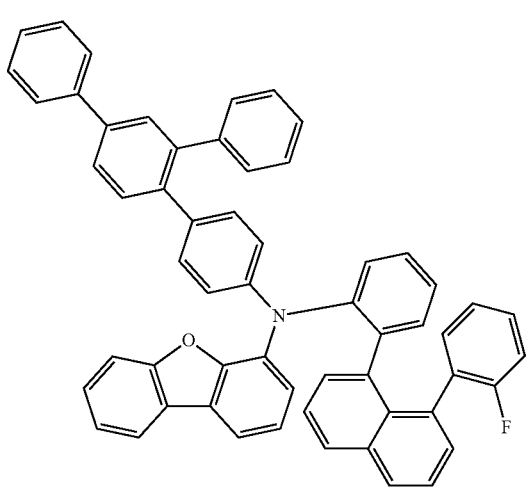
57
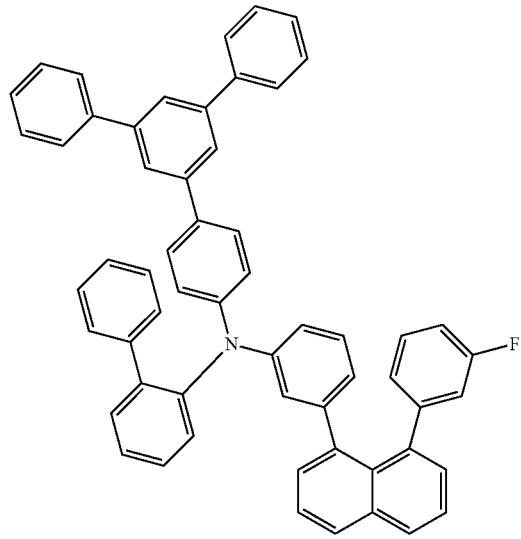
58
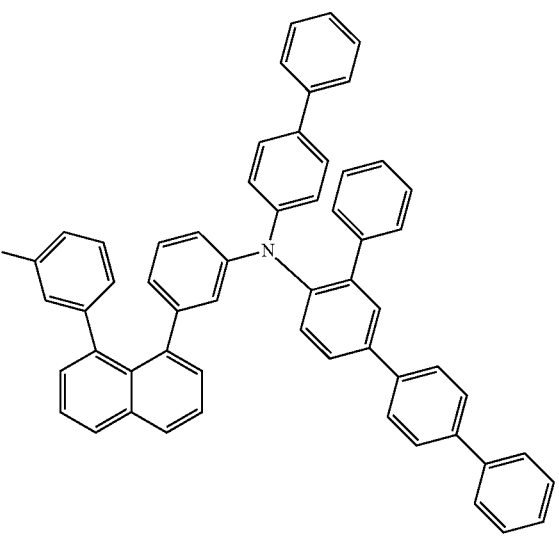
59
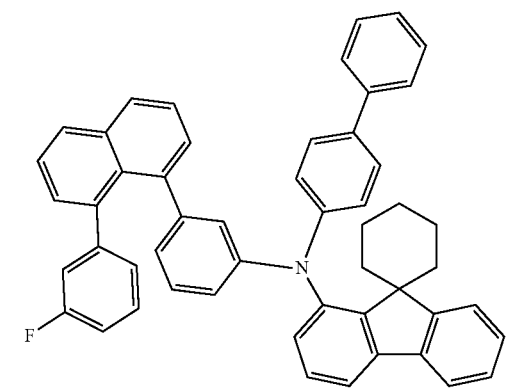

60
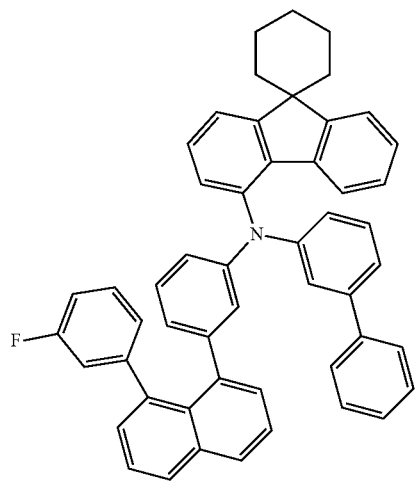
61
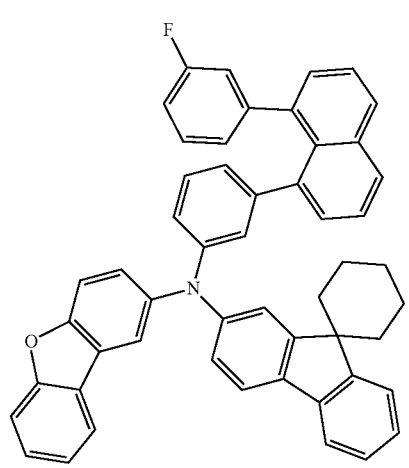
62
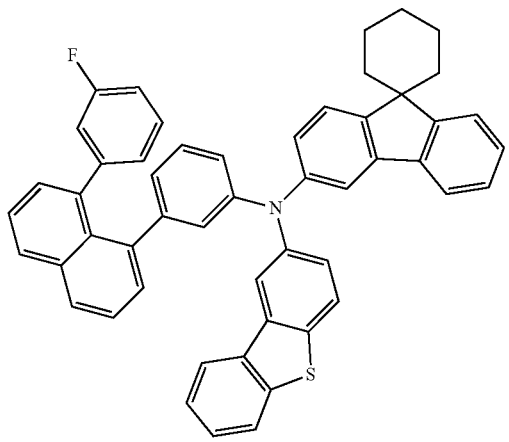
63
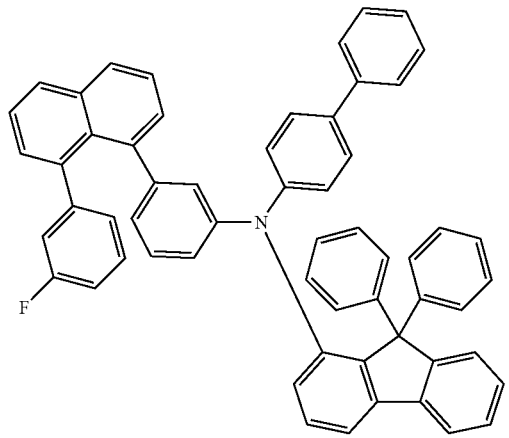
64
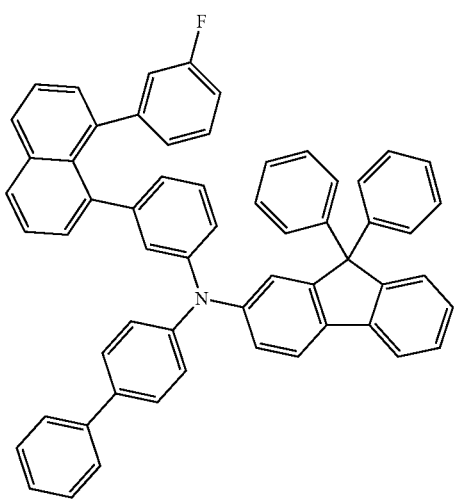
65
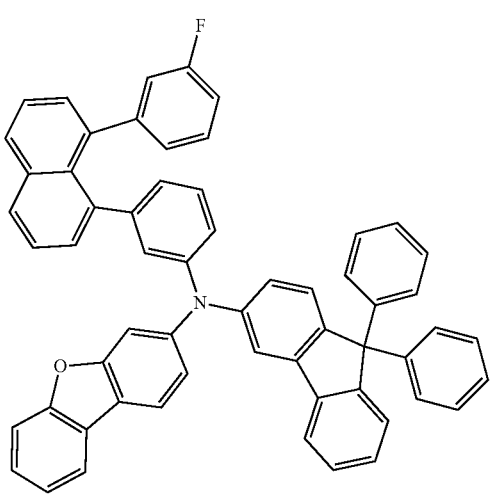

66
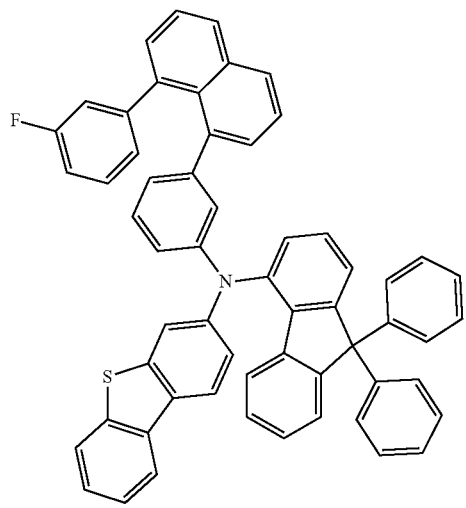
67
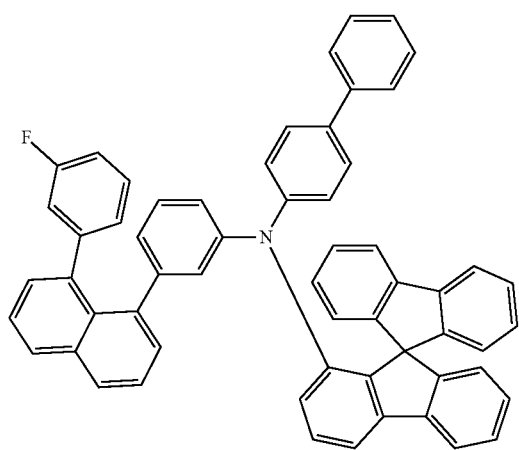
68
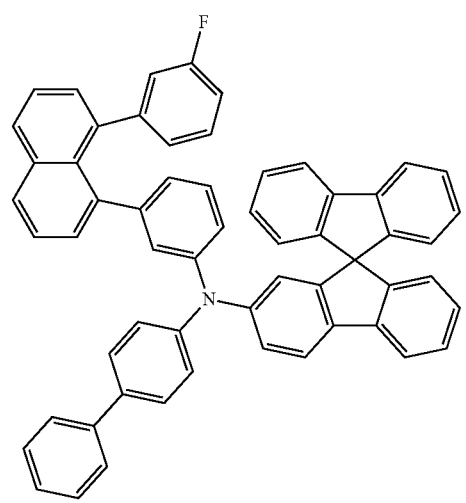
69
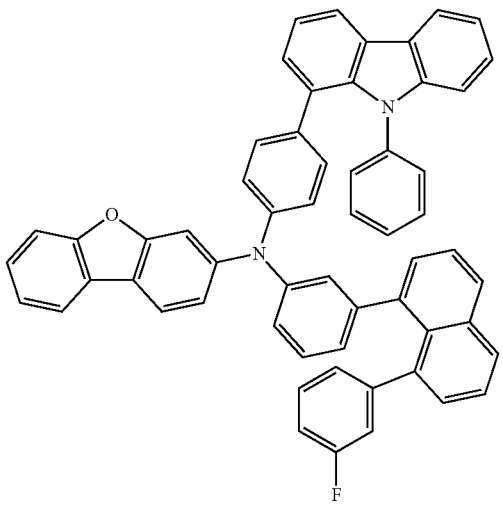
70
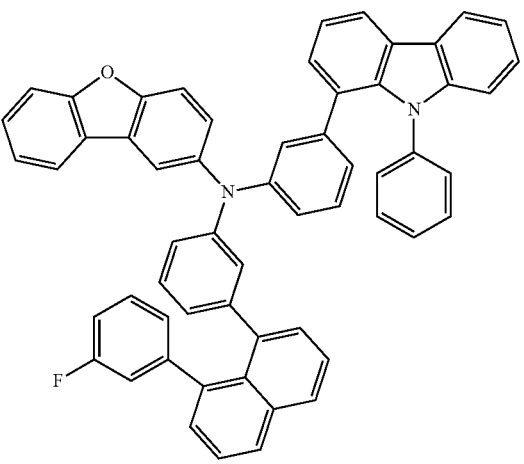
71
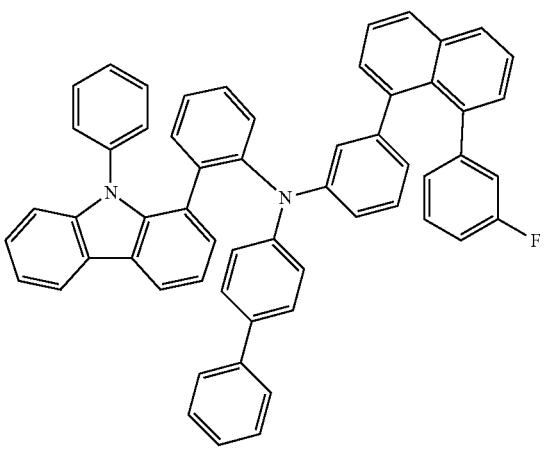

187 188
-continued -continued
72
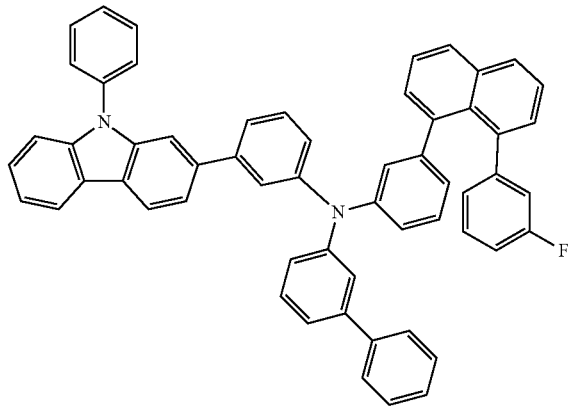
75
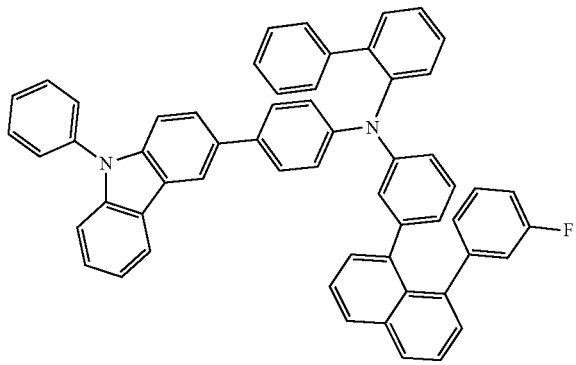
73
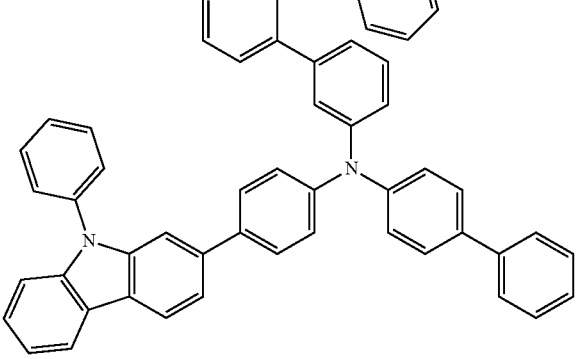
76
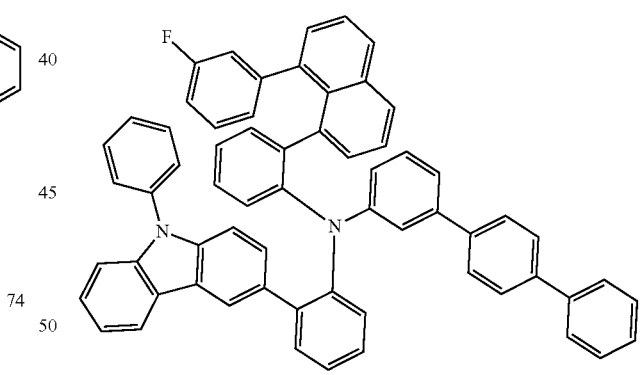
77
74
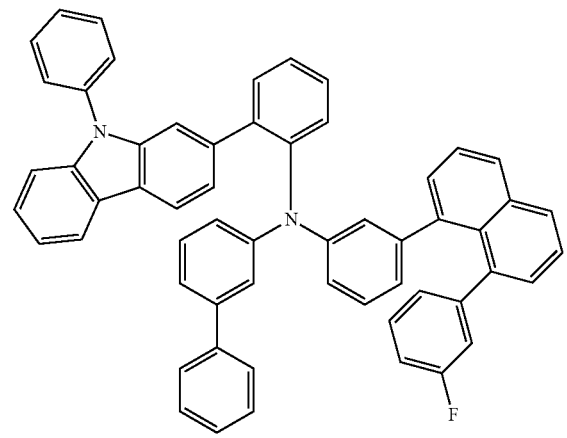
78
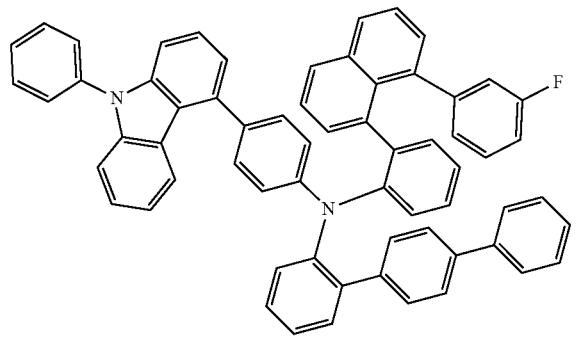

79
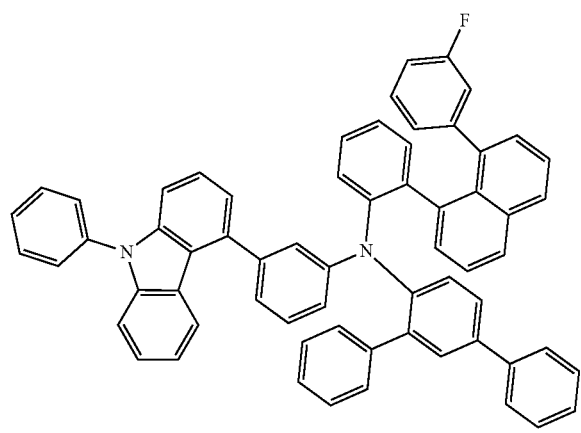
82
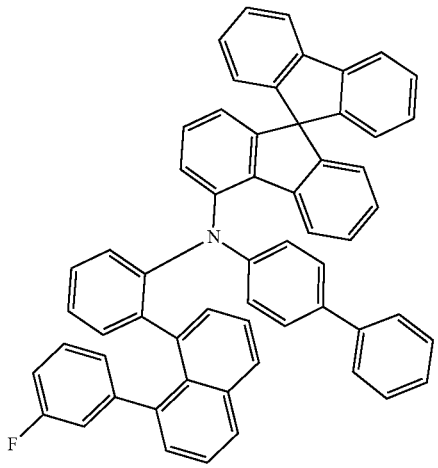
80
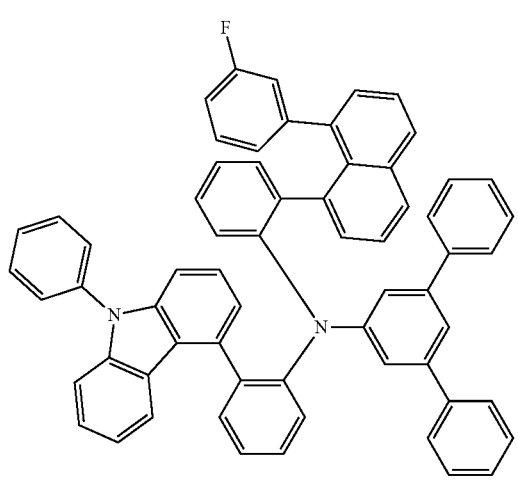
83
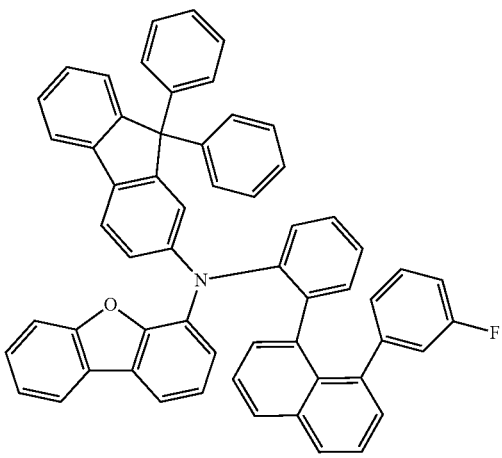
81
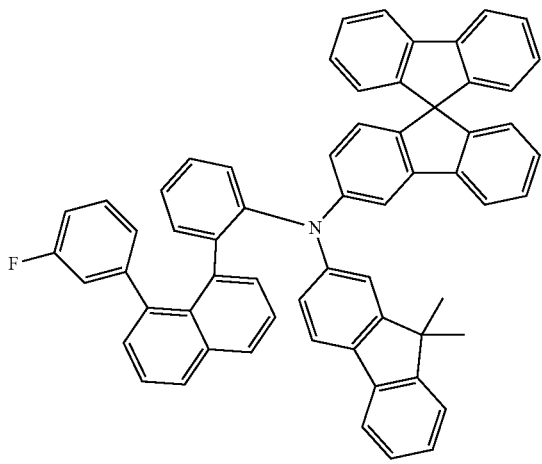
84
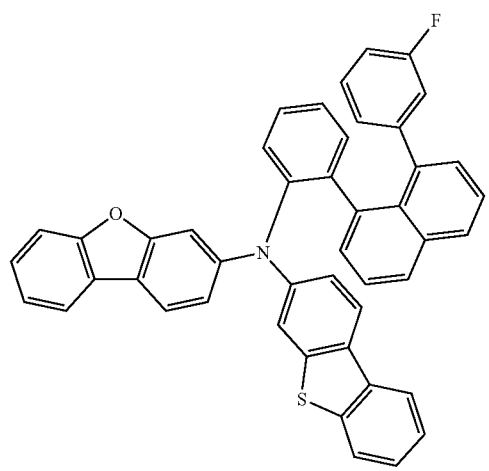

85
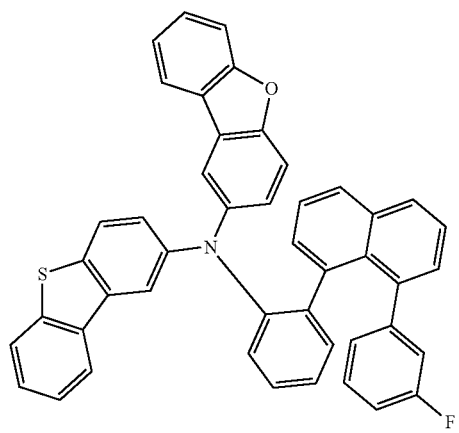
86
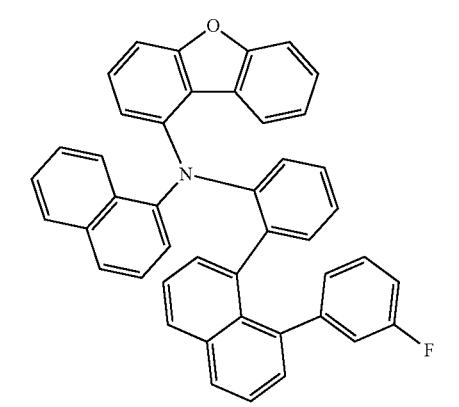
87
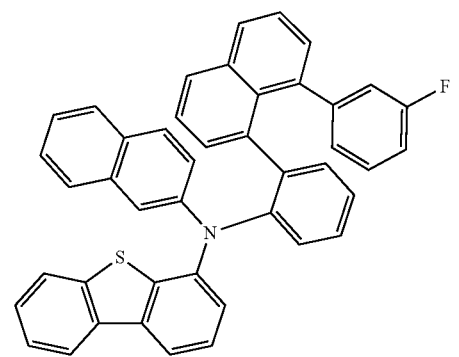
88
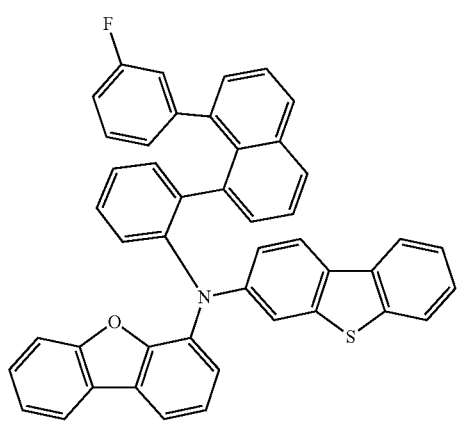
89
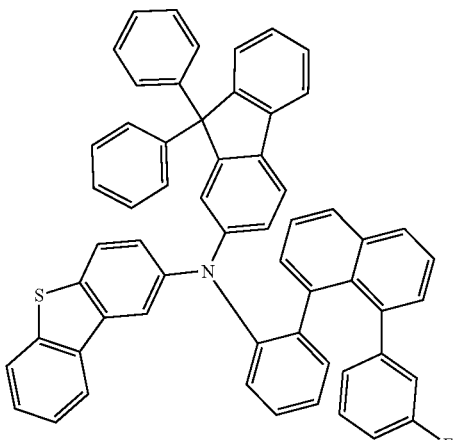
90
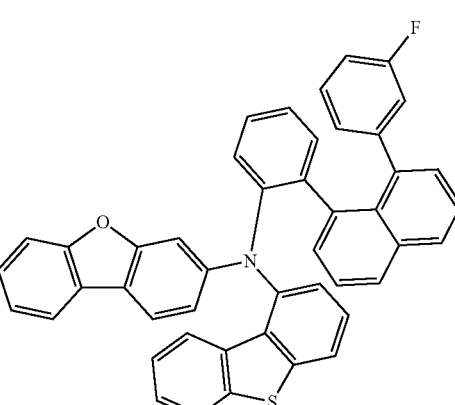
91
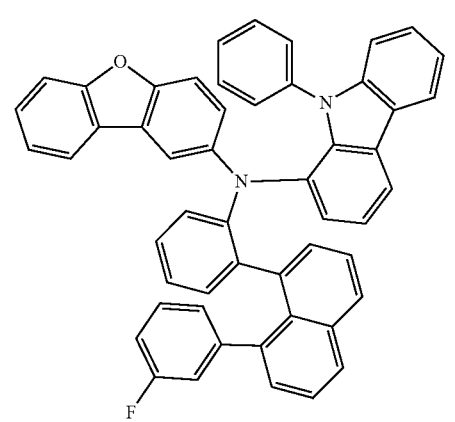

92
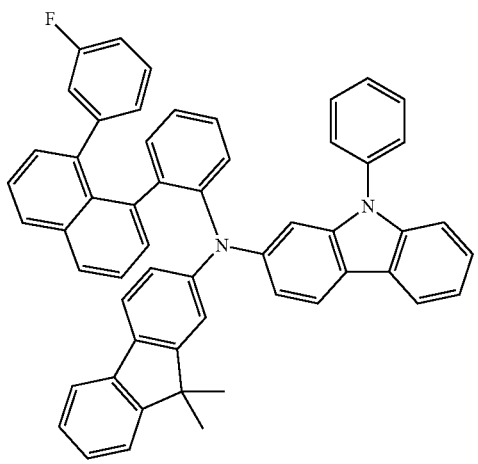
93
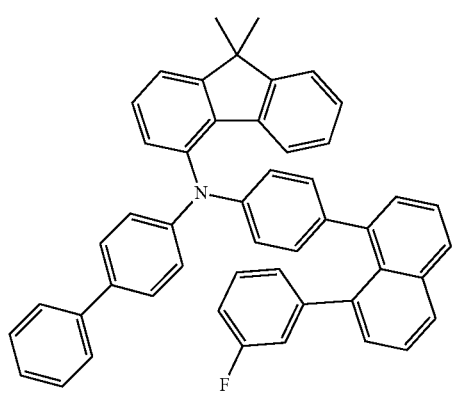
94
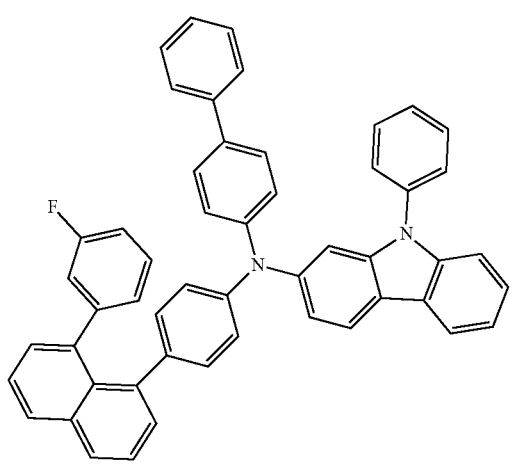
95
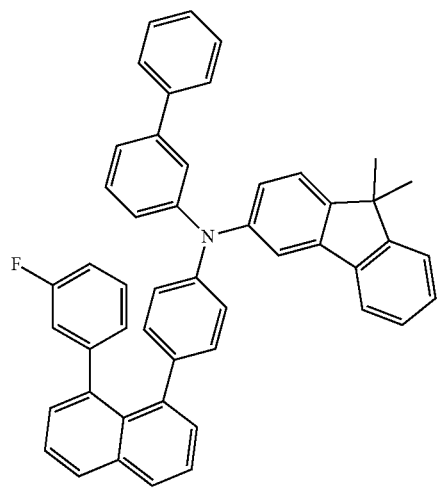
96
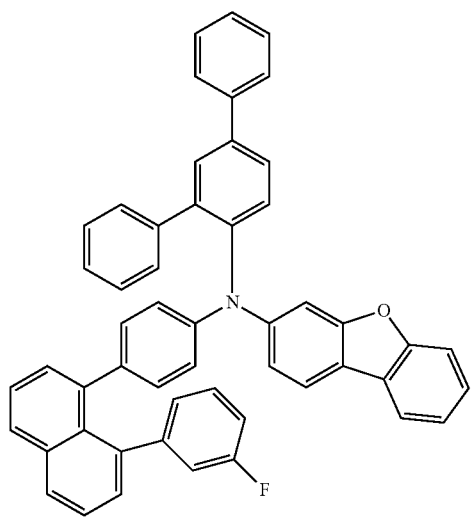
97
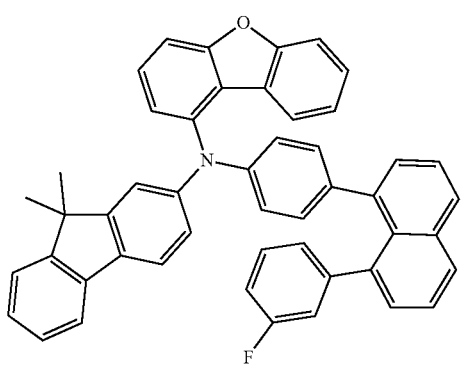

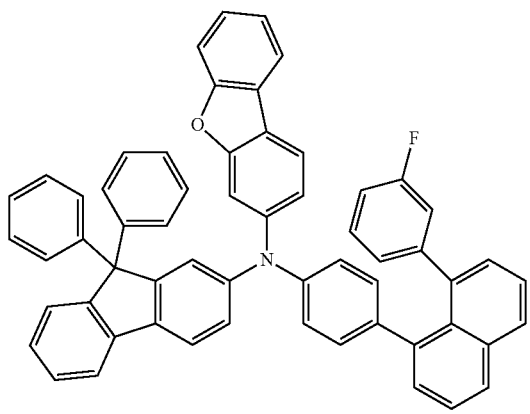
98
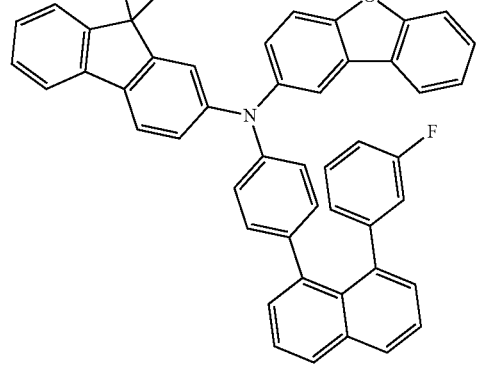
99
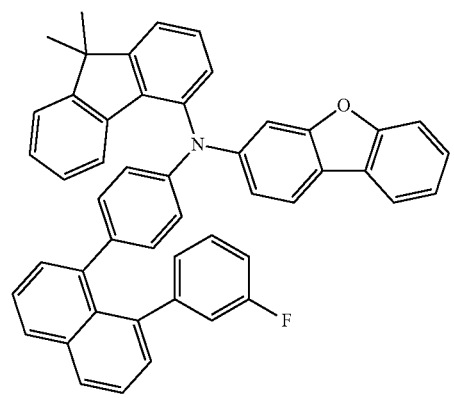
100
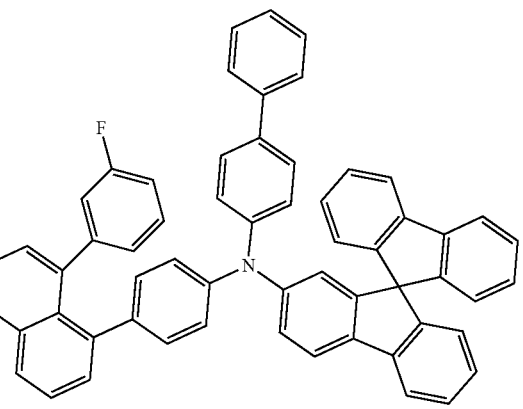
101
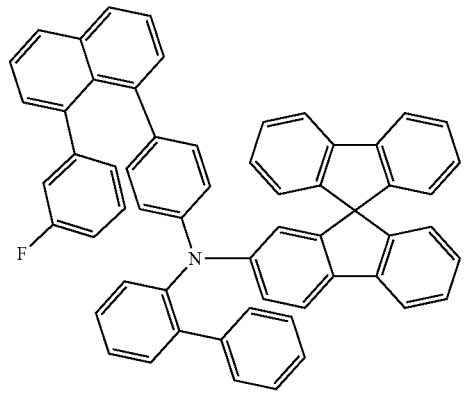
102
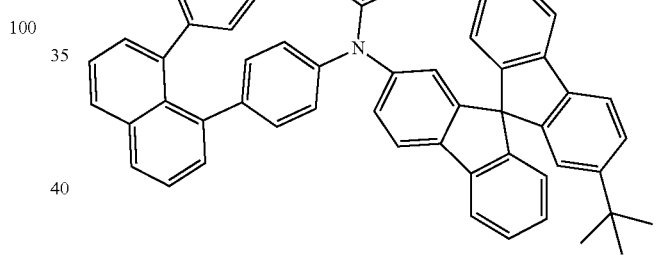
103
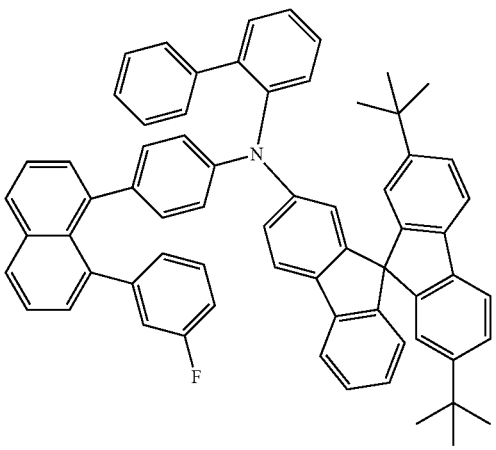
104

105
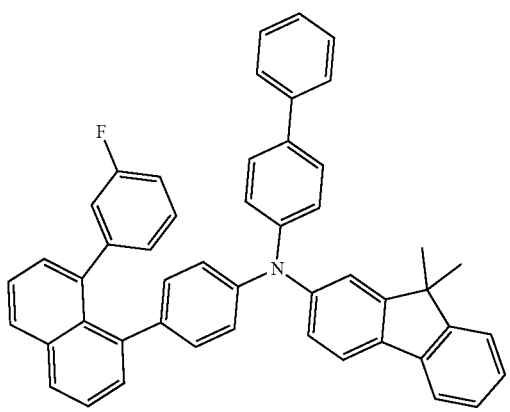
106
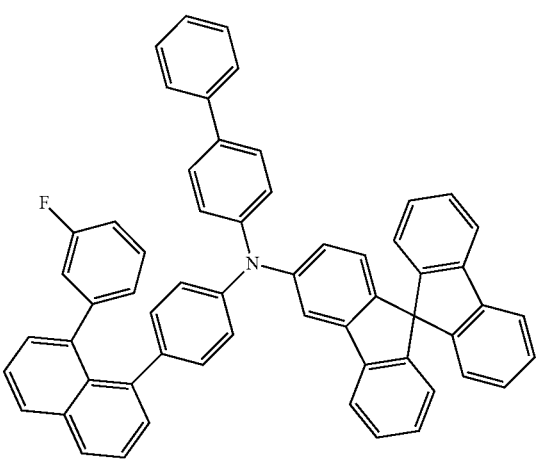
107
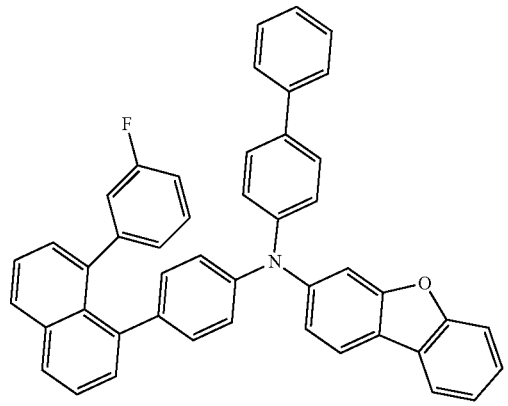
108
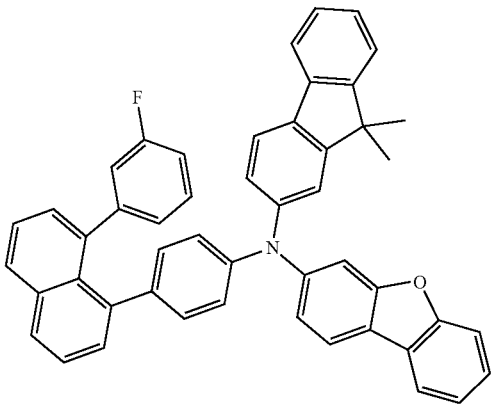
109
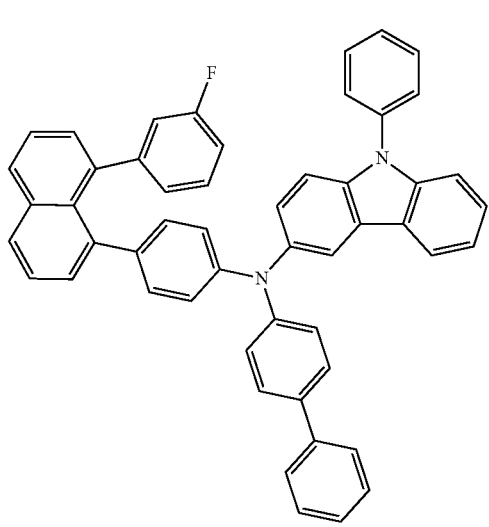
110
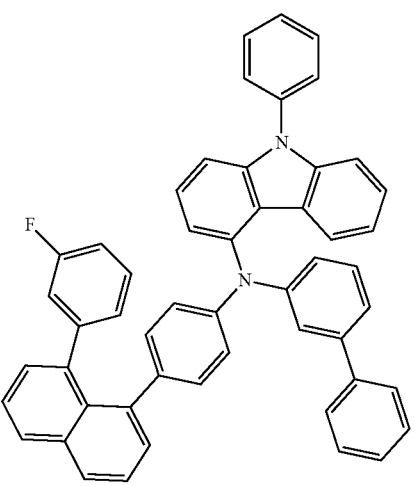

111
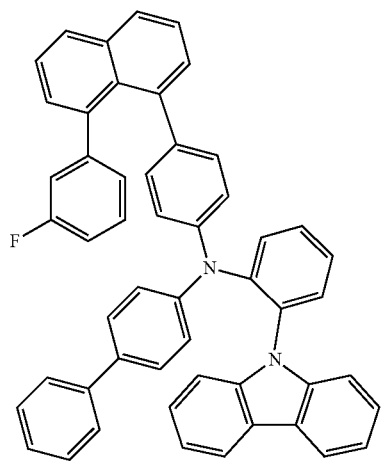
112
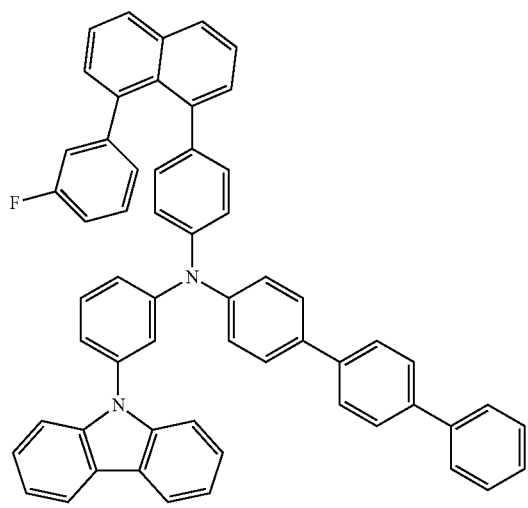
113
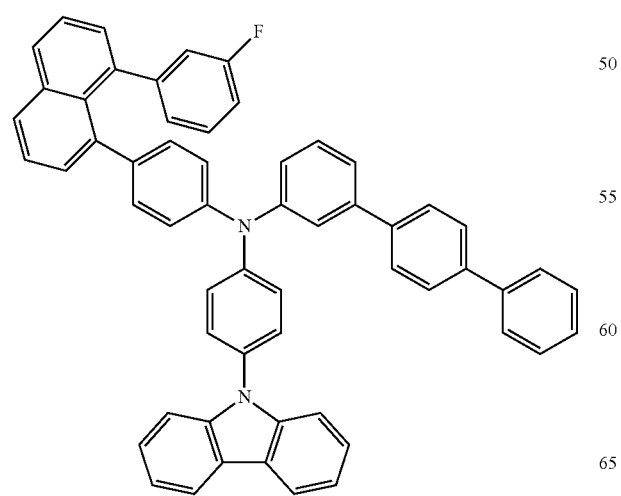
114
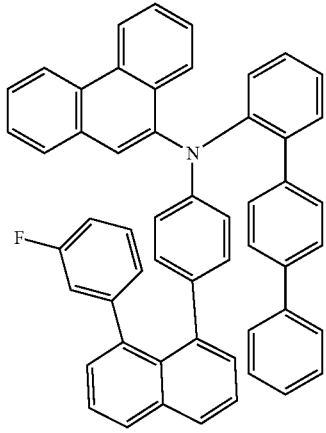
115
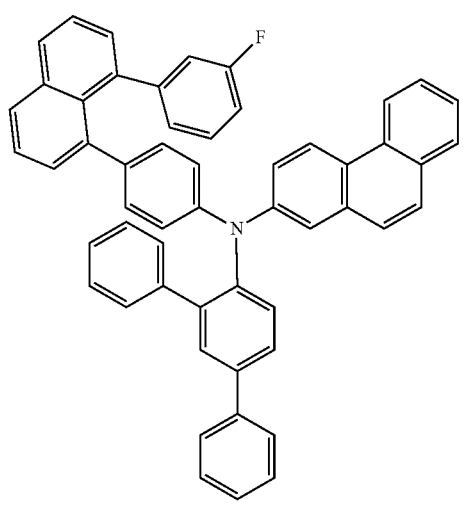
116
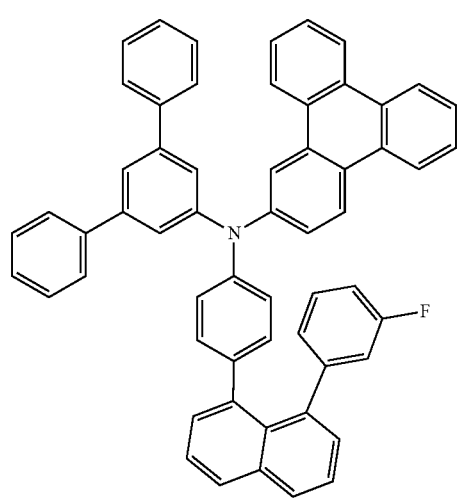

201
-continued
117
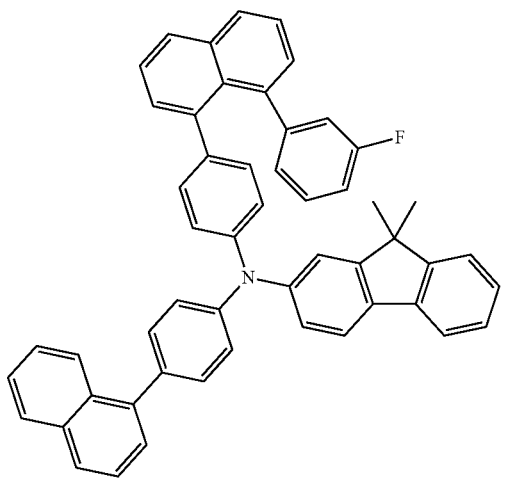
118
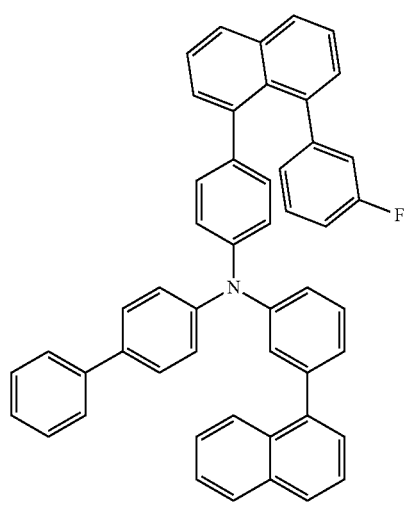
119
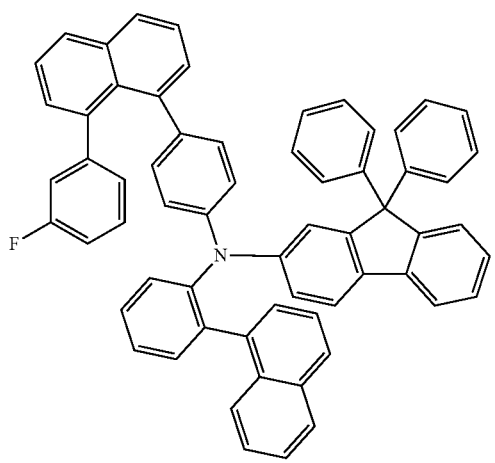
202
-continued
120
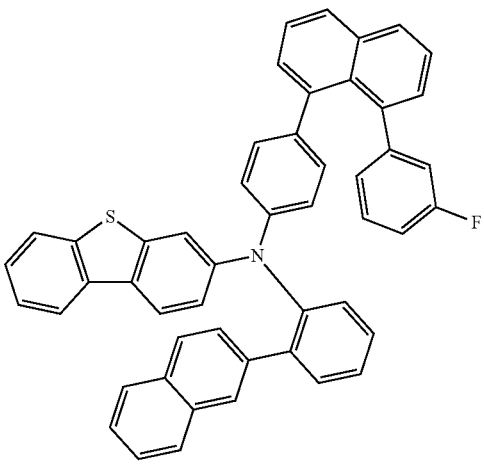
121
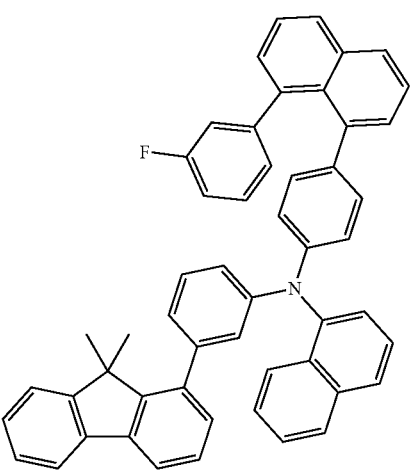
122

123
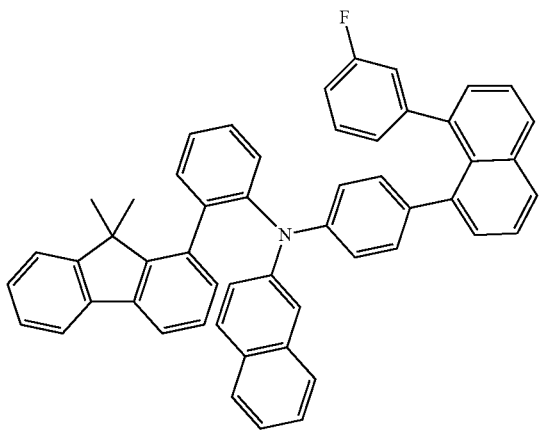
124
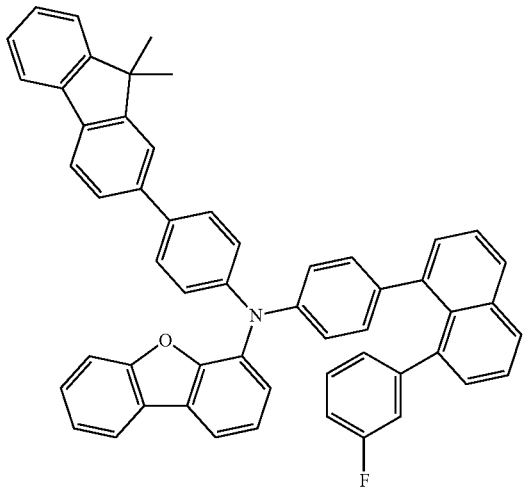
125
126
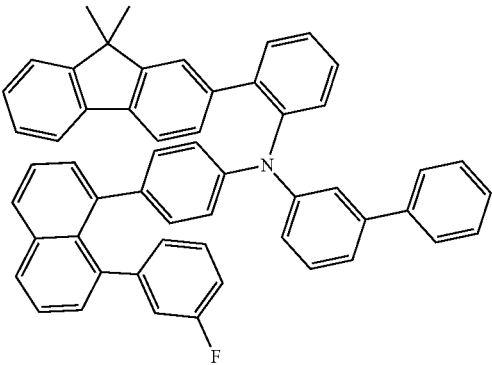
127
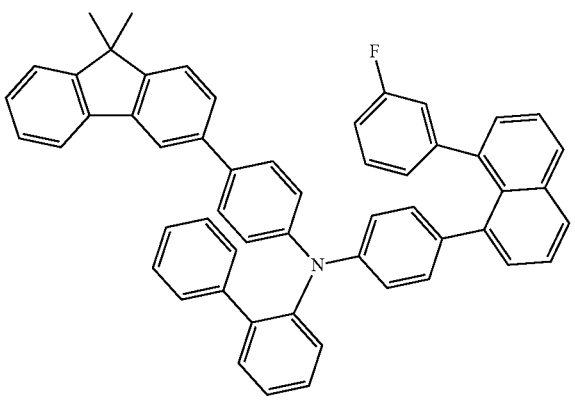
128
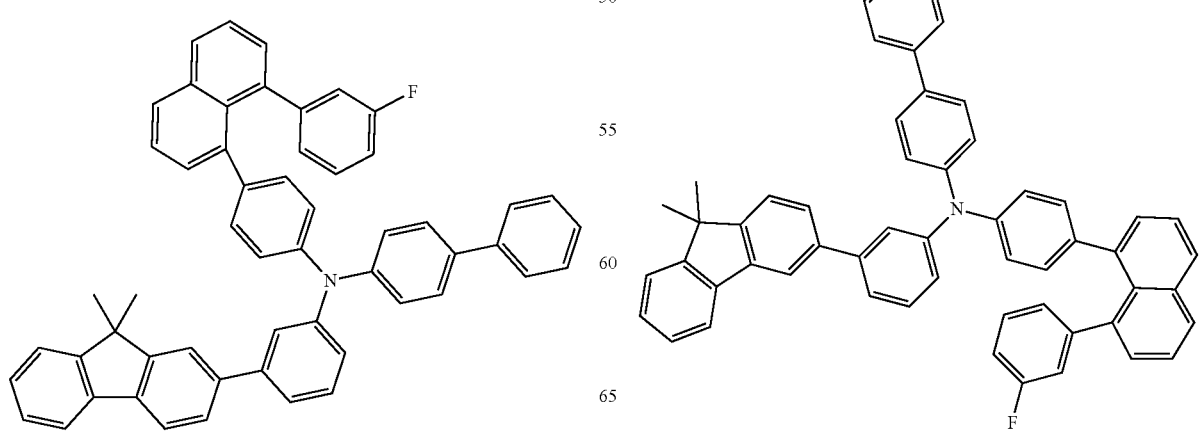

205
-continued
129
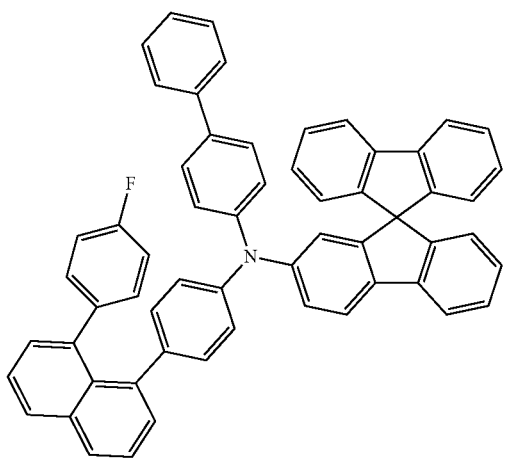
130
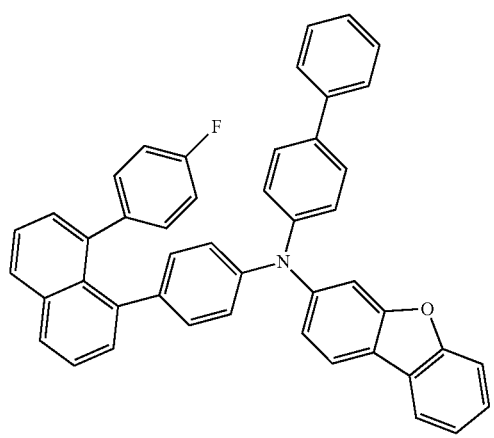
131
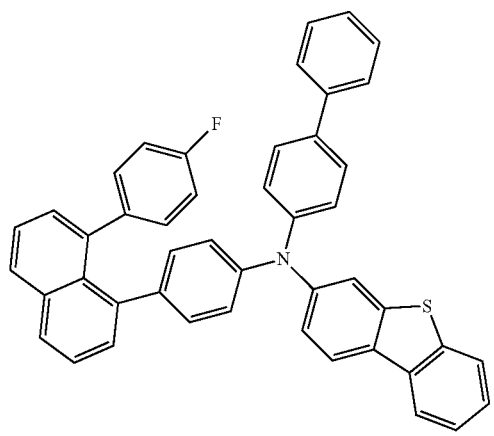
206
-continued
132
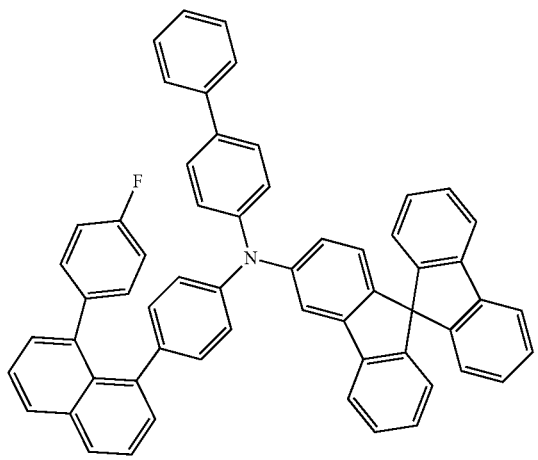
133
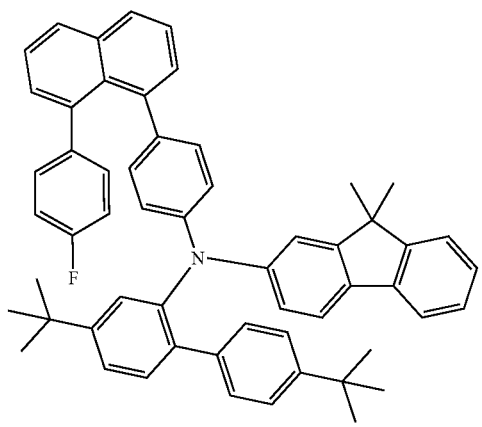
134

135
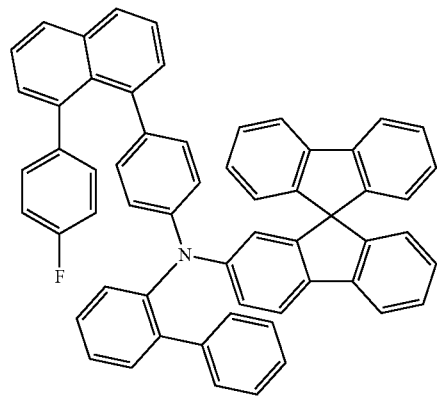
136
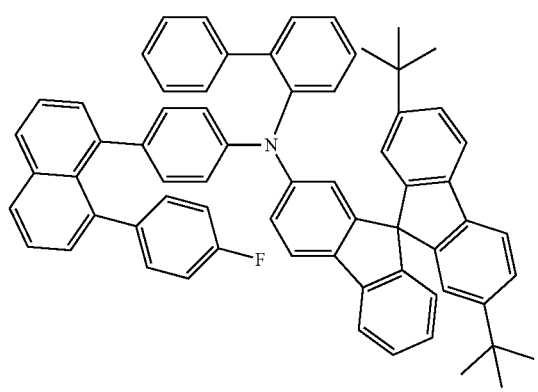
137
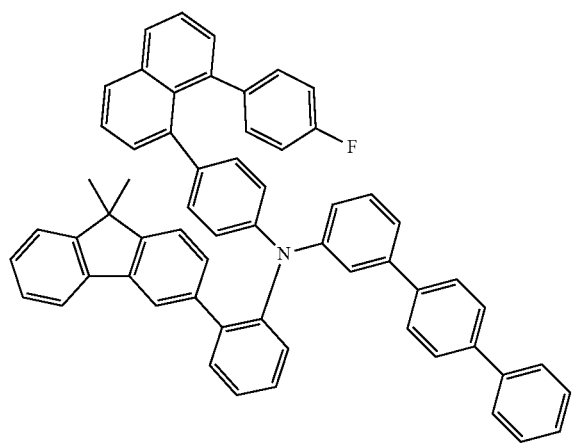
138
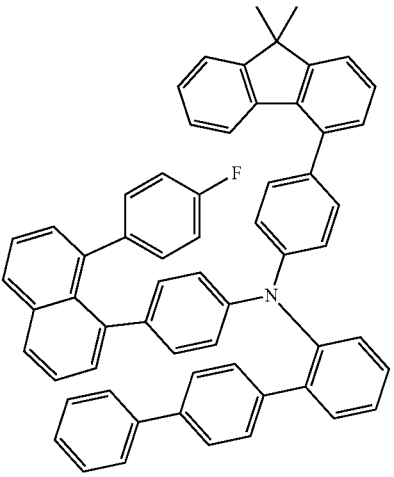
139
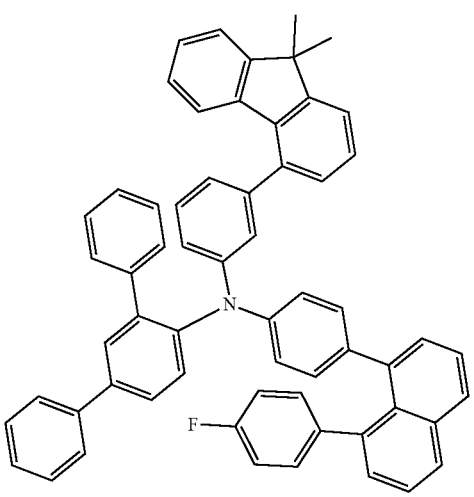
140
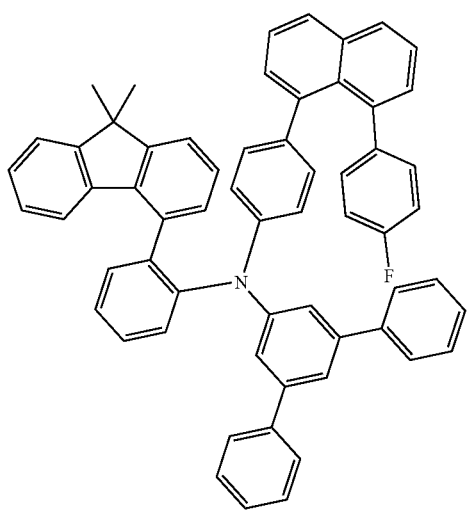

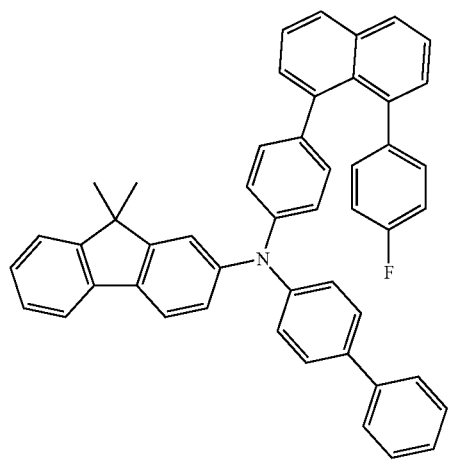
141
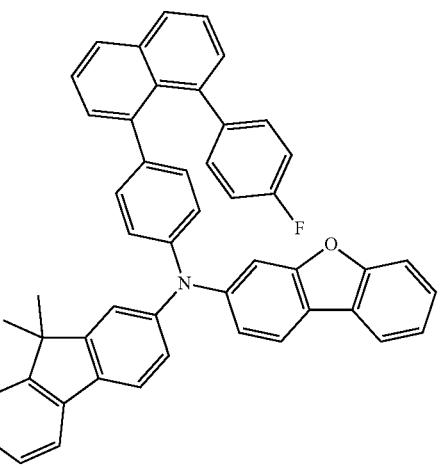
144
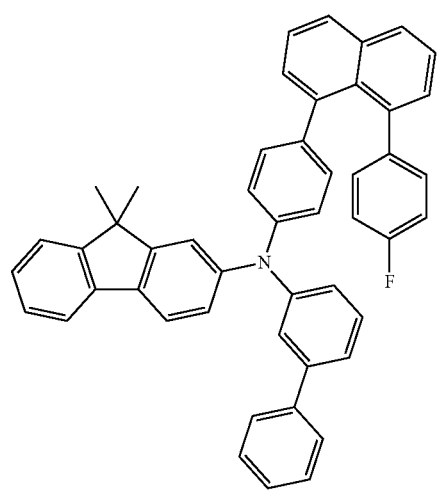
142
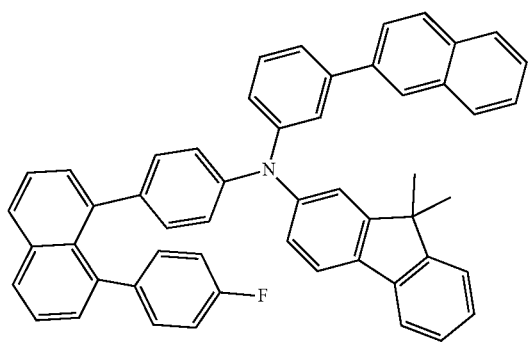
145
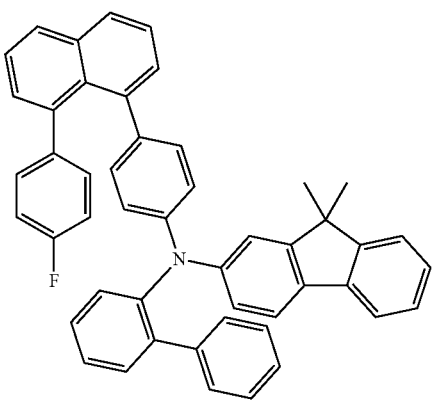
146
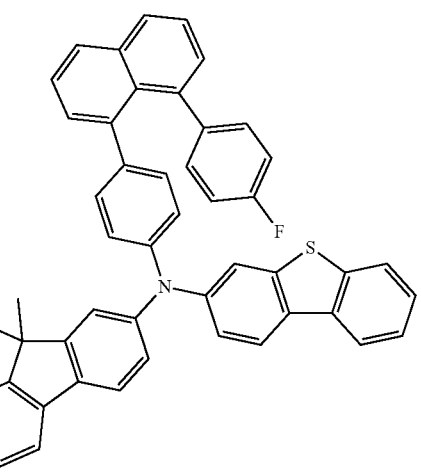
143
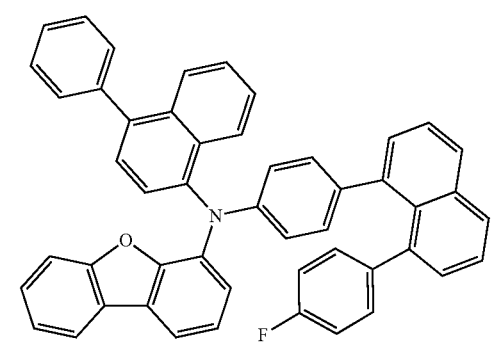
147

148
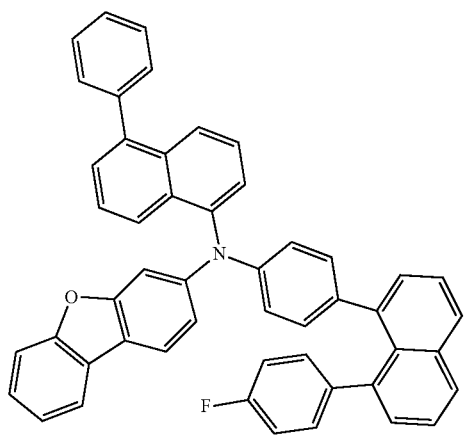
149
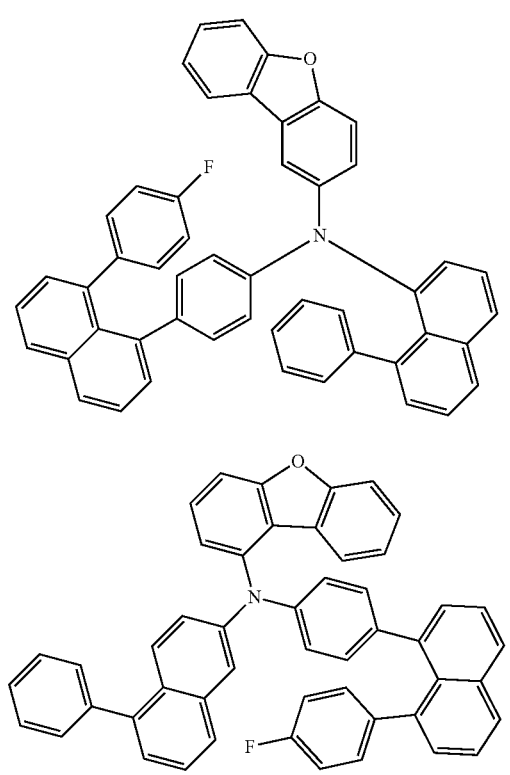
150
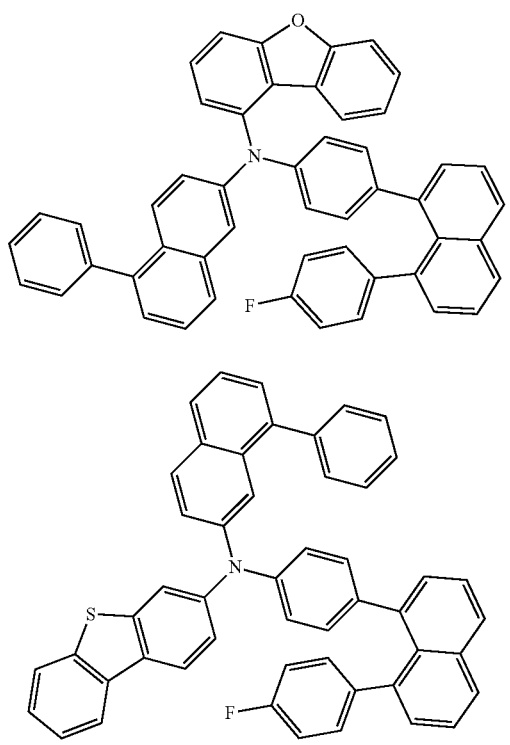
151
152
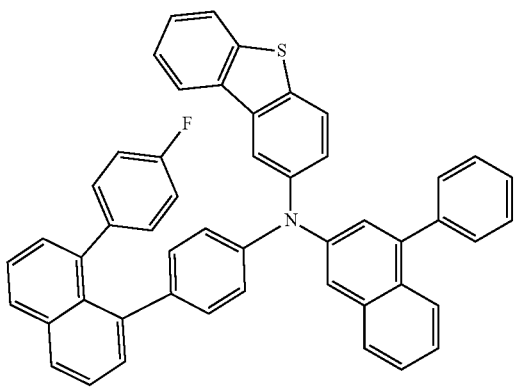
153
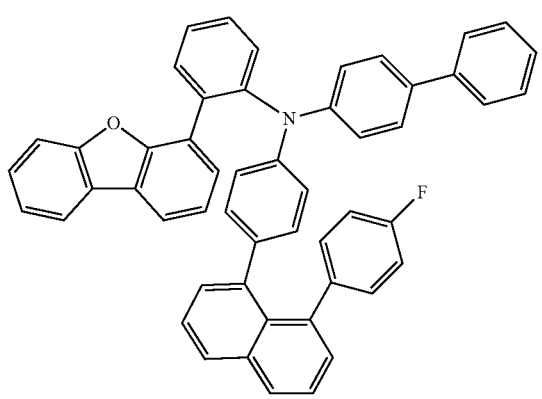
154
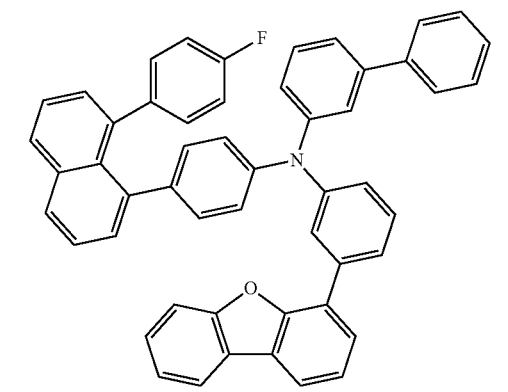

155
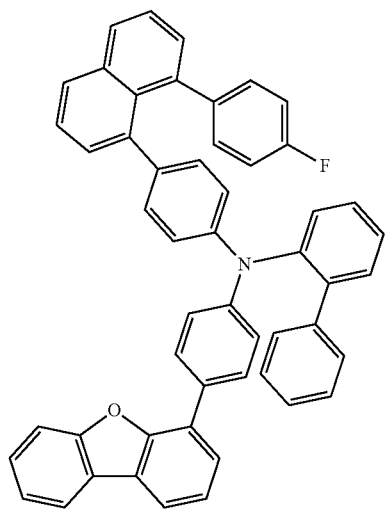
156
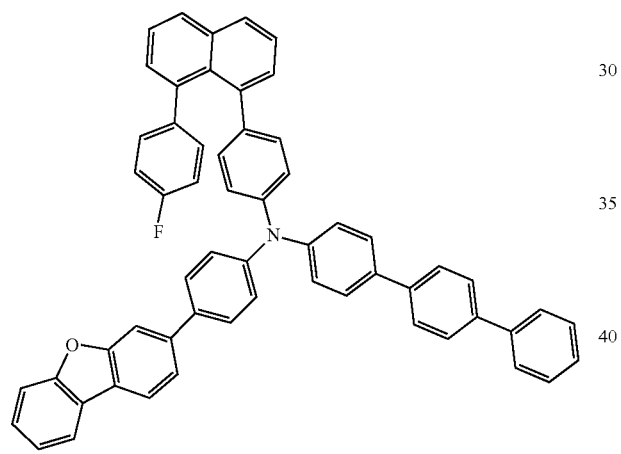
157
158
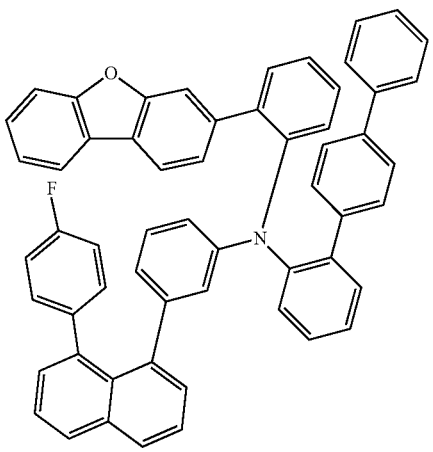
159
160
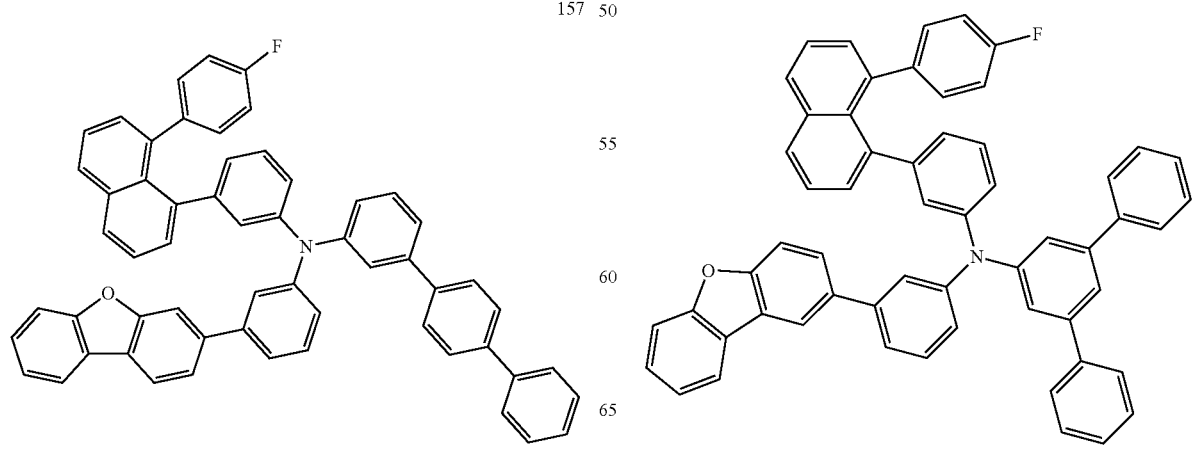

-continued
161
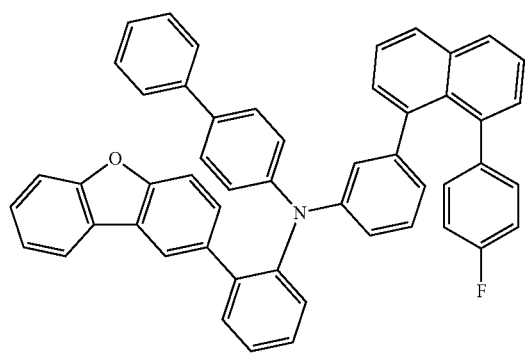
162
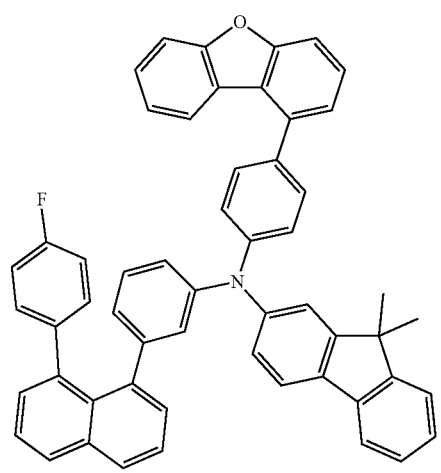
163
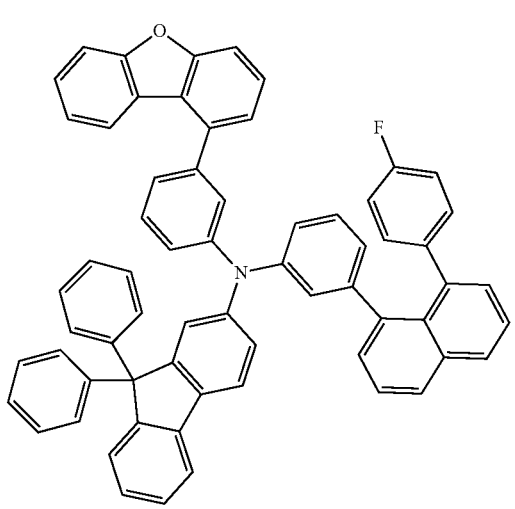
-continued
164
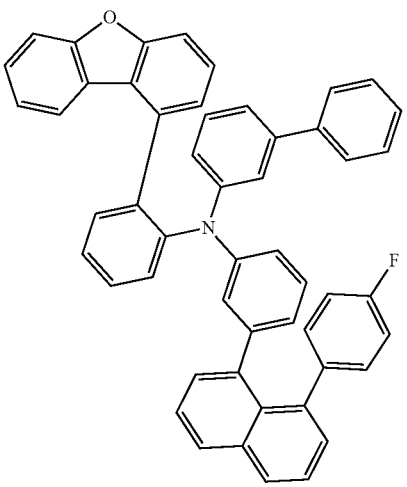
165
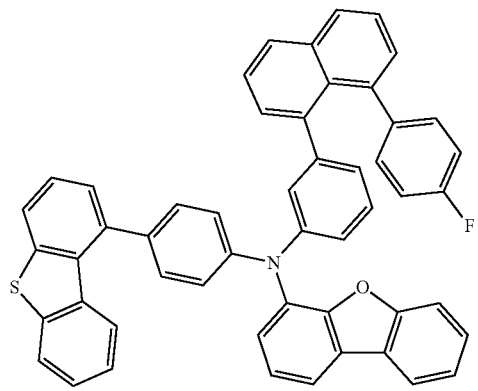
166
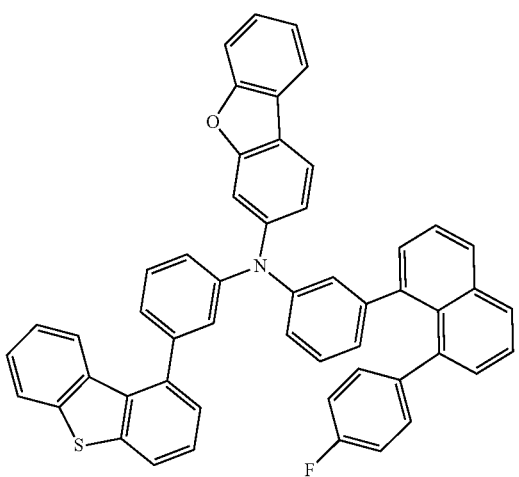

217
-continued
218
-continued
167
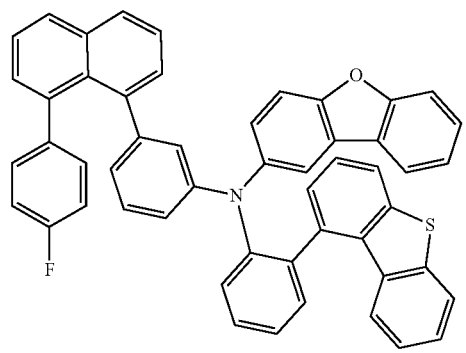
171
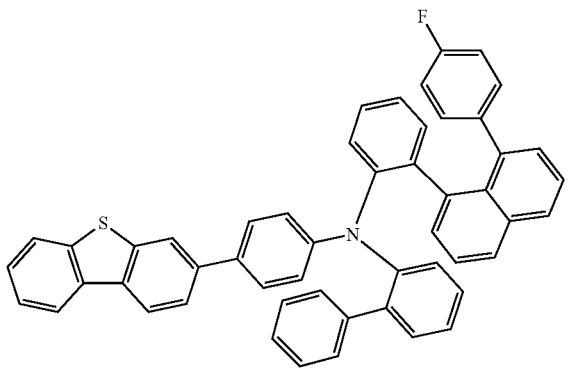
168
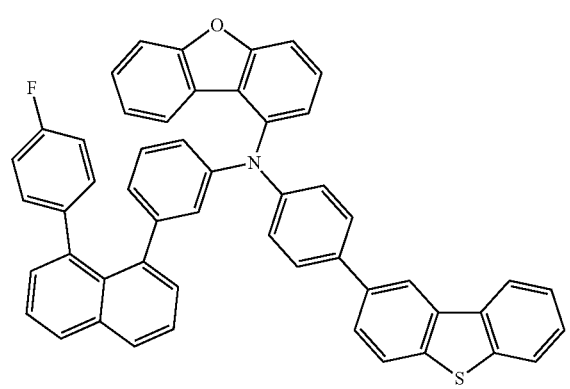
169
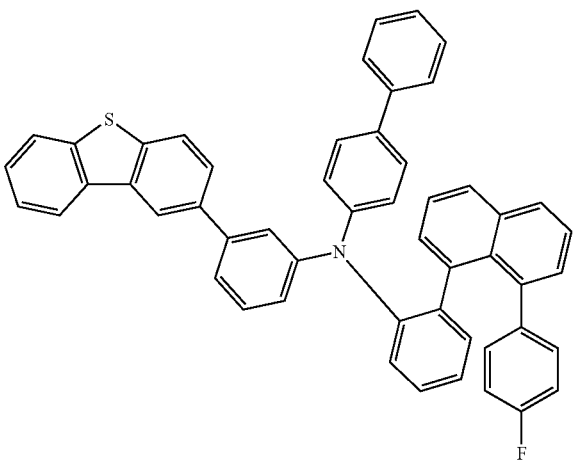
172
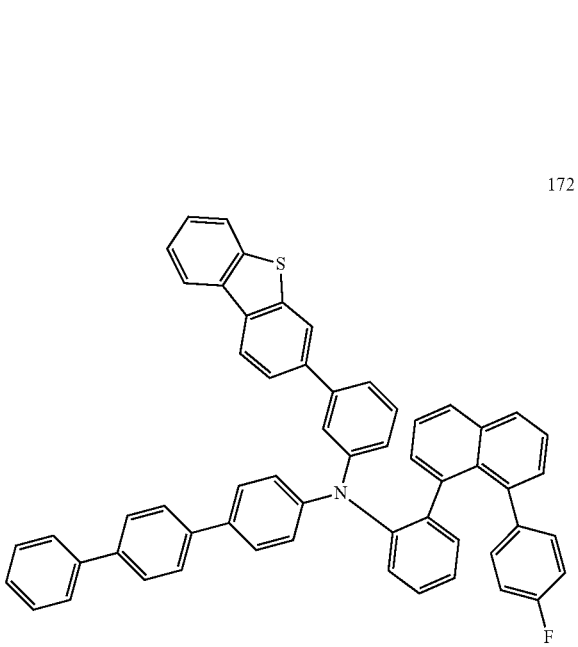
170
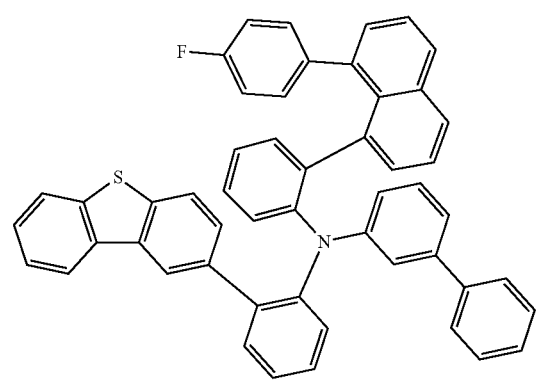
173
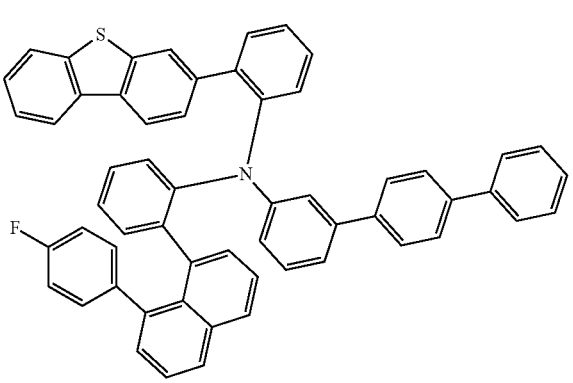

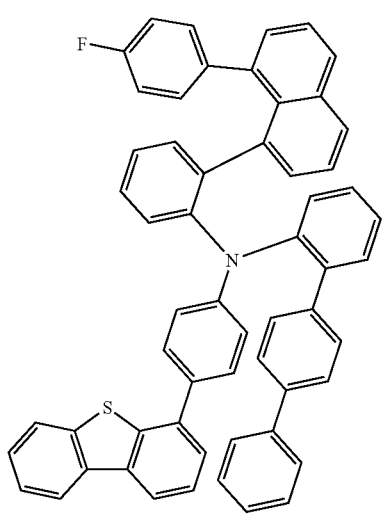
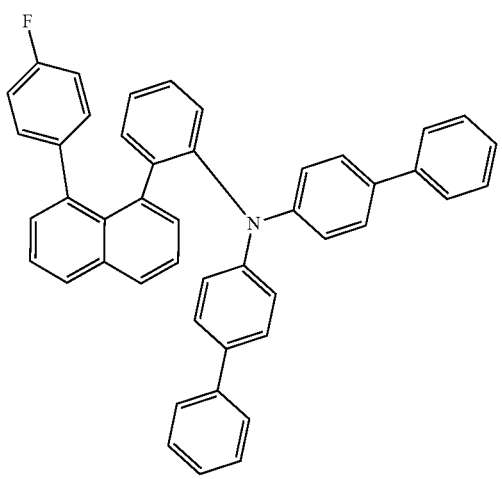
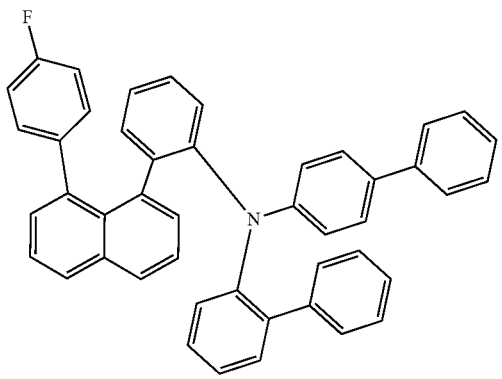

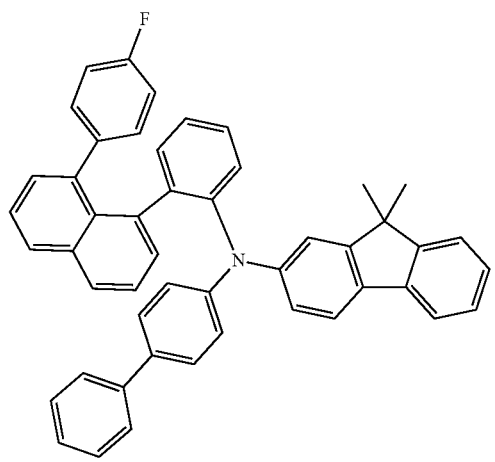
180
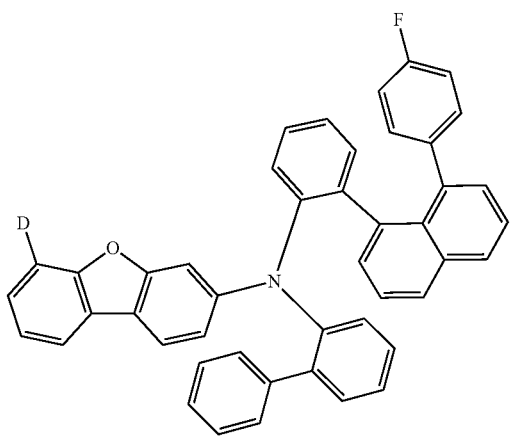
183
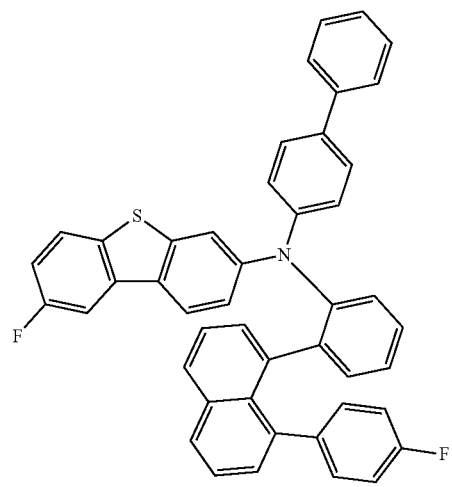
181
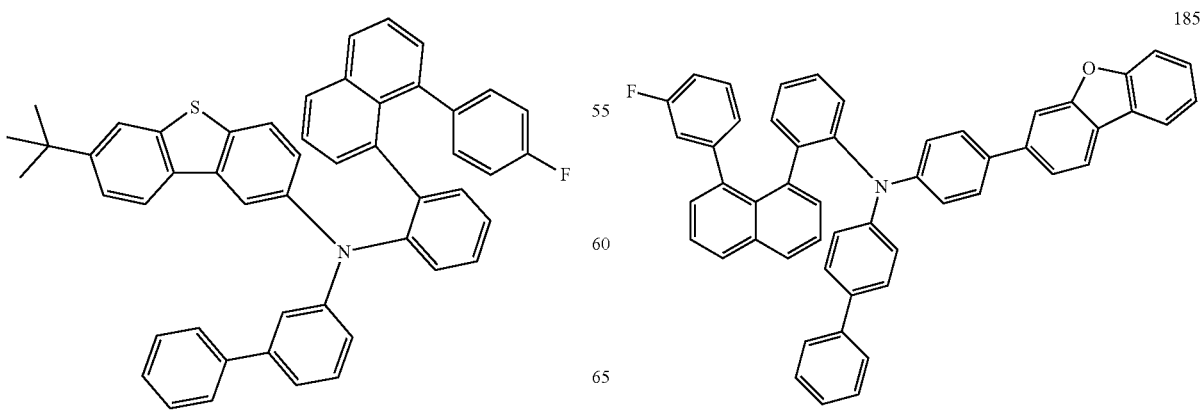
182
184
185

186
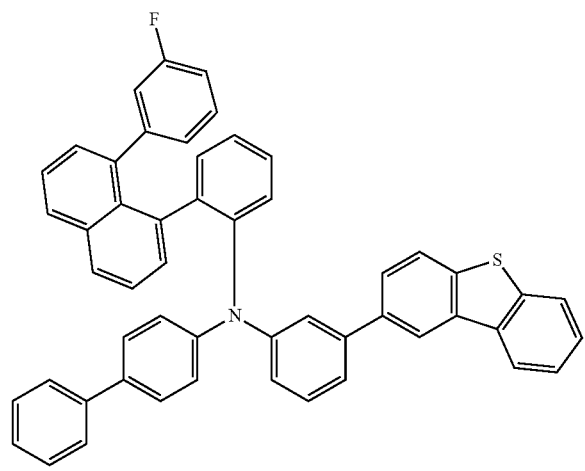
187
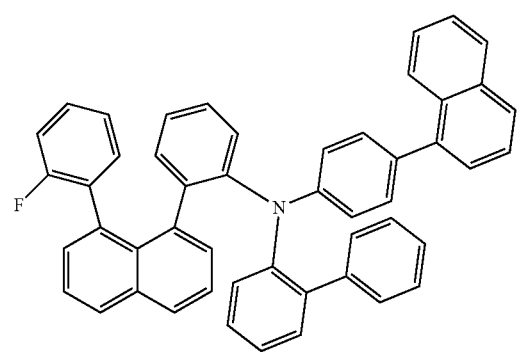
188
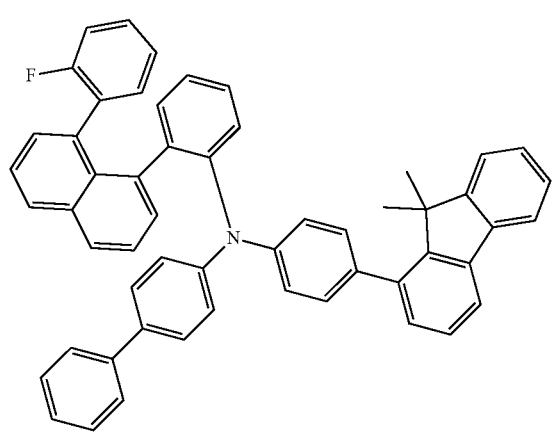
189
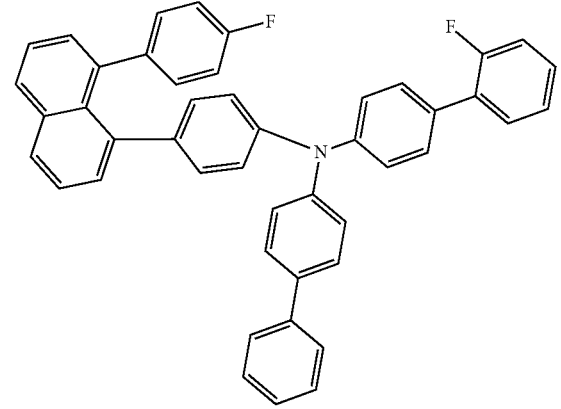
190
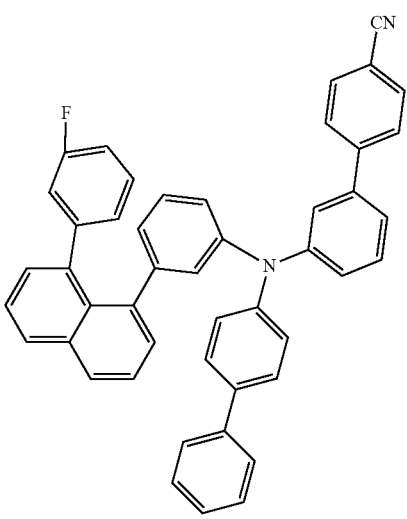
191
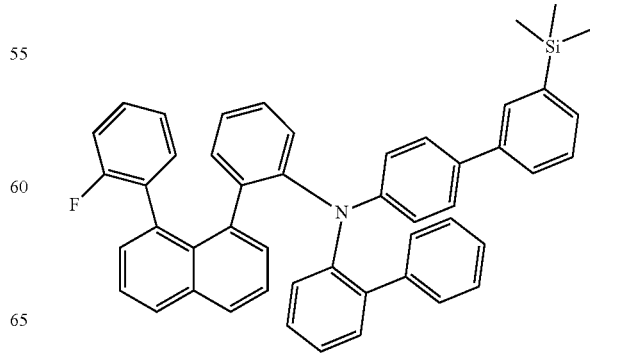

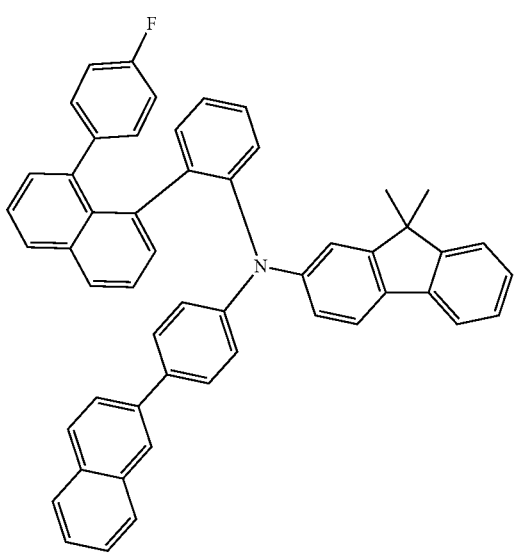
192

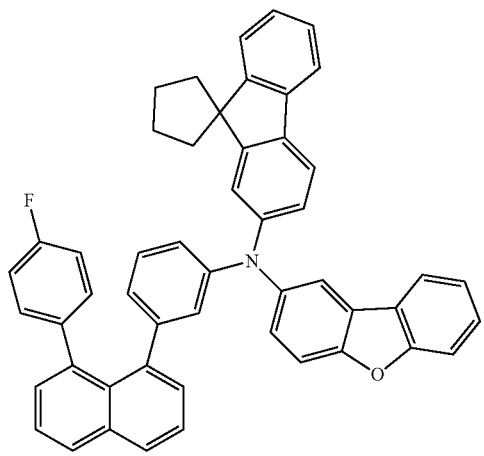
193

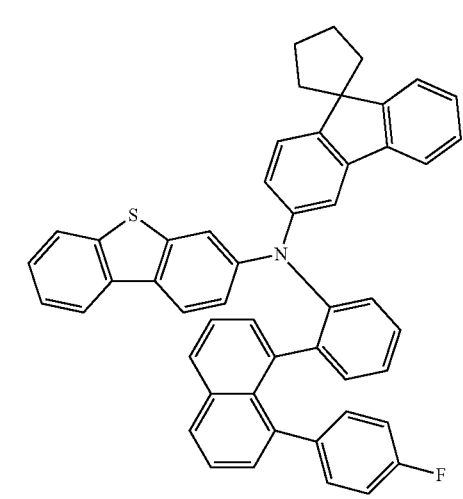
194

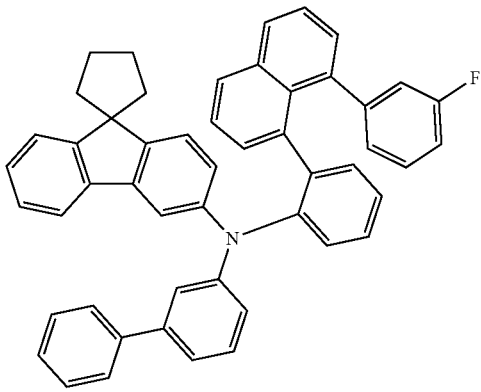
195

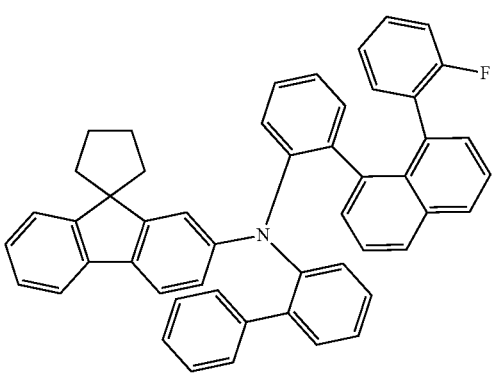
196

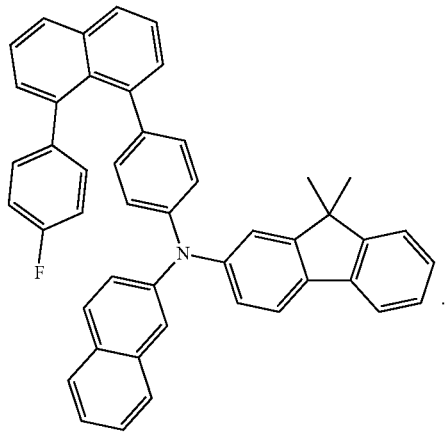
197

6. An electronic element, comprising an anode and a cathode which are oppositely disposed, and a functional layer disposed between the anode and the cathode; wherein the functional layer comprises the organic compound of claim 1.

7. The electronic element of claim 6, wherein the functional layer comprises a hole transporting layer comprising the organic compound.

8. An electronic apparatus, comprising the electronic element of claim 6.

9. The organic compound of claim 2, wherein substituents of $Ar_1$ and $Ar_2$ are selected from deuterium, a fluorine, a cyano, a trimethylsilyl, a trifluoromethyl, a methyl, an ethyl, an isopropyl, a tert-butyl, a phenyl, a naphthyl or a biphenyl; and optionally, in $Ar_1$ and $Ar_2$, any two adjacent substituents form a cyclopentane, a cyclohexane, a fluorene ring, or a tert-butyl substituted fluorene ring.

10. The electronic element of claim 7, wherein the electronic element is an organic electroluminescent device or a photoelectric conversion device.

11. The electronic element of claim 7, wherein the electronic element is an organic electroluminescent device, and the hole transporting layer comprises a first hole transporting layer and a second hole transporting layer, the first hole transporting layer being closer to the anode relative to the second hole transporting layer, wherein the second hole transporting layer comprises the organic compound.

* * * * *